(12) United States Patent
McCormack et al.

(10) Patent No.: US 10,172,721 B2
(45) Date of Patent: Jan. 8, 2019

(54) SPINAL FACET CAGE IMPLANT

(71) Applicant: Providence Medical Technology, Inc., Walnut Creek, CA (US)

(72) Inventors: Bruce M. McCormack, San Francisco, CA (US); Edward Liou, Los Altos, CA (US); David Michael Schummers, San Francisco, CA (US); Jeffrey D. Smith, Lafayette, CA (US)

(73) Assignee: PROVIDENCE TECHNOLOGY, INC., Pleasanton, CA (US)

( * ) Notice: Subject to any disclaimer, the term of this patent is extended or adjusted under 35 U.S.C. 154(b) by 0 days.

(21) Appl. No.: 15/149,781

(22) Filed: May 9, 2016

(65) Prior Publication Data

US 2016/0317316 A1 Nov. 3, 2016

Related U.S. Application Data

(63) Continuation of application No. 14/037,198, filed on Sep. 25, 2013, now Pat. No. 9,333,086, which is a
(Continued)

(51) Int. Cl.
*A61F 2/44* (2006.01)
*A61B 17/02* (2006.01)
(Continued)

(52) U.S. Cl.
CPC ............ *A61F 2/447* (2013.01); *A61B 17/025* (2013.01); *A61B 17/1604* (2013.01);
(Continued)

(58) Field of Classification Search
CPC .............. A61B 17/7064; A61B 17/025; A61B 17/1659; A61B 17/1757
(Continued)

(56) References Cited

U.S. PATENT DOCUMENTS 1,934,962 A 11/1933 Barry
2,708,376 A 5/1955 Booth
(Continued)

FOREIGN PATENT DOCUMENTS

DE    G9304368.6 U1   5/2003
FR    2722980 A1      2/1996
(Continued)

OTHER PUBLICATIONS

US 7,063,700, 06/2006, Michelson (withdrawn)
(Continued)

*Primary Examiner* — Christopher Beccia
(74) *Attorney, Agent, or Firm* — Dorsey & Whitney LLP

(57) ABSTRACT

Implementations described and claimed herein provide a spinal facet cage implant for implantation in a spinal facet joint. In one implementation, the implant includes a distal leading end, a proximal trailing end, a first face, and a second face. The distal leading end has a distal surface generally opposite a proximal surface of the proximal trailing end. The first face has a first surface that is generally parallel with a second surface of the second face. The first and second faces extend between the distal leading end and the proximal trailing end. The first and second surfaces having one or more textured features adapted to provide friction with the spinal facet joint. One or more windows are defined in the first and/or second surfaces, and one or more side windows are defined in the first and/or second side surfaces.

20 Claims, 49 Drawing Sheets

Related U.S. Application Data continuation-in-part of application No. 13/614,372, filed on Sep. 13, 2012, now Pat. No. 8,753,377, which is a continuation of application No. 12/653,283, filed on Dec. 10, 2009, now Pat. No. 8,425,558, which is a continuation-in-part of application No. 12/455,814, filed on Jun. 5, 2009, now Pat. No. 8,361,152, which is a continuation-in-part of application No. 12/317,682, filed on Dec. 23, 2008, now Pat. No. 8,267,966.

(60) Provisional application No. 61/777,751, filed on Mar. 12, 2013, provisional application No. 61/705,365, filed on Sep. 25, 2012, provisional application No. 61/815,977, filed on Apr. 25, 2013, provisional application No. 61/109,776, filed on Oct. 30, 2008, provisional application No. 61/059,723, filed on Jun. 6, 2008, provisional application No. 61/169,601, filed on Apr. 15, 2009.

(51) Int. Cl.
| | |
|---|---|
| A61B 17/16 | (2006.01) |
| A61B 17/17 | (2006.01) |
| A61B 17/70 | (2006.01) |
| A61B 17/88 | (2006.01) |
| A61B 90/00 | (2016.01) |
| A61F 2/28 | (2006.01) |
| A61F 2/30 | (2006.01) |
| A61F 2/46 | (2006.01) |
| A61B 17/00 | (2006.01) |
| A61B 17/32 | (2006.01) |

(52) U.S. Cl.
CPC ...... *A61B 17/1659* (2013.01); *A61B 17/1671* (2013.01); *A61B 17/1735* (2013.01); *A61B 17/1757* (2013.01); *A61B 17/7064* (2013.01); *A61B 17/8819* (2013.01); *A61F 2/4405* (2013.01); *A61F 2/4455* (2013.01); *A61B 2017/00424* (2013.01); *A61B 2017/00429* (2013.01); *A61B 2017/0256* (2013.01); *A61B 2017/320028* (2013.01); *A61B 2090/034* (2016.02); *A61B 2090/037* (2016.02); *A61F 2002/2835* (2013.01); *A61F 2002/30377* (2013.01); *A61F 2002/30378* (2013.01); *A61F 2002/30777* (2013.01); *A61F 2002/30785* (2013.01); *A61F 2002/30789* (2013.01); *A61F 2002/30828* (2013.01); *A61F 2002/30841* (2013.01); *A61F 2002/30843* (2013.01); *A61F 2002/30848* (2013.01); *A61F 2002/30878* (2013.01); *A61F 2002/30904* (2013.01); *A61F 2002/4475* (2013.01); *A61F 2002/4629* (2013.01); *A61F 2220/0016* (2013.01)

(58) Field of Classification Search
USPC .......................................... 623/17.11–17.16
See application file for complete search history.

(56) References Cited

U.S. PATENT DOCUMENTS

| | | |
|---|---|---|
| 2,984,241 A | 5/1961 | Carlson |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |

(56) References Cited

U.S. PATENT DOCUMENTS

| | | |
|---|---|---|
| 6,514,256 B2 | 2/2003 | Zucherman et al. |
| 6,530,955 B2 * | 3/2003 | Boyle ............... A61F 2/4465 623/17.11 |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 * | 11/2005 | Gordon ............... A61F 2/442 623/17.14 |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 * | 4/2011 | Curran ............... A61F 2/447 623/17.16 |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |

(56) References Cited

U.S. PATENT DOCUMENTS

| | | | |
|---|---|---|---|
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,512,347 B2 | 8/2013 | McCormack et al. |
| 8,523,908 B2 | 9/2013 | Malone |
| 8,623,054 B2 | 1/2014 | McCormack et al. |
| 8,668,722 B2 | 3/2014 | Pavlov et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | MccCormack et al. |
| D723,691 S | 3/2015 | McCormack et al. |
| 8,998,905 B2 | 4/2015 | Marik et al. |
| 9,011,492 B2 | 4/2015 | McCormack et al. |
| D732,667 S | 6/2015 | McCormack et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,717,403 B2 | 8/2017 | Kleiner et al. |
| 2001/0004710 A1 | 6/2001 | Felt et al. |
| 2001/0047208 A1 | 11/2001 | Michelson |
| 2002/0026195 A1 | 2/2002 | Layne et al. |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0023312 A1* | 1/2003 | Thalgott ............ A61F 2/4455 623/17.16 |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0158553 A1 | 8/2003 | Michelson |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015149 A1 | 1/2005 | Michelson |
| 2005/0027358 A1 | 2/2005 | Suddaby |
| 2005/0033432 A1 | 2/2005 | Gordon et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1* | 6/2005 | Chappuis ............ A61B 17/1671 606/86 A |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149289 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0235391 A1 | 10/2006 | Sutterlin, III |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |

(56) References Cited

U.S. PATENT DOCUMENTS

| | | |
|---|---|---|
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0179619 A1 | 8/2007 | Grob et al. |
| 2007/0225721 A1 | 9/2007 | Thelen et al. |
| 2007/0225812 A1* | 9/2007 | Gill .................. A61B 17/1671 623/17.15 |
| 2007/0244483 A9 | 10/2007 | Winslow et al. |
| 2007/0276491 A1 | 11/2007 | Ahrens |
| 2007/0282441 A1* | 12/2007 | Stream .................. A61B 17/92 623/17.11 |
| 2007/0288014 A1 | 12/2007 | Shadduck et al. |
| 2007/0299451 A1 | 12/2007 | Tulkis |
| 2008/0015581 A1* | 1/2008 | Eckman .................. A61F 2/4455 606/279 |
| 2008/0021457 A1 | 1/2008 | Anderson et al. |
| 2008/0021464 A1* | 1/2008 | Morin .................. A61B 17/7007 606/250 |
| 2008/0058954 A1 | 3/2008 | Trieu |
| 2008/0065219 A1* | 3/2008 | Dye .................. A61F 2/4465 623/17.16 |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0287955 A1 | 11/2008 | Michelson |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177237 A1 | 7/2009 | Zucherman et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0306671 A1 | 12/2009 | McCormack et al. |
| 2009/0312763 A1 | 12/2009 | McCormack et al. |
| 2010/0069912 A1 | 3/2010 | McCormack et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0191241 A1 | 7/2010 | McCormack et al. |
| 2011/0004247 A1* | 1/2011 | Lechmann .......... A61B 17/7064 606/247 |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0065613 A1 | 3/2012 | Pepper et al. |
| 2012/0143334 A1 | 6/2012 | Boyce et al. |
| 2012/0215259 A1 | 8/2012 | Cannestra |
| 2012/0265250 A1 | 10/2012 | Ali |
| 2012/0283776 A1 | 11/2012 | Mishra |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack |
| 2013/0144389 A1 | 6/2013 | Bonutti |
| 2013/0226239 A1 | 8/2013 | Altarac et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0025113 A1 | 1/2014 | McCormack et al. |
| 2014/0100657 A1 | 4/2014 | McCormack et al. |
| 2014/0379087 A1 | 12/2014 | McCormack |
| 2015/0297357 A1 | 10/2015 | McCormack et al. |
| 2017/0027713 A1 | 2/2017 | Kleiner |
| 2017/0189199 A1 | 7/2017 | Maier et al. |
| 2017/0216044 A1 | 8/2017 | McCormack |

FOREIGN PATENT DOCUMENTS

| | | |
|---|---|---|
| WO | 9641582 A1 | 12/1996 |
| WO | 99/49818 A1 | 10/1999 |
| WO | 00/35388 A1 | 6/2000 |
| WO | 00/53126 A1 | 9/2000 |
| WO | 0053126 A1 | 9/2000 |
| WO | 01/01895 A1 | 1/2001 |
| WO | 02/34120 A2 | 5/2002 |
| WO | 2002/038062 A2 | 5/2002 |
| WO | 0234120 A2 | 5/2002 |
| WO | 02076335 | 10/2002 |
| WO | 2006058221 A2 | 6/2006 |
| WO | 2006130791 A2 | 12/2006 |
| WO | 2007120903 A2 | 10/2007 |
| WO | 2008083349 A2 | 7/2008 |
| WO | 2008153732 A1 | 12/2008 |
| WO | 2009089367 A2 | 7/2009 |
| WO | 2009148619 A2 | 12/2009 |
| WO | 2010030994 | 3/2010 |
| WO | 2010074714 | 7/2010 |
| WO | 2016049784 | 4/2016 |

OTHER PUBLICATIONS

Goel, Atul, "Facetal distraction as treatment for single- and multi-level cervical spondylotic radiculopathy and myelopathy: a preliminary report," J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

(56) References Cited

OTHER PUBLICATIONS

Extended European Search Report for European Application No. 14849663.1, dated Feb. 24, 2017 (8 pages).
Stein et al., "Percutaneous Facet Joint Fusion: Preliminary Experience," Journal of Vascular and Interventional Radiology, Jan.-Feb. 1993, pp. 69-74, vol. 4, No. 1.

* cited by examiner

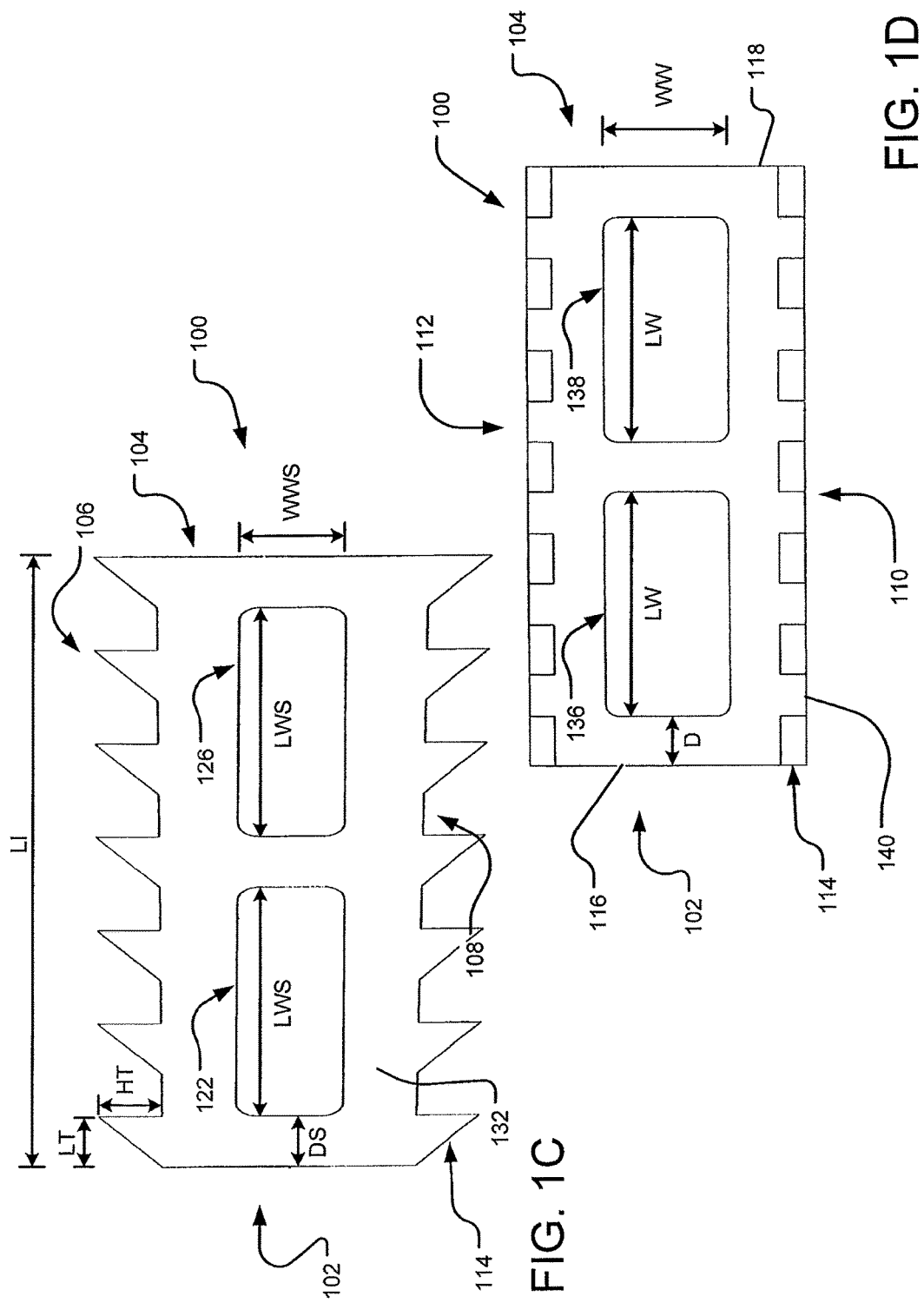

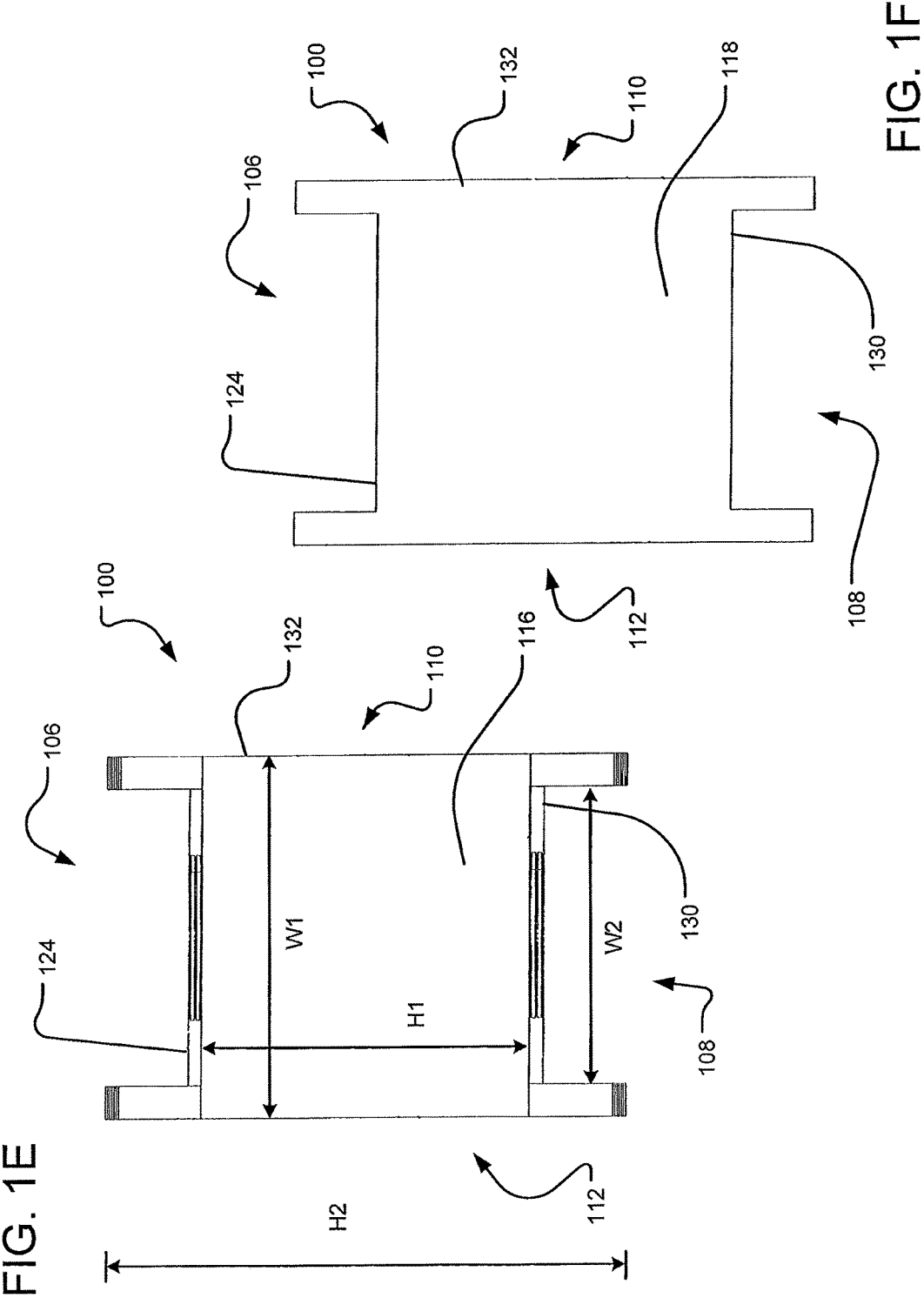

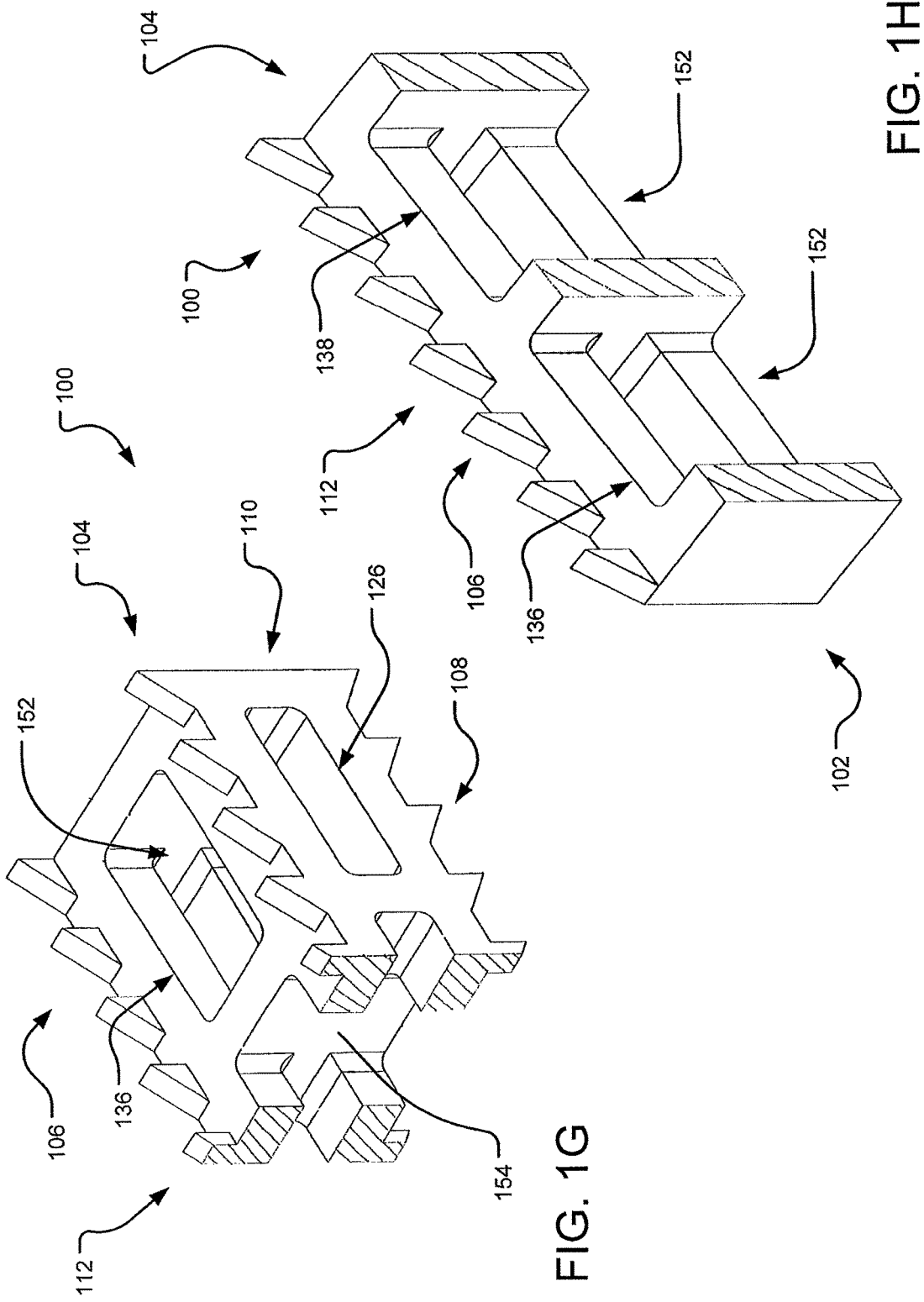

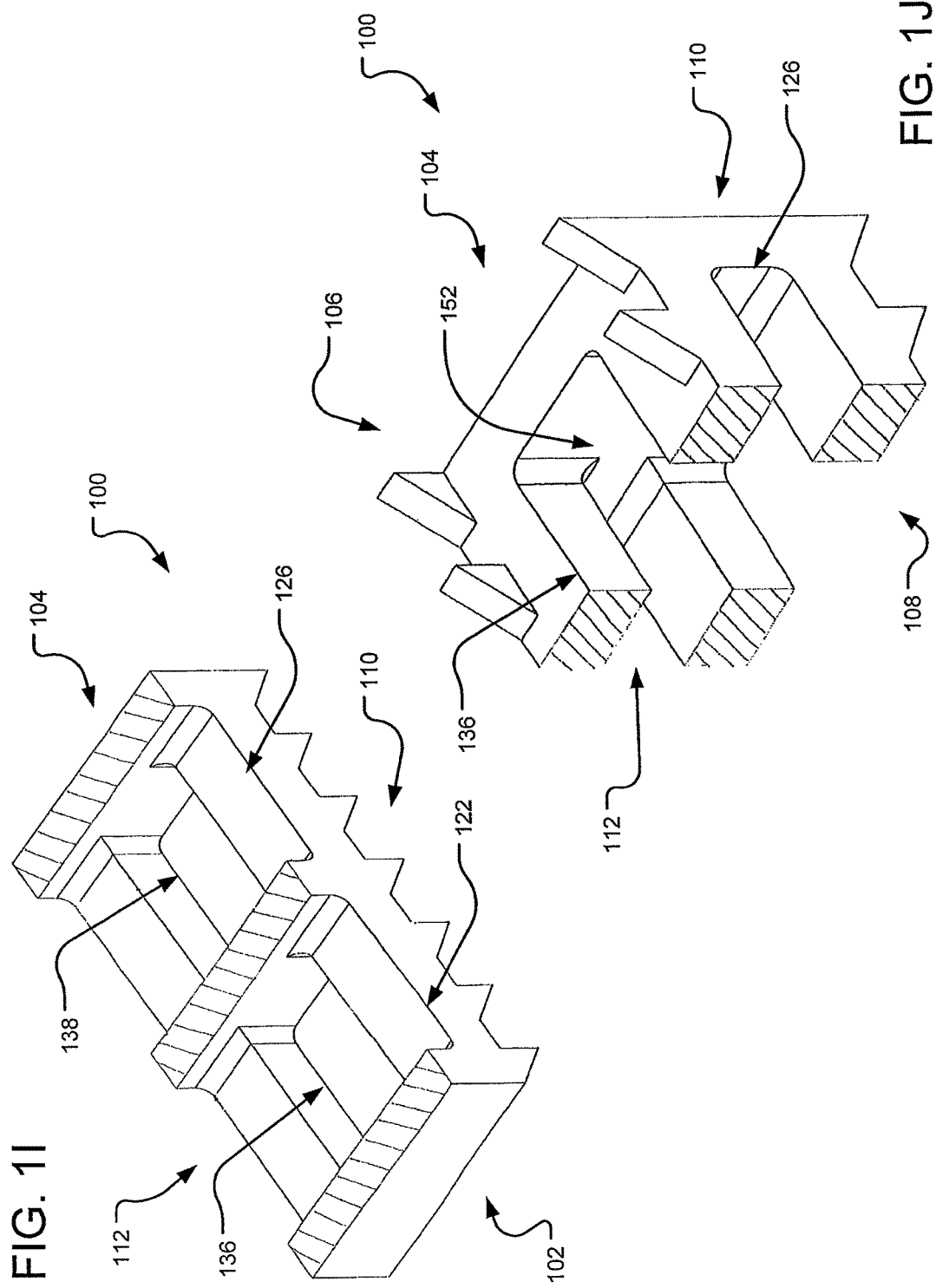

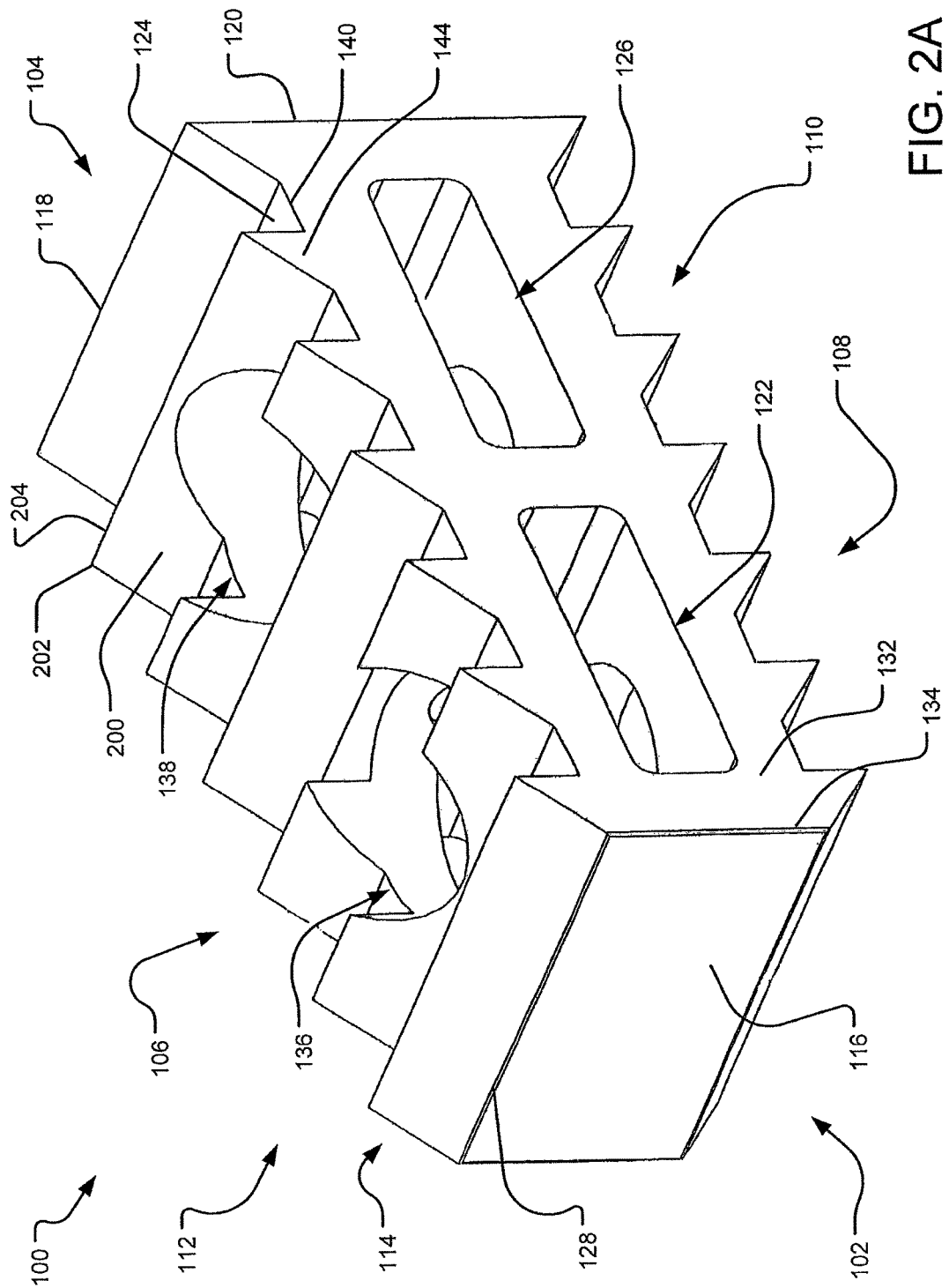

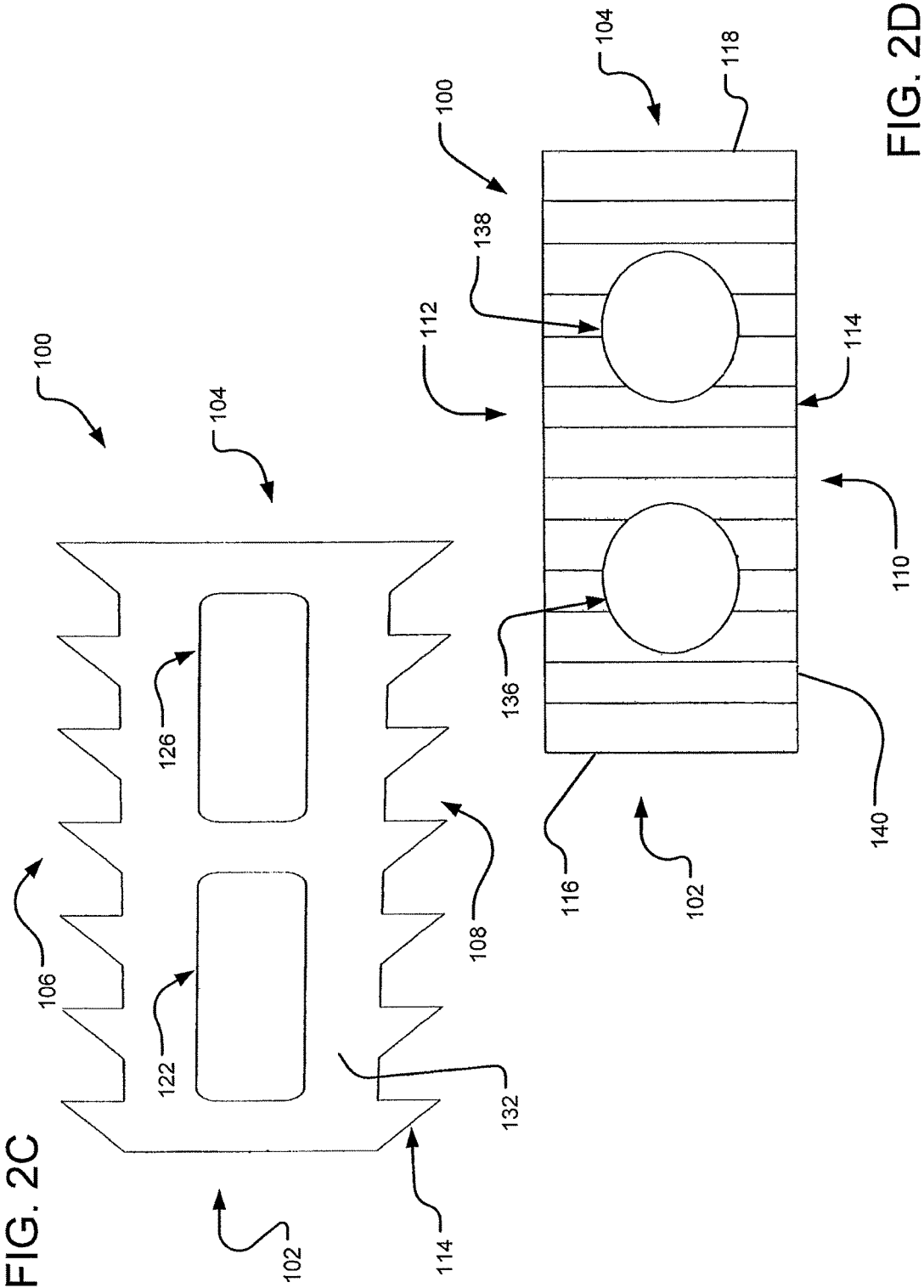

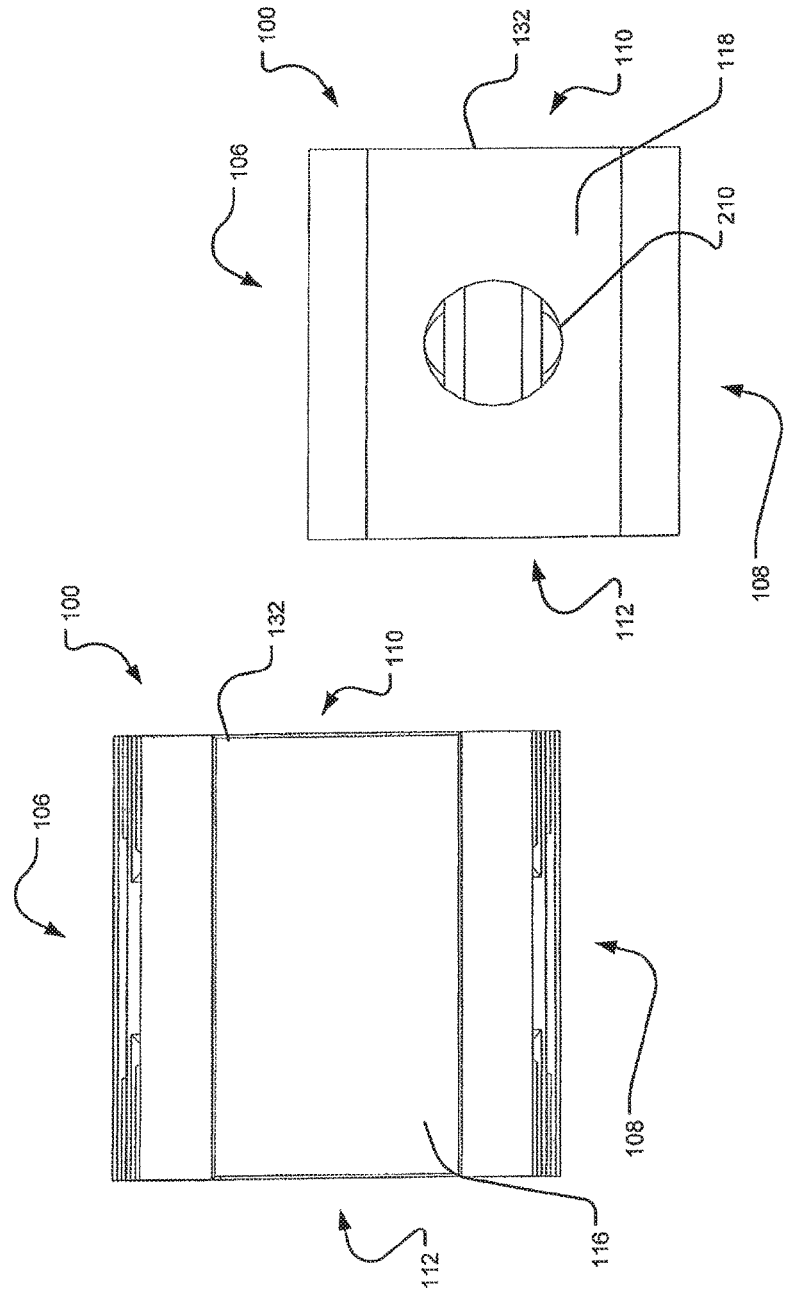

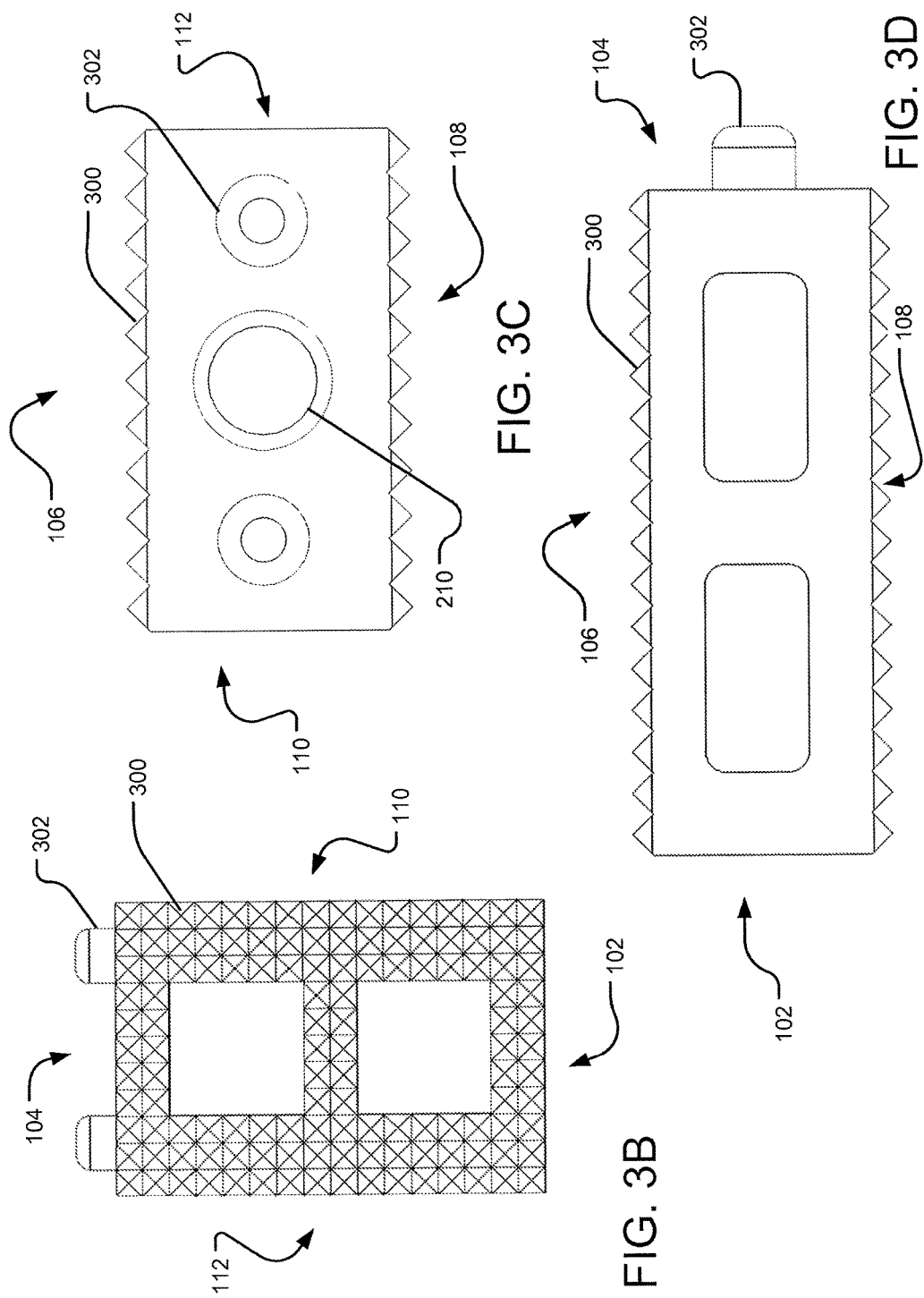

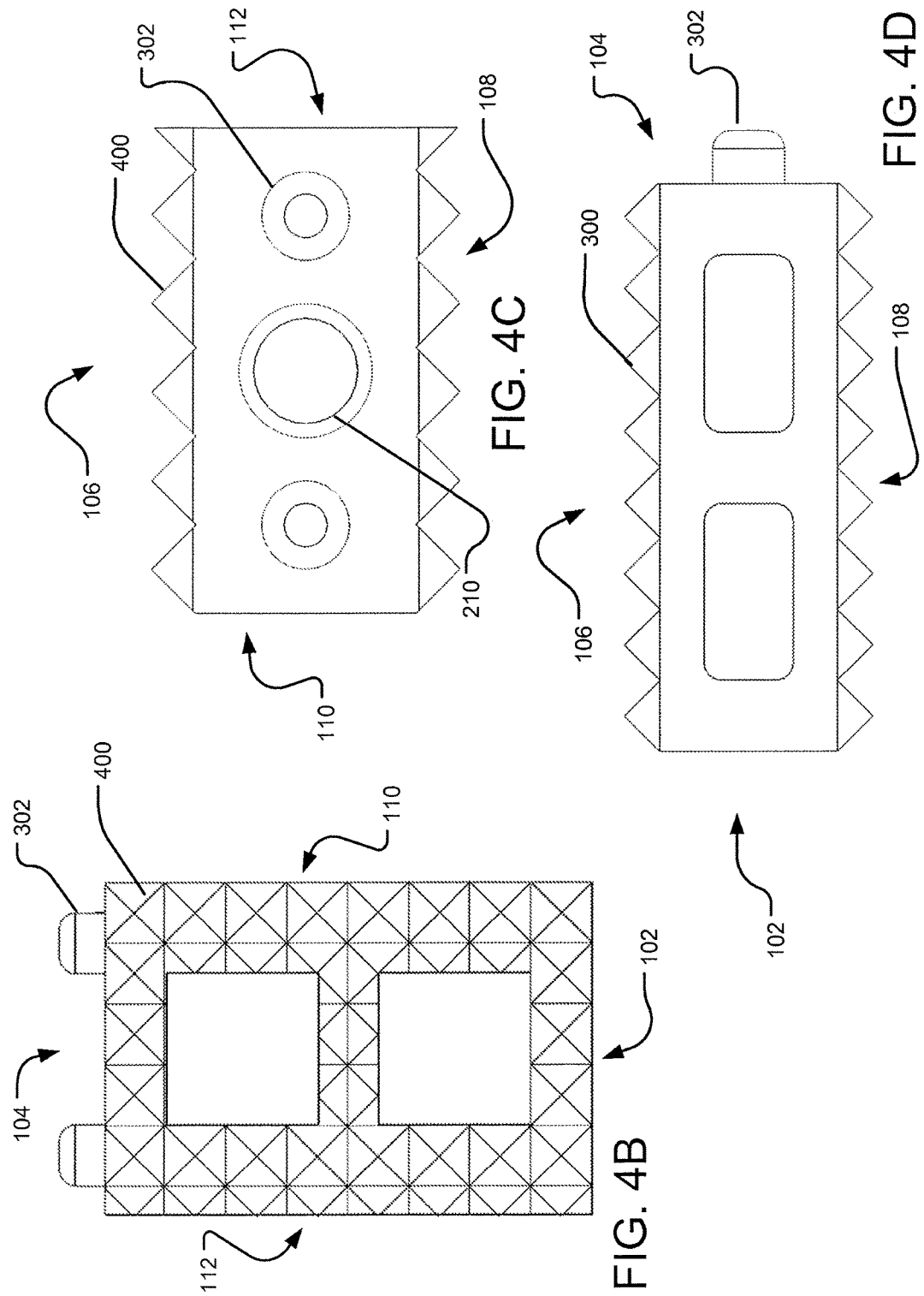

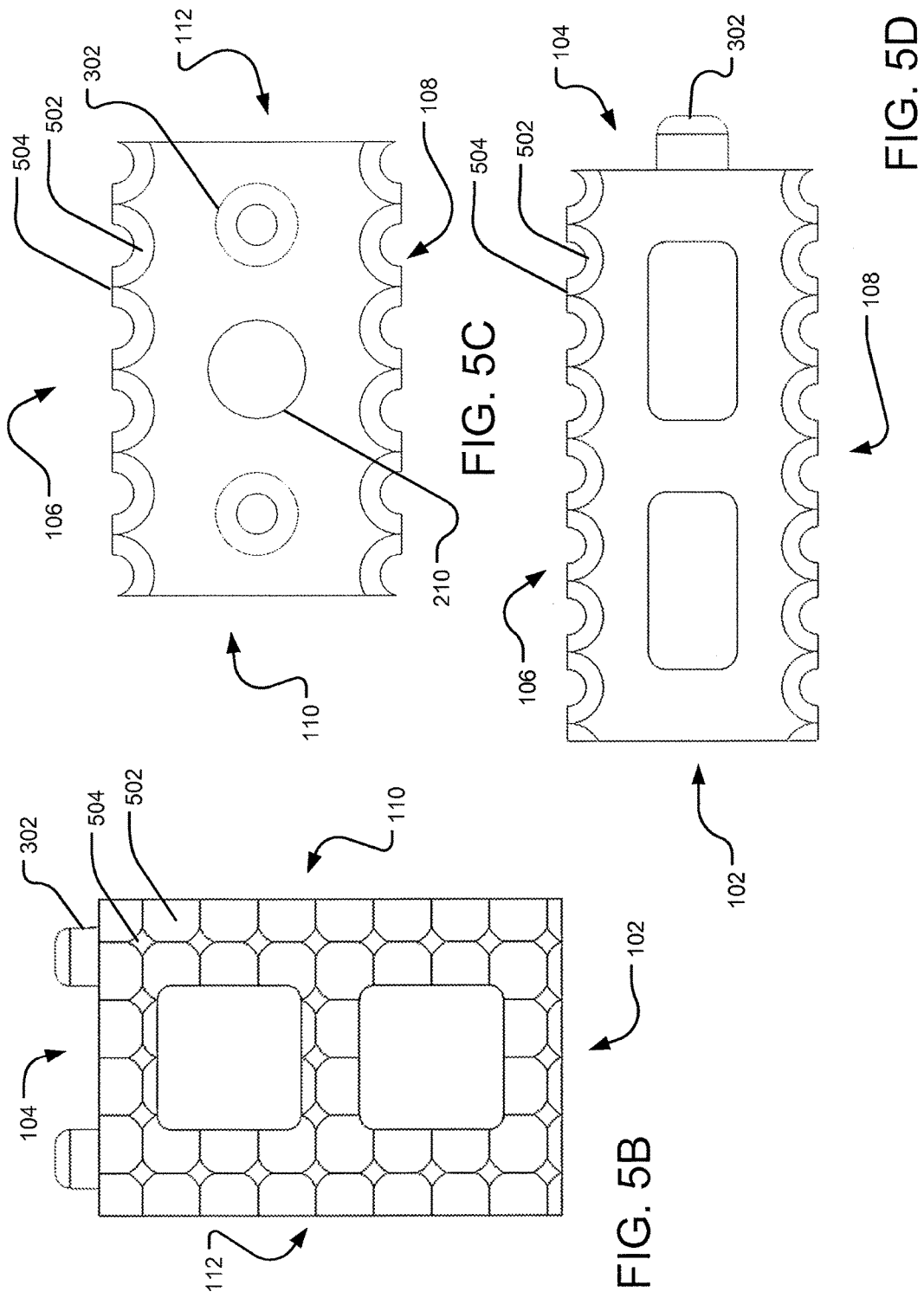

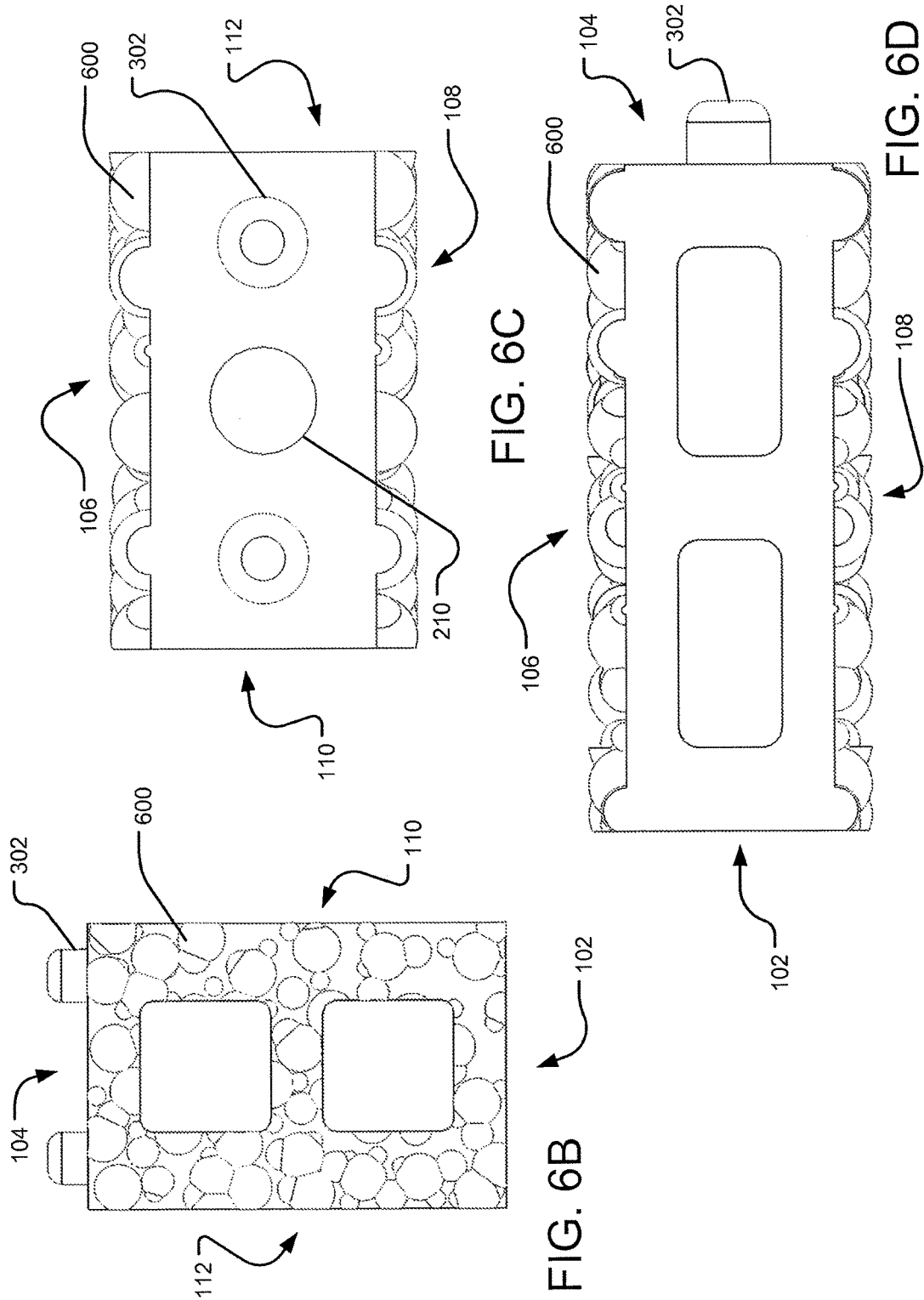

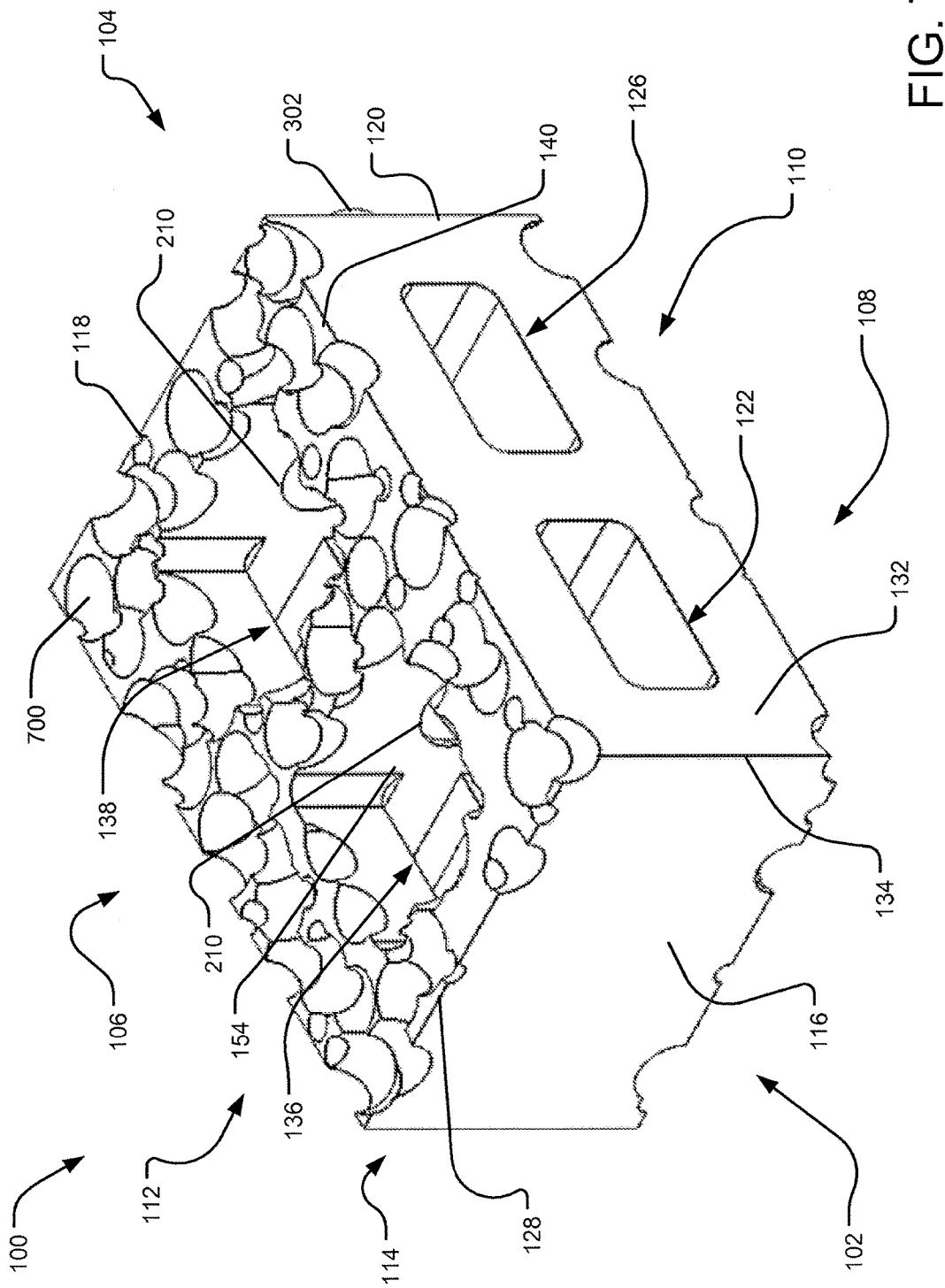

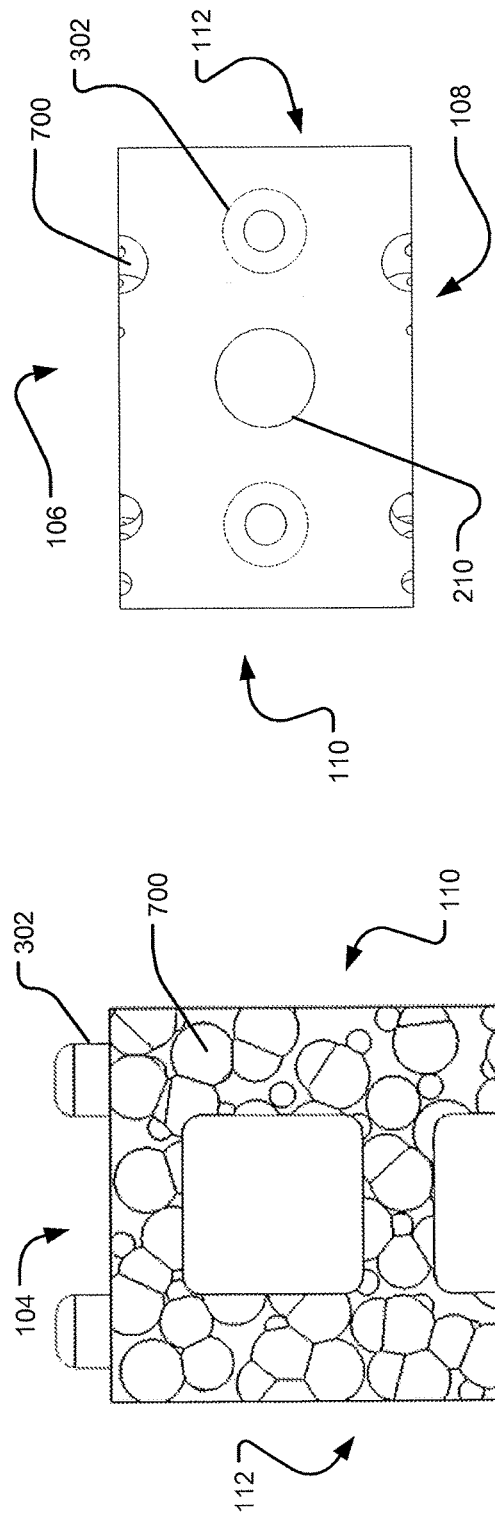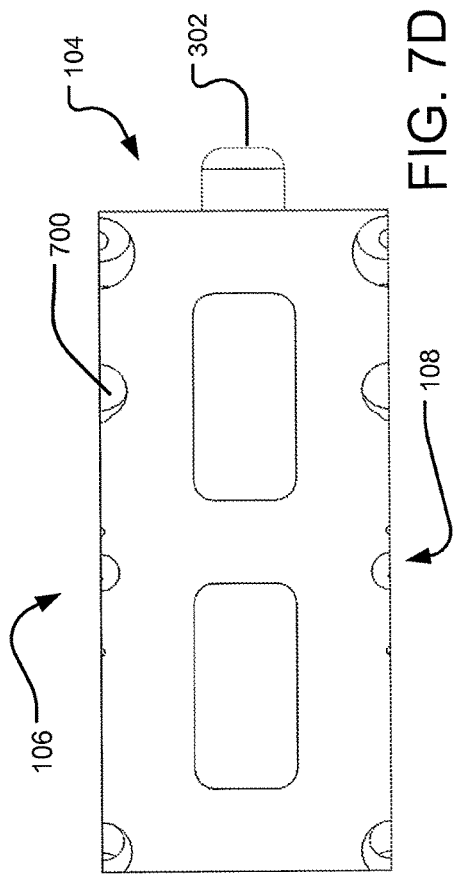

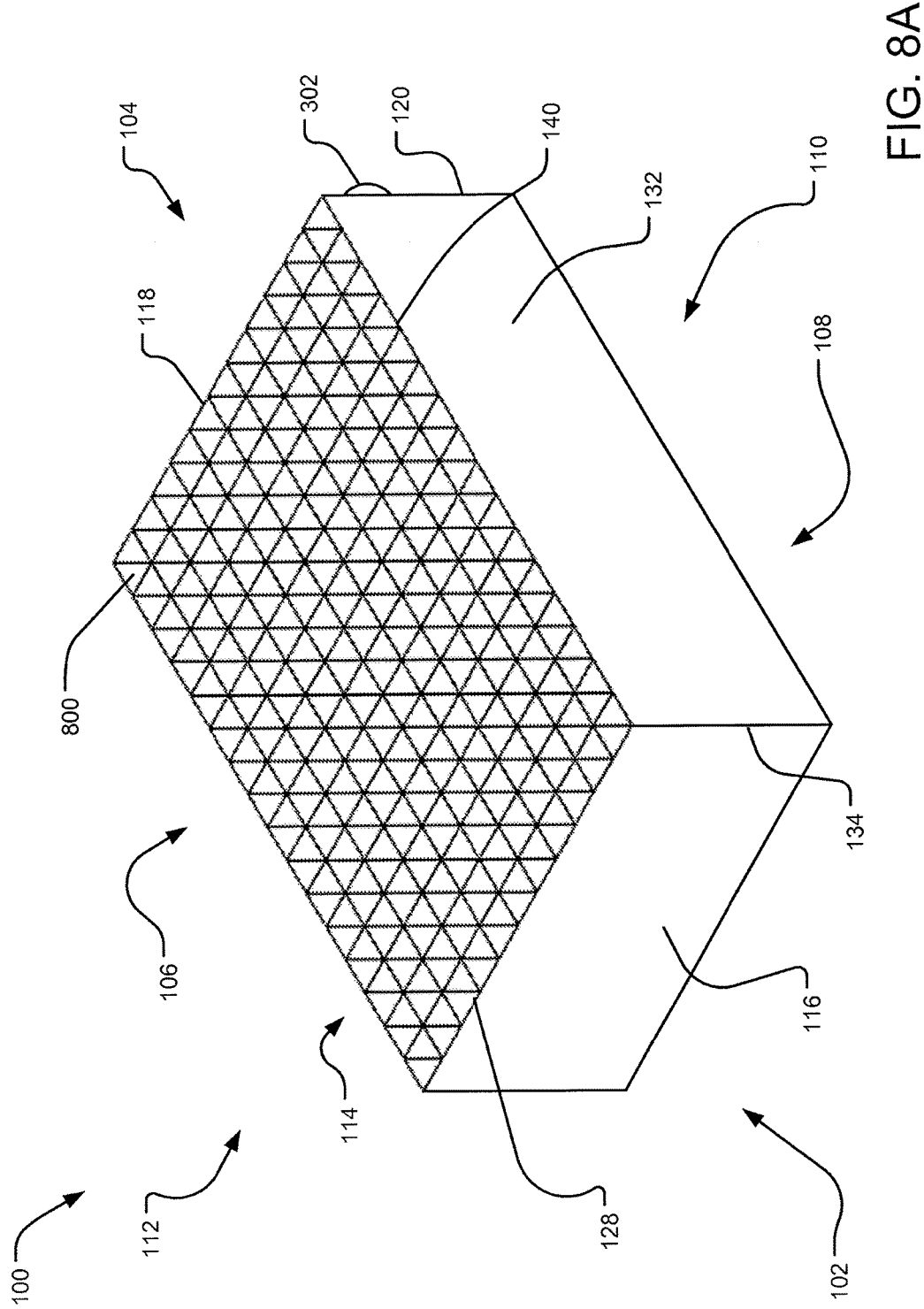

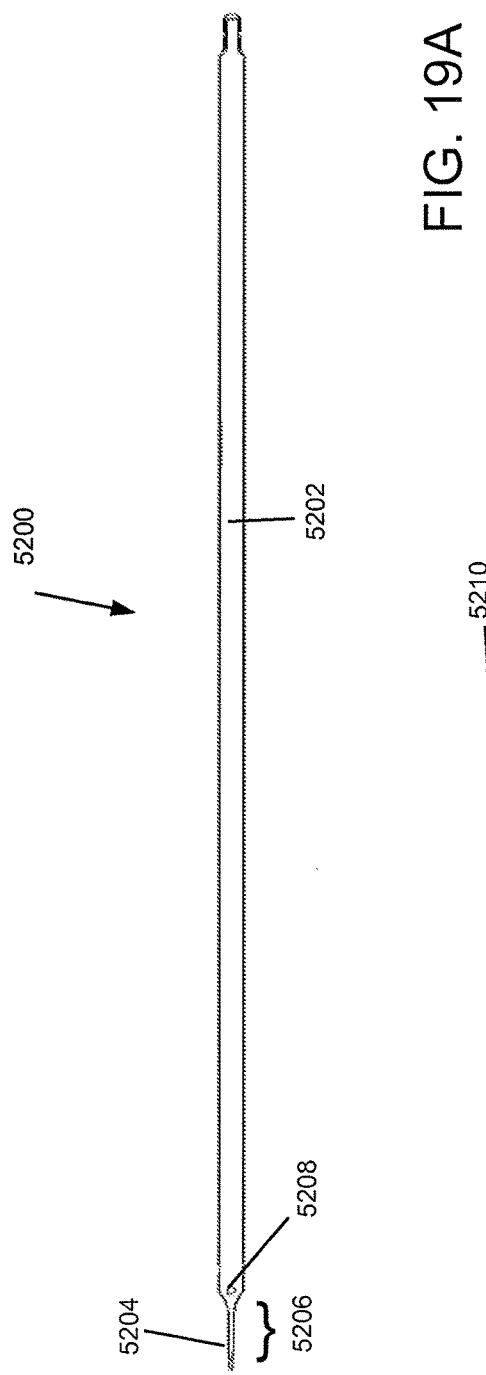
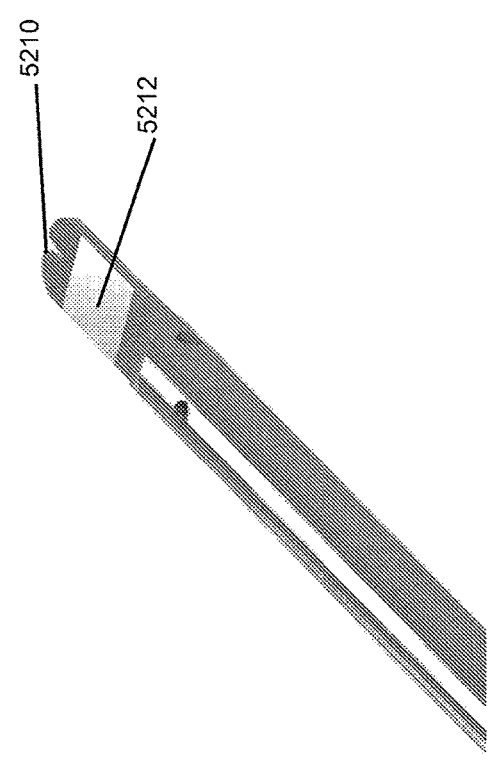
FIG. 19A
FIG. 19B

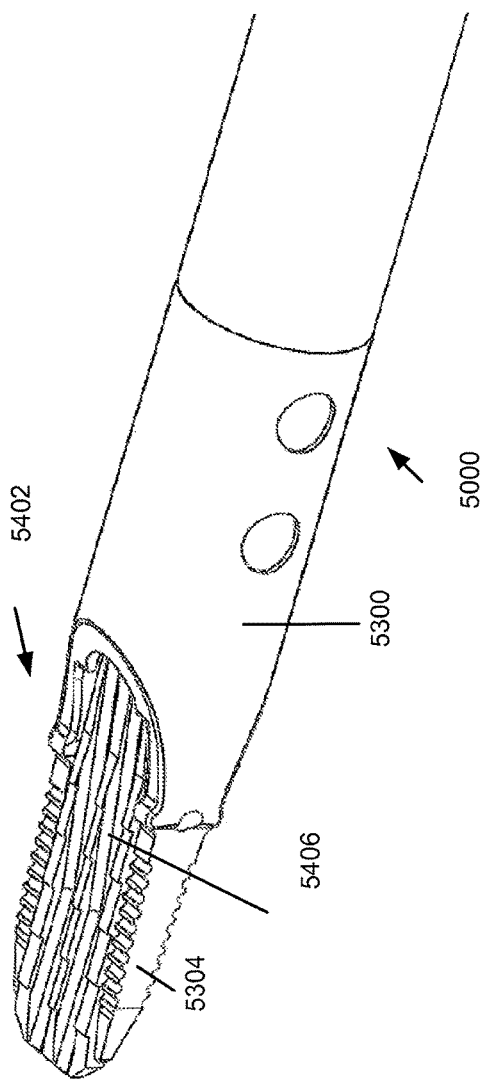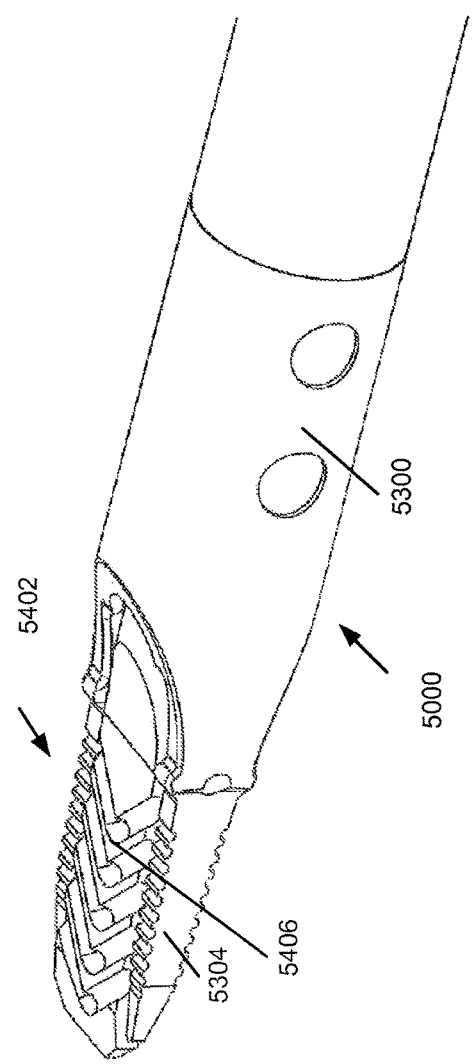

SPINAL FACET CAGE IMPLANT

CROSS-REFERENCE TO RELATED APPLICATIONS

The present application is a continuation application of U.S. application Ser. No. 14/037,198, which was filed Sep. 25, 2013, now issued as U.S. Pat. No. 9,333,086, and entitled "Spinal Facet Cage Implant", which claims priority under 35 U.S.C. § 119 to U.S. provisional patent application 61/705,365, which was filed Sep. 25, 2012; and entitled "Spinal Facet Cage Implant;" to U.S. provisional patent application 61/777,751, which was filed Mar. 12, 2013 and entitled "Spinal Facet Cage Implant" and to U.S. provisional patent application 61/815,977 filed Apr. 25, 2013 and entitled "Cage Delivery System."

The present application is a continuation application of U.S. application Ser. No. 14/037,198, which was filed Sep. 25, 2013, now issued as U.S. Pat. No. 9,333,086, and entitled "Spinal Facet Cage Implant", which claims priority to and is a continuation-in-part of U.S. patent application Ser. No. 13/614,372 filed on Sep. 13, 2012, issued as U.S. Pat. No. 8,753,377, and entitled Vertebral Joint Implants And Delivery Tools. U.S. patent application Ser. No. 13/614,372 is a continuation of U.S. patent application Ser. No. 12/653,283, which was filed on Dec. 10, 2009, now U.S. Pat. No. 8,425,558, and entitled "Verbal joint implants and Delivery Tools." U.S. patent application Ser. No. 12/653,283 claims priority to and is a continuation-in-part of U.S. patent application Ser. No. 12/455,814, which was filed on Jun. 5, 2009, now U.S. Pat. No. 8,361,152 and entitled "Facet Joint Implants and Delivery Tools." U.S. patent application Ser. No. 12/455,814 claims priority to and is a continuation-in-part of U.S. patent application Ser. No. 12/317,682, which was filed on Dec. 23, 2008, now U.S. Pat. No. 8,267,966, and entitled "Facet Joint Implants and Delivery Tools."

U.S. patent application Ser. No. 12/455,814 further claims priority under 35 U.S.C. § 119 to U.S. provisional patent application 61/169,601, which was filed on Apr. 15, 2009 and entitled "Facet Joint Implants and Delivery Tools."

U.S. patent application Ser. No. 12/317,682 claims priority under 35 U.S.C. § 119 to U.S. provisional patent application 61/109,776, which was filed Oct. 30, 2008 and entitled "Facet Joint Implants," and U.S. provisional patent application 61/059,723, which was filed on Jun. 6, 2008 and entitled "Spine Distraction Device."

Each of the aforementioned applications is hereby incorporated by reference in its entirety into the present application.

TECHNICAL FIELD

Aspects of the present disclosure relate to a device for distracting the spine and more particularly to a tool for distracting a facet joint of the spine and an implant for maintaining the distracted position of the joint.

BACKGROUND

Chronic back problems cause pain and disability for a large segment of the population. Adverse spinal conditions may be characteristic of age. In particular, spinal stenosis (including, but not limited to, central, canal, and lateral stenosis) and facet arthropathy may increase with age. Spinal stenosis results in a reduction of foraminal area (i.e. the available space for the passage of nerves and blood vessels), which may compress cervical nerve roots and cause radicular pain. Both neck extension and ipsilateral rotation, in contrast to neck flexion, may further reduce the foraminal area and contribute to pain, nerve root compression, and neural injury.

Cervical disc herniations may be a factor in spinal stenosis and may predominantly present upper extremity radicular symptoms. In this case, treatment may take the form of closed traction. A number of closed traction devices are available that alleviate pain by pulling on the head to increase foraminal height. Cervical disc herniations may also be treated with anterior and posterior surgery. Many of these surgeries are performed through an anterior approach, which requires a spinal fusion. These surgeries may be expensive and beget additional surgeries due to changing the biomechanics of the neck. There is a three percent incidence of re-operation after cervical spine surgery. Moreover, these surgeries may be highly invasive leading to long recovery times.

There is a need in the art for implants, delivery systems, and methods of implantation that facilitate the fusion of a spinal facet joint via a minimally invasive or percutaneous procedure from, for example, a posterior approach.

It is with these observations in mind, among others, that various aspects of the present disclosure were conceived and developed.

SUMMARY

Implementations described and claimed herein address the foregoing problems, among others, by providing a spinal facet cage implant for implantation in a spinal facet joint. In one implementation, the implant includes a distal leading end, a first face, and a first side. The distal leading end has a distal surface generally opposite a proximal surface of a proximal trailing end. The first face has a first surface that is generally parallel with a second surface of a second face. The first and second faces extend between the distal leading end and the proximal trailing end. The first and second surfaces having one or more textured features adapted to provide friction with the spinal facet joint. The first side has a first side surface generally opposite a second side having a second side surface. One or more windows are defined in the first surface generally opposing one or more windows defined in the second surface, and one or more side windows are defined in the first side surface generally opposing one or more windows defined in the second side surface, the windows and side windows providing access to a hollow interior of the implant.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 1A-F are front isometric, rear isometric, side, top plan, distal leading end, and proximal trailing end views, respectively, of an example spinal facet cage implant.

FIG. 1G is a transverse isometric elevation cross section of the implant of FIGS. 1A-D, as taken along section line G shown in FIG. 1A.

FIG. 1H is a longitudinal isometric elevation cross section of the implant of FIGS. 1A-D, as taken along section line H shown in FIG. 1A.

FIG. 1I is a transverse isometric plan cross section of the implant of FIGS. 1A-D, as taken along section line I shown in FIG. 1A.

FIG. 1J is a transverse isometric elevation cross section of the implant of FIGS. 1A-D, as taken along section line J shown in FIG. 1A.

FIGS. 2A-F are front isometric, rear isometric, side, top plan, distal leading end, and proximal trailing end views, respectively, of another example spinal facet cage implant.

FIGS. 3A-D show front isometric, top plan, proximal trailing end, and side views, respectively, of an example spinal facet cage implant including textured faces having small pyramids.

FIGS. 4A-D show isometric, top plan, proximal trailing end, and side views, respectively, of an example spinal facet cage implant including textured faces having large pyramids.

FIGS. 5A-D are isometric, top plan, proximal trailing end, and side views, respectively, of an example spinal facet cage implant including textured faces having dimples.

FIGS. 6A-D show isometric, top plan, proximal trailing end, and side views, respectively, of an example including textured faces having grit.

FIGS. 7A-D depict isometric, top plan, proximal trailing end, and side views, respectively, of an example spinal facet cage implant including textured faces having pits.

FIGS. 8A-D show isometric, top plan, proximal trailing end, and side views, respectively, of an example spinal facet cage implant including textured faces having pyramids.

FIG. 19A is a side view of a place holding or access chisel.

FIG. 19B is an enlarged perspective view of a distal portion of the chisel of FIG. 19A.

FIGS. 24 and 25 are perspective views of various distal tip portions of the decorticating chisel positioned between distal spaced-apart forks of the distal end of the guide tool.

DETAILED DESCRIPTION

Figure 1A:
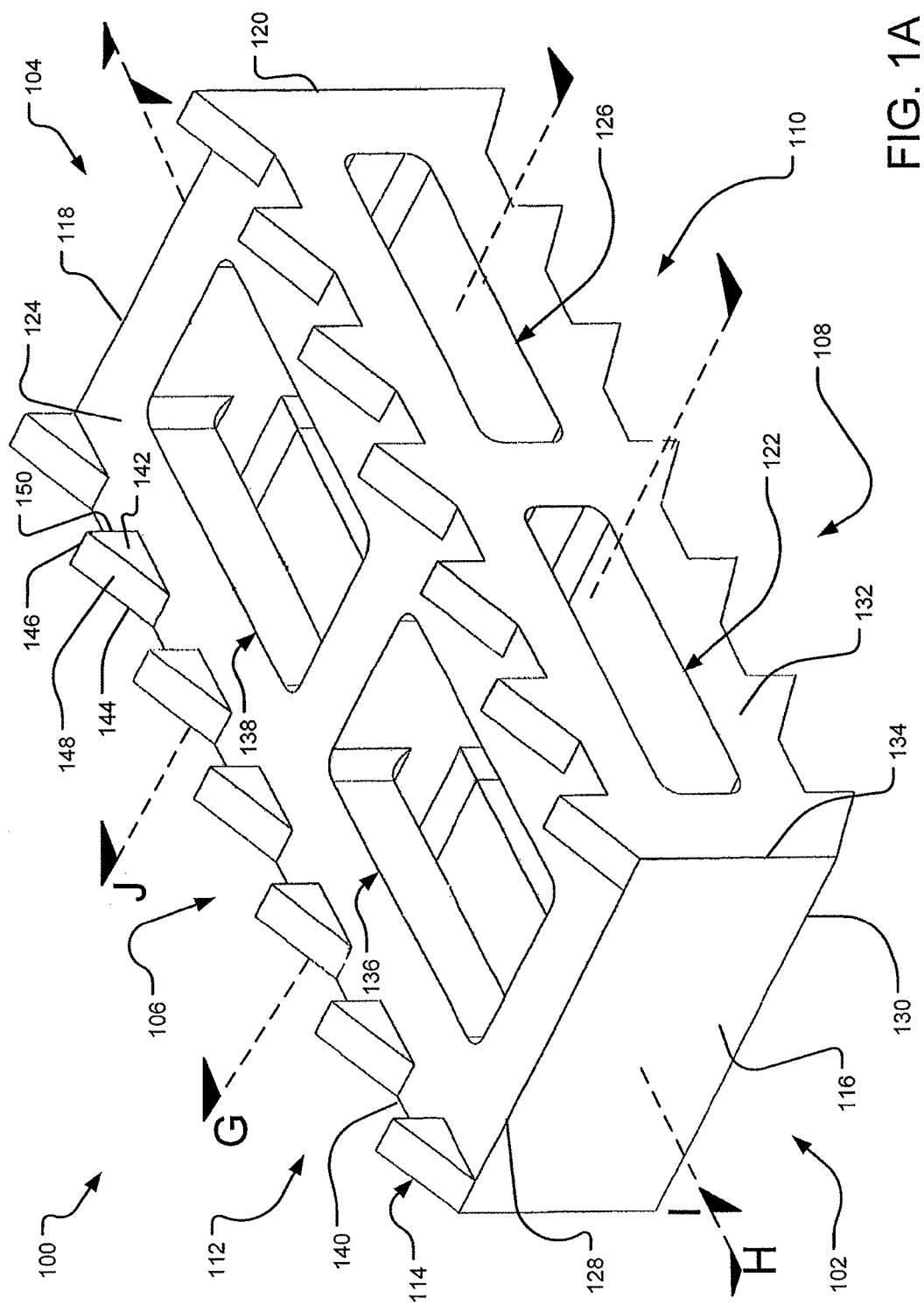
Figure 1B:
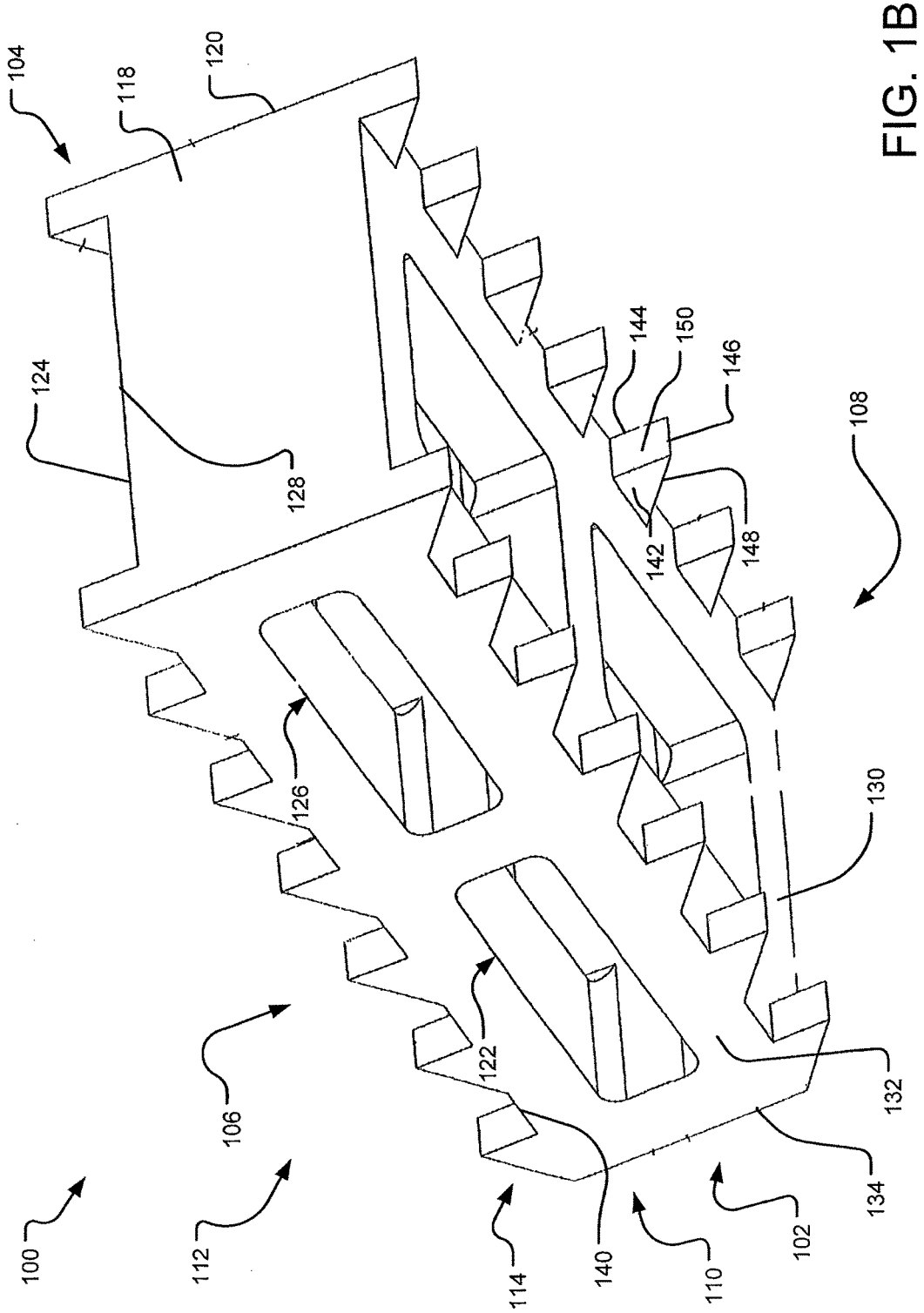
Figure 2B:
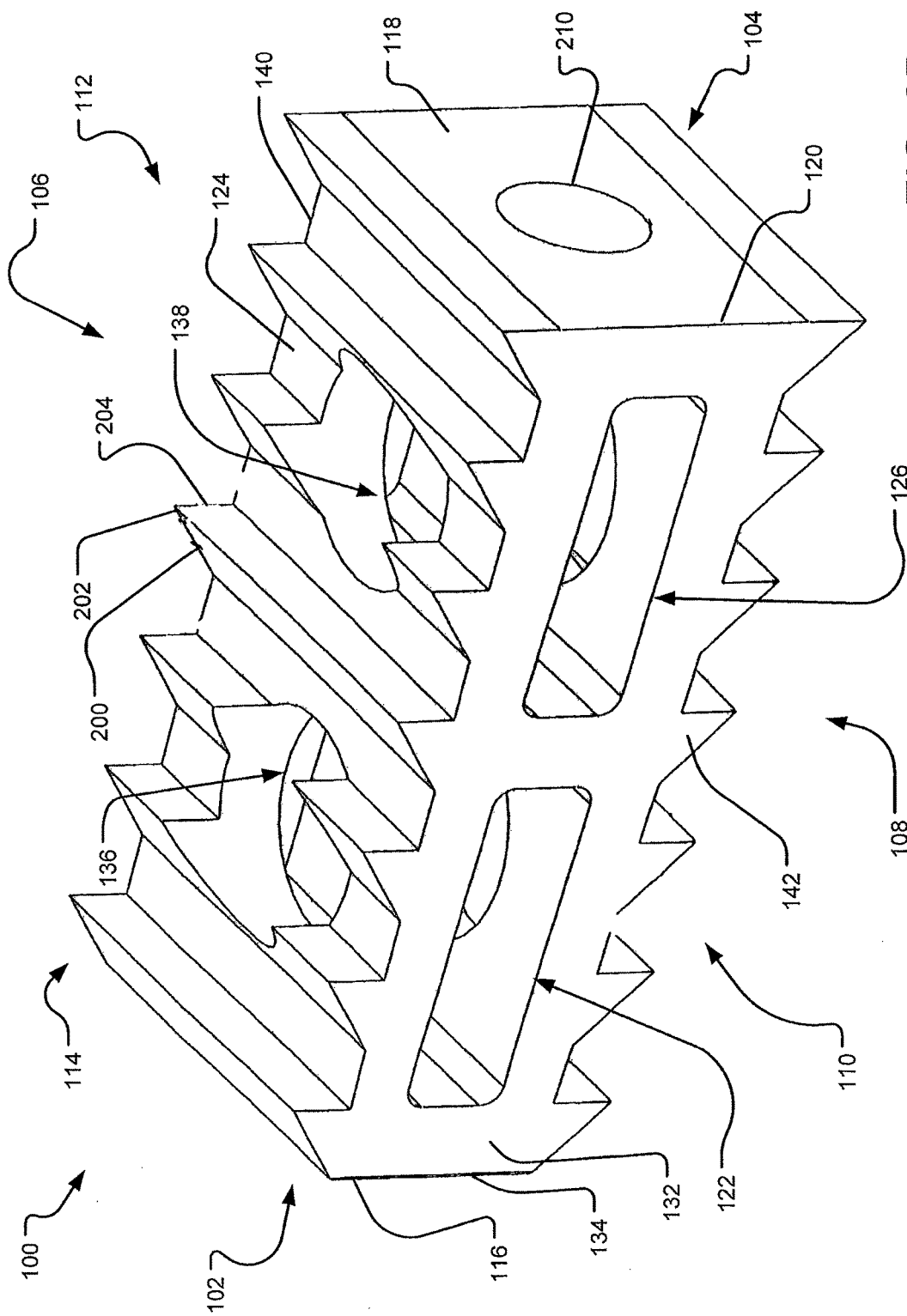
Figure 3A:
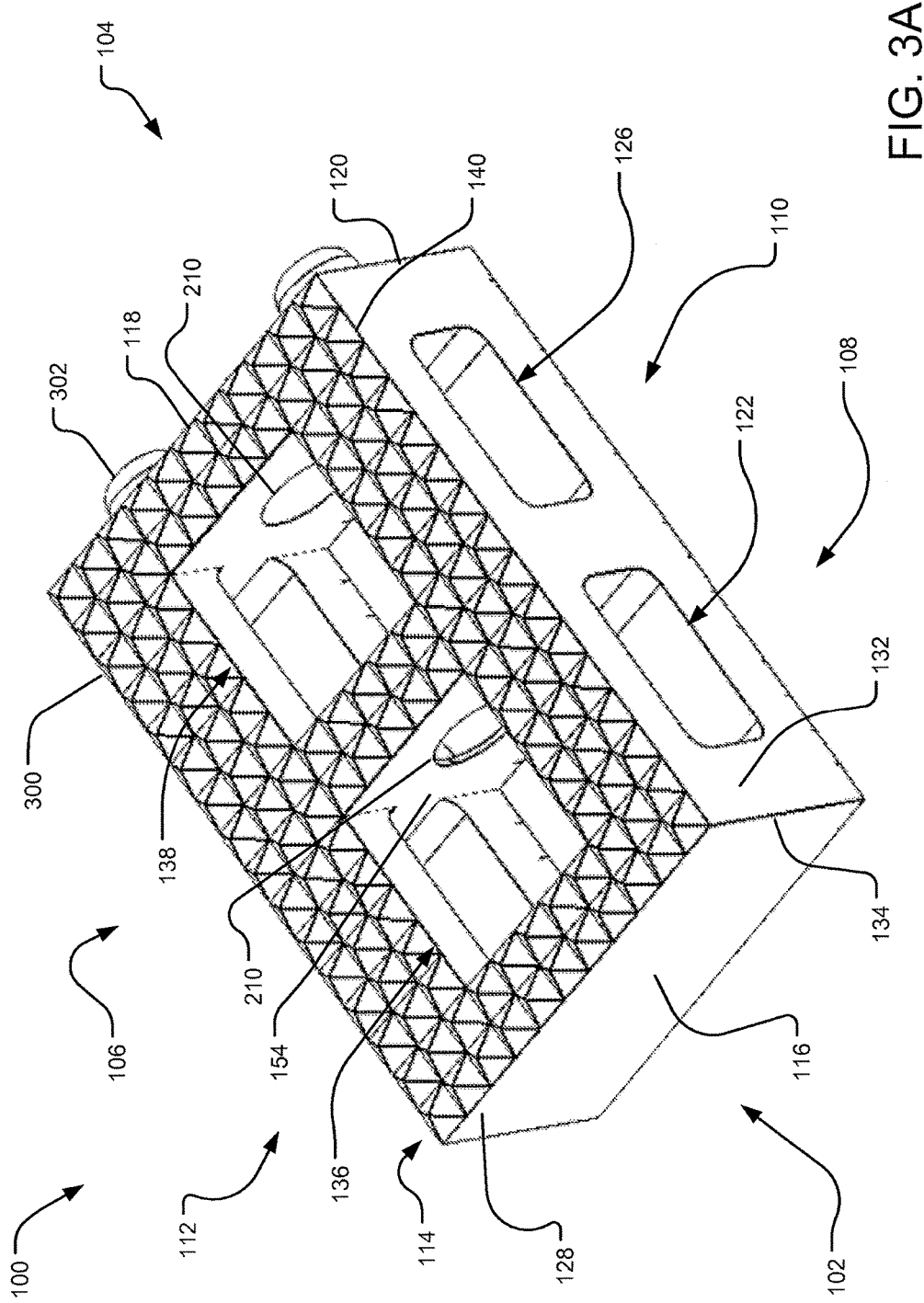
Figure 4A:
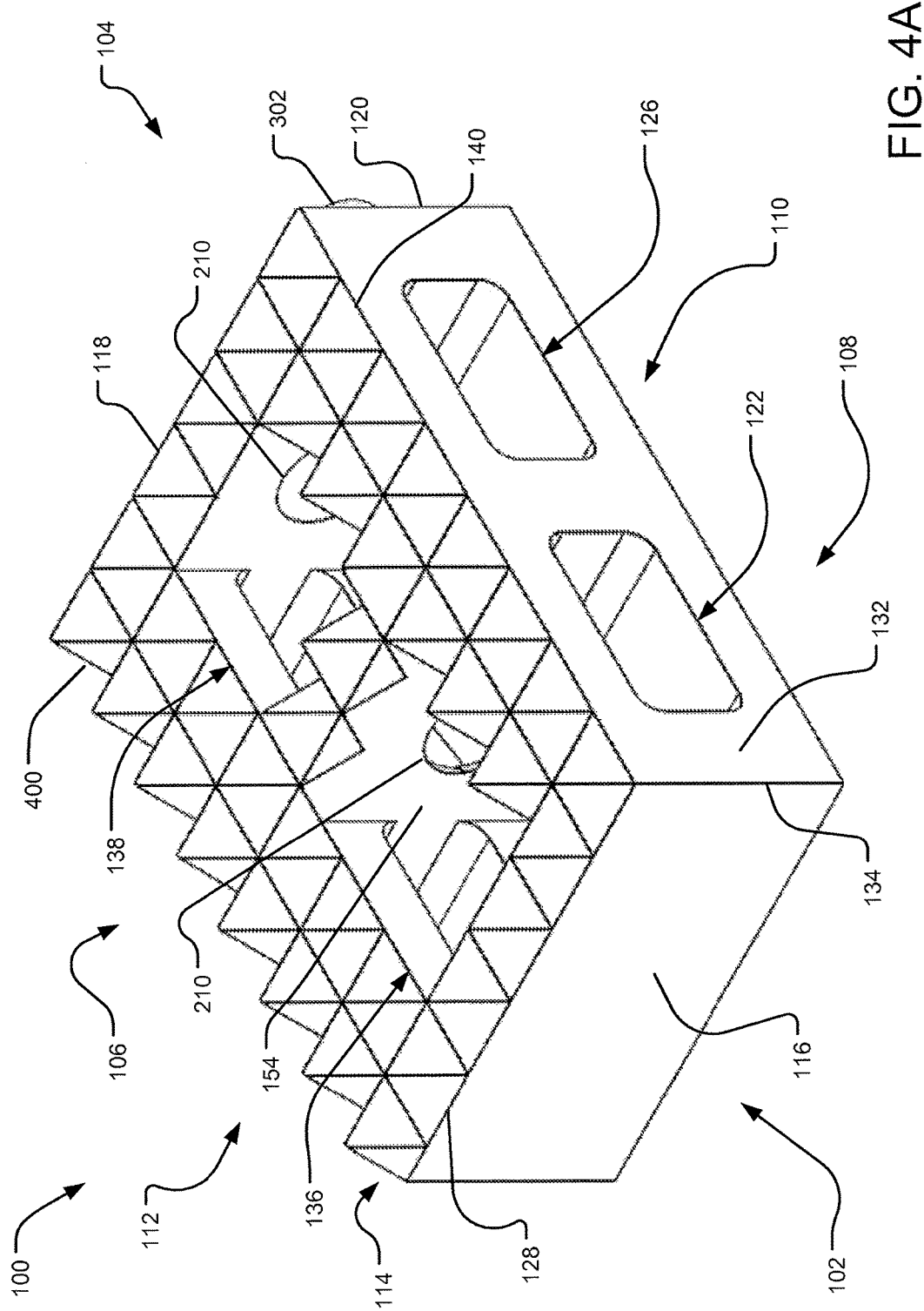
Figure 5A:
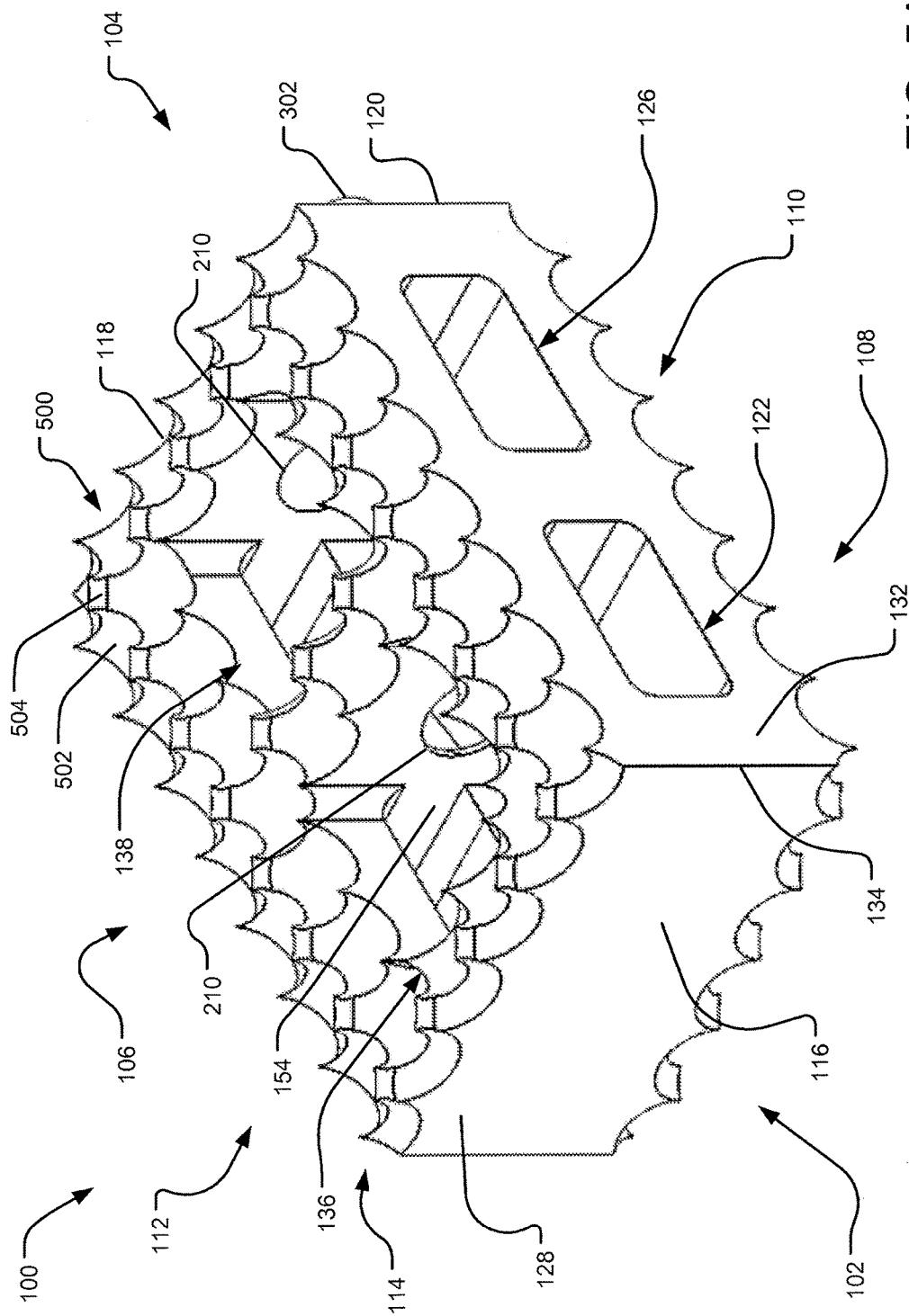
Figure 6A:
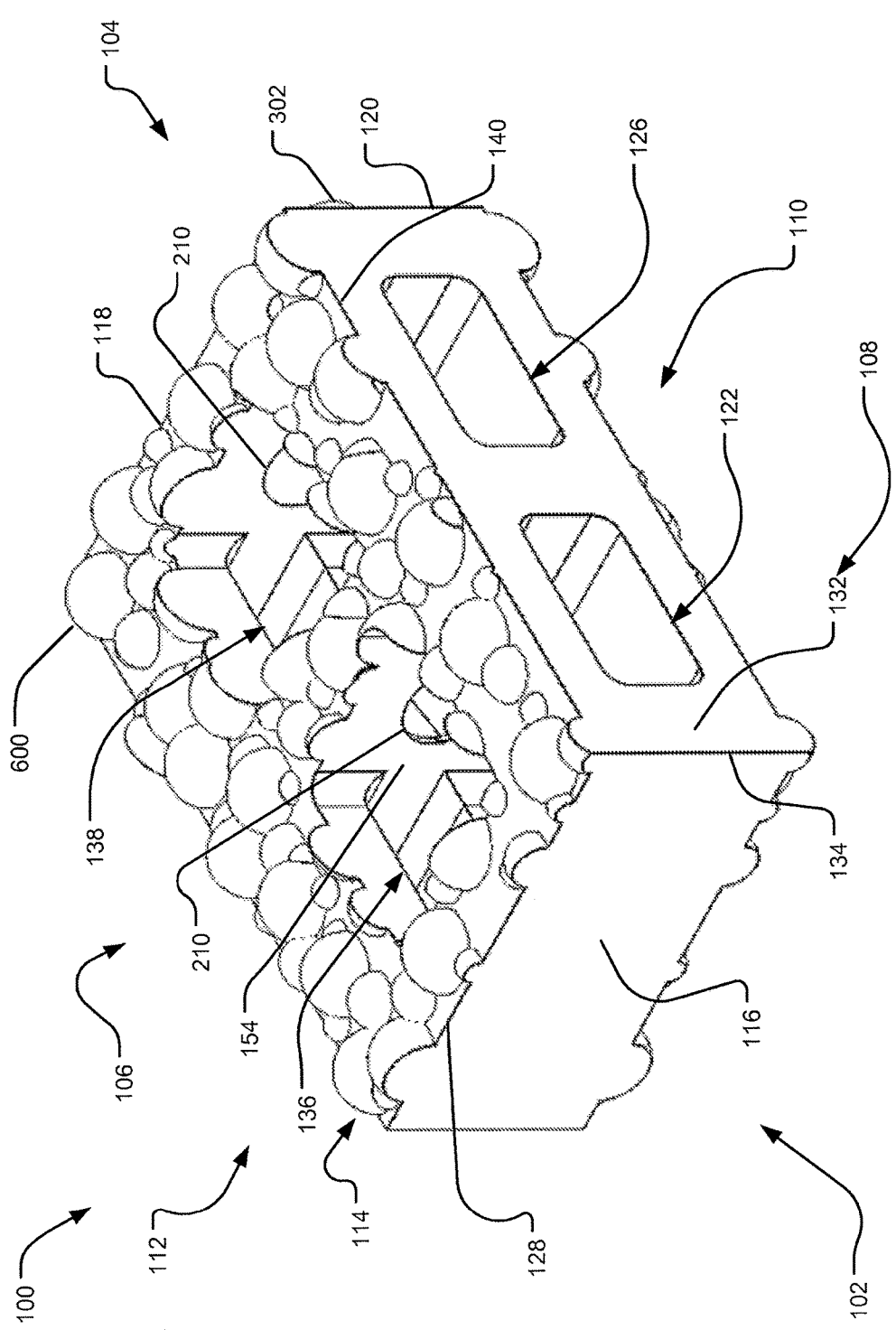
Figures 8B, 8C, 8D:
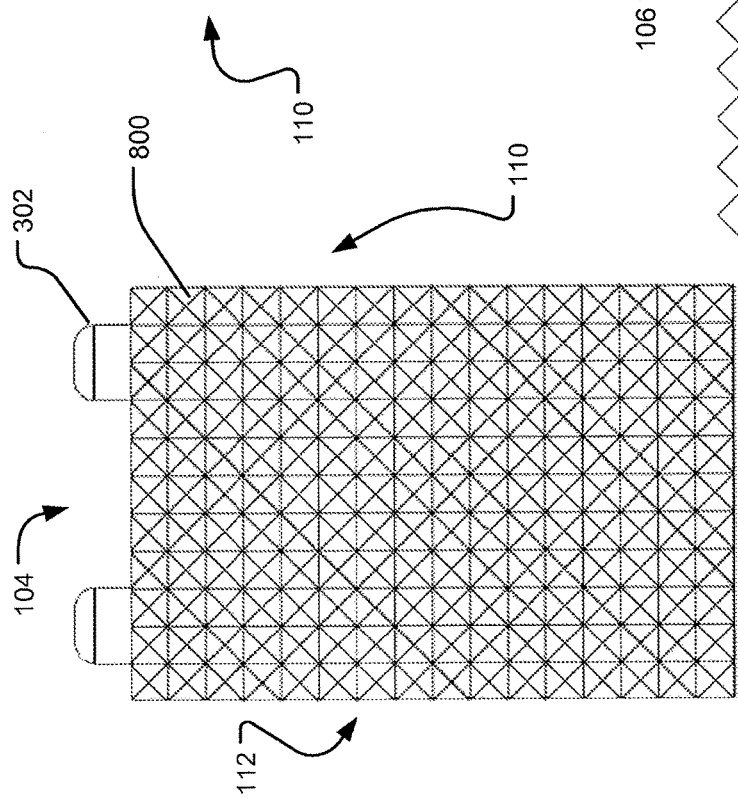

Aspects of the present disclosure generally involve devices and methods for treating spinal stenosis. Spinal stenosis reflects a narrowing of one or more areas of the spine often in the upper or lower back. This narrowing can put pressure on the spinal cord or on the nerves that branch out from the compressed areas. Individual vertebrae of the spine are positioned relative to each other and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

As such, in one aspect, a device for distracting a facet joint of the spine is provided to remedy this condition. The device may include a tool and an implant for distracting and maintaining the distracted position of the joint. The device may be adapted to access a facet joint by inserting a delivery tool and an implant, forcibly separate the associated articular surfaces with the tool, the implant, or both, and leave the implant in place to maintain the separation of the articular surfaces. This approach may allow for maintaining the distraction of the joint, thereby relieving symptoms associated with spinal stenosis.

In one particular aspect, a spinal facet cage implant sized for use as a cervical cage implant for implantation in a spinal facet joint to bring about the fusion of the spinal facet joint is provided. The implant includes at least one face having textured features that provides friction between the spinal facet joint and the implant and one or more windows to place a hollow interior of the implant in communication with the surrounding environment.

For a detailed description of an example spinal facet cage implant 100, reference is made to FIGS. 1A-F, which are front isometric, rear isometric, side, top plan, distal leading end, and proximal trailing end views, respectively.

The implant 100 may be formed of a bone or bone substitute material or a biocompatible metal, ceramic, polymer, or some combination thereof. In one implementation, the implant 100 includes a distal leading end 102 generally opposite a proximal trailing end 104, a first face 106 generally opposite a second face 108, and a first side 110 generally opposite a second side 112. In one implementation, the implant 100 has a general overall shape of a rectangular box with one or more textured features 114.

The first face 106 extends between the distal leading end 102 and the proximal trailing end 104. In one implementation, the first face 106 is generally parallel with the second face 108. For example, the first face 106 may extend from the distal leading end 102 to the proximal trailing end 104 at an angle of approximately 0° to 15° relative to the second face 108. As such, a height of the proximal trailing end 104 may be greater than or equal to a height of the distal leading end 102. In one implementation, the first and second faces 106 and 108 include the textured features 114 that provide friction between the spinal facet joint and the implant 100.

In the implementation shown in FIGS. 1A-F, the distal leading end 102 includes a distal surface 116 and the proximal trailing end 104 includes a proximal surface 118. In one implementation, the distal and proximal surfaces 116 and 118 are planar surfaces forming a generally rectangular shape. The distal surface 116 includes a first pair of distal edges 128 extending between the first and second sides 110 and 112 and a second pair of distal edges 134 extending between the first and second faces 106 and 108. Similarly, the proximal surface 118 includes a first pair of proximal edges 128 and a second pair of proximal edges 120 extending between the first and second faces 106 and 108. In one implementation, where the height of the proximal trailing end 104 is greater than the height of the distal leading end 102, the height of the second pair of proximal edges 120 is greater than the height of the second pair of distal edges 134, such that a surface 124 of the first face 106 and a surface 130 of the second face 108 slope upwardly from the distal leading end 102 to the proximal trailing end 104 along a length 140 extending proximally.

In one implementation, the surface 124 of the first face 106 and the surface 130 of the second face 108 are planar surfaces having a generally rectangular shape formed from the length 140 and a width that is generally coextensive with the first pair of edges 128. The first and second sides 110 and 112 each include a side surface 132 extending between the distal leading end 102 and the proximal trailing end 104. In one implementation, the side surface 132 is a generally planar surface having a pair of opposed edges that are generally coextensive with the second pair of distal edges 134 and the second pair of proximal edges 120.

In one implementation, one or more windows or openings (e.g. a first window 136 and a second window 138) are defined in the surface 124 of the first face 106. The first and second windows 136 and 138 may be opposed or otherwise defined relative to respective windows defined in the surface 130 of the second face 108. Similarly, the first and second sides 110 and 112 may each have one or more windows or openings (e.g., a first side window 122 and a second side window 126) defined in the side surface 132. In one implementation, the windows 122, 126, 136, and 138 each are adapted to place a hollow interior of the implant 100 in communication with the surrounding environment. The windows 122, 126, 136, and 138 may be any shape, size, number, and orientation. For example, in one implementation, the first and second windows 136 and 138 are each generally rectangular and oriented end-to-end, such that each of the windows 136 and 138 extends along approximately half of the length 140 and centered along the edges 128. Similarly, the first and second side windows 122 and 126 are each generally rectangular and oriented end-to-end, such that each of the windows 122 and 126 extends along approximately half of the length 140 and centered along the edges 134 and 120. In one implementation, the first and second windows 136 and 138 are larger in size than the first and second side windows 122 and 126.

The surface 124 of the first face 106 and/or the surface 130 of the second face 108 include the textured features 114. In the implementation shown in FIGS. 1A-F, the textured features 114 are one or more ridges extending generally perpendicularly from the surfaces 124 and/or 130 along the length 140. Each of the ridges includes an inner surface 142 generally opposite an outer surface 144. In one implementation, the outer surface 144 of each of the ridges is generally planar and coextensive with the side surface 132, and the inner surface 142 of each of the ridges is a generally planar surface that is generally perpendicular to the surface 124 of the first face 106 and/or the surface 130 of the second face 108. In one implementation, each of the ridges has a saw toothed profile defined by a plurality of teeth having a leading distal face 148, a trailing proximal face 150, and a tip 146 formed at an intersection between the faces 148 and 150. The trailing proximal face 150 has a slope that is different from a slope of the leading distal face 148. For example, the trailing proximal face 150 has a slope that is greater than the slope of the leading distal face 148. In one implementation, the slope of the trailing proximal face 150 is approximately 90°.

Further, the height of the tips 146 may increase along the length 140, such that teeth positioned near the proximal trailing end 104 have a greater height than teeth positioned near the distal leading end 102. Additionally, a distance between each of the teeth may vary along the length 140. For example, the distance between the teeth positioned near the distal leading end 102 may be less than the distance between the teeth positioned near the proximal trailing end 104. The tip 146 may be a truncated flat surface, a point, or other shapes. Further, it will be appreciated that the first and second faces 106 and 108 may include any number or configuration of ridges or teeth and that the textured features 114 may cover all or a portion of the surface 124 of the first face 106 and/or the surface 130 of the second face 108.

As can be understood from FIGS. 1G-J, in one implementation, the hollow interior of the implant 100 includes one or more chambers 152. For example, the hollow interior may include a chamber 152 separated into a distal chamber and a proximal chamber by an interior wall 154. In this case, the windows 136 and 122 near the distal leading end 102 may be in communication with the distal portion of the chamber 152, and the windows 138 and 126 near the proximal trailing end 104 may be in communication with the proximal portion of the chamber 152. The chambers 152 may, via the windows 122, 126, 136, and 138, be packed with a bone or bone substitute material for causing bone ingrowth into a hollow volume of the chambers 152.

The implant 100 may be a variety of configurations and sizes. In one implementation, the implant 100 has one degree deviation between the first and second faces 106 and 108 and is sized accordingly. For example, a width W1 of the implant 100 extending along the edges 128 between the opposing side surfaces 132 may be approximately 0.217 inches, and a width W2 of the implant 100 extending along the edges 128 between opposing textured features 114 may be approximately 0.177 inches. Additionally, a height H1 from the surface 124 of the first face 106 to the surface 130 of the second face 108 may be approximately 0.118 inches, and a height H2 from a tip 146 of a tooth positioned on the surface 124 to a respective tip 146 positioned on the surface 130 may be approximately 0.187 inches. Further, a length of the teeth LT along the length 140 may be approximately 0.039 inches, and a height HT from a relative surface 124, 130 to the tip 146 may be approximately 0.029 inches. A length LI of the implant 100 extending along the length 140 from the distal leading end 102 to the proximal trailing end 104 may be approximately 0.472 inches. Further, a length LW of the windows 136 and 138 along the length 140 may be approximately 0.177 inches, a width WW of the windows 136 and 138 along the edges 128 may be approximately 0.10 inches, and a distance D of the window 136 from the distal surface 116 may be approximately 0.039 inches. However, it will be appreciated that other sizes an configurations are contemplated where the implant 100 has one degree of deviation between the faces 106, 108.

In another implementation, the implant 100 has three degrees deviation between the first and second faces 106 and 108 and is sized accordingly. For example, a width W1 of the implant 100 extending along the edges 128 between the opposing side surfaces 132 may be approximately 0.217 inches, and a width W2 of the implant 100 extending along the edges 128 between opposing textured features 114 may be approximately 0.177 inches. Additionally, a height H1 from the surface 124 of the first face 106 to the surface 130 of the second face 108 may be approximately 0.103 inches, and a height H2 from a tip 146 of a tooth positioned on the surface 124 to a respective tip 146 positioned on the surface 130 may be approximately 0.187 inches. Further, a length LT of the teeth along the length 140 may be approximately 0.040 inches, and a height HT from a relative surface 124, 130 to the tip 146 may be approximately 0.030 inches. A length LI of the implant 100 extending along the length 140 from the distal leading end 102 to the proximal trailing end 104 may be approximately 0.472 inches. Further, a length LW of the windows 136 and 138 along the length 140 may be approximately 0.177 inches, a width WW of the windows 136 and 138 along the edges 128 may be approximately 0.098 inches, and a distance D of the window 136 from the distal surface 116 may be approximately 0.039 inches. However, it will be appreciated that other sizes an configurations are contemplated where the implant 100 has three degrees of deviation. Further, other deviations between the first and second faces 106 and 108 for the implant 100 may be anywhere between approximately 0° to 15°.

In one implementation, one or both of the first and second faces 106 and 108 may be arcuate as opposed to planar. Stated differently, the surfaces 124 and/or 130 may be arched or planar. For example, a width W1 of the implant 100 extending along the edges 128 between the opposing side surfaces 132 may be approximately 0.217 inches, and a length LI of the implant 100 extending along the length 140 from the distal leading end 102 to the proximal trailing end 104 may be approximately 0.472 inches. Additionally, a height H1 from the surface 124 of the first face 106 to the surface 130 of the second face 108 may be approximately 0.127 inches, and a height H2 from a tip 146 of a tooth positioned in the approximate center of the length 140 (e.g., at a maximum of the arch or bulge) on the surface 124 to a respective tip 146 positioned on the surface 130 may be approximately 0.226 inches. Further, a length LT of the teeth along the length 140 may be approximately 0.039 inches, and a height HT from a relative surface 124, 130 to the tip 146 may be approximately 0.030 inches. Additionally, a length LW of the windows 136 and 138 along the length 140 may be approximately 0.177 inches, a width WW of the windows 136 and 138 along the edges 128 may be approximately 0.098 inches, and a distance D of the window 136 from the distal surface 116 may be approximately 0.039 inches. However, it will be appreciated that other sizes an configurations are contemplated where the implant 100 has arcuate surfaces.

The implant 100 may have a variety of sizes that lend itself to a cervical implant. For example, in one implementation, the implant 100 may have a seven degree deviation between the first and second faces 106 and 108. For example, a width W1 of the implant 100 extending along the edges 128 between the opposing side surfaces 132 may be approximately 0.217 inches, and a length LI of the implant 100 extending along the length 140 from the distal leading end 102 to the proximal trailing end 104 may be approximately 0.472 inches. A height H1 from the surface 124 of the first face 106 to the surface 130 of the second face 108 may be approximately 0.098 inches at the distal leading end 102 and approximately 0.157 inches at the proximal trailing end 104. Further, a length LW of the windows 136 and 138 along the length 140 may be approximately 0.177 inches, a width WW of the windows 136 and 138 along the edges 128 may be approximately 0.098 inches, and a distance D of the window 136 from the distal surface 116 may be approximately 0.039 inches. A length LWS of the windows 122 and 126 along the length 140 may be approximately 0.177 inches, a width WWS of the windows 122 and 126 along the edges 128 may be approximately 0.049 inches, and a distance DS of the window 122 from the distal surface 116 may be approximately 0.039 inches. Further, a height HT of a tip 146 of a tooth positioned on the surface 124 or 130 to may be approximately 0.029 inches, and a height from a tip 146 of a tooth positioned in near the proximal trailing end 104 on the surface 124 to a respective tip 146 positioned on the surface 130 may be approximately 0.216 inches. Additionally, a distance from one tip 146 to a proximally neighboring tip 146 along the length 140 may increase proximally, for example, 0.039 inches to a first tip 146, 0.111 inches to a second, 0.183 inches to a third, 0.255 inches to a fourth, 0.328 inches to a fifth, 0.400 inches to a sixth, and 0.472 inches to a seventh. However, it will be appreciated that other sizes an configurations are contemplated where the implant 100 has seven degrees of deviation. For example, a height from the surface 124 of the first face 106 to the surface 130 of the second face 108 may have a +/−0.15 inch deviation, and a length of the implant 100 extending along the length 140 from the distal leading end 102 to the proximal trailing end 104 may have a +/−0.15 inch deviation.

For additional examples of the implant 100 with various textured features 114 and windows configurations, reference is made to FIGS. 2A-8D. The implants 100 illustrated in FIGS. 2A-8D have features similar to the implant 100 described with respect to FIGS. 1A-J. It will be appreciated that other configurations are contemplated and these illustrations are exemplary and not intended to be limiting.

Turning to FIGS. 2A-D, in one implementation, the surface 124 of the first face 106 and/or the surface 130 of the second face 108 include the textured features 114. In one implementation, the textured features 114 are a plurality of serrated ridges extending across each of the surfaces 124 and 130 generally perpendicularly from the surfaces 124 and/or 130 along the length 140. Each of the ridges includes the outer surface 144, which is generally planar and coextensive with the side surface 132. In one implementation, each of the ridges has a saw toothed profile defined by a plurality of teeth having a leading distal face 200, a trailing proximal face 204, and a tip 202 formed at an intersection between the faces 200 and 204. The trailing proximal face 204 has a slope that is different from a slope of the leading distal face 200. For example, the trailing proximal face 204 has a slope that is greater than the slope of the leading distal face 200. In one implementation, the ridges are substantially evenly spaced.

In contrast to the implementation shown in FIGS. 1A-J, the windows 136 and 138 shown in FIGS. 2A-D are generally circular in shape and are defined in the surface 124 and/or 130 and the ridges. Further, in one implementation, the proximal surface 118 includes a hole 210 defined therein for coupling to a delivery tool (e.g., the tool shown in FIGS. 9-16).

Turning to FIGS. 3A-D, the surface 124 of the first face 106 and/or the surface 130 of the second face 108 include the textured features 114. In one implementation, the textured features 114 are a plurality of protrusions 300 extending generally perpendicularly from the surfaces 124 and/or 130 along the length 140. In the implementation shown in FIGS. 3A-D, the protrusions 300 have a pyramidal shape, including four generally triangular faces and a rectangular base that is generally parallel to the respective surfaces 124 and/or 130. The rectangular base forms generally right angles that are coextensive with angles formed by the width 126 and the length 140 of the respective surfaces 124 and/or 130. Each face of the protrusions 300 is adjacent to two other faces of the same protrusion 300 that extend outwardly from the respective surfaces 124 and/or 130 where they adjoin to form a tip. The protrusions 300 shown in FIGS. 3A-D are relatively small pyramids.

In one implementation, the protrusions 300 are arranged in rows, such that the rectangular base of each of the protrusions 300 abut the bases of adjacent protrusions 300. A plurality of the protrusions 300 extend from the first side 110 to the second side 112 to form the rows, and the rows, in turn, extend from the distal leading end 102 to the proximal trailing end 104 to form a series of rows with the windows 136 and 138 defined therein. Further, it will be appreciated that the first and second faces 106 and 108 may include any number or configuration of the protrusions 300 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and a pair of cylindrical pegs 302 with rounded edges. Further, the interior wall 154 may have the hole 210 defined therein having a centerline that is coextensive with a centerline of the hole 210 defined in the proximal surface 118. In one implementation, the hole 210 is generally centered on the proximal surface 118 and the pegs 302 generally oppose each other on either side of the hole 210.

Turning to FIGS. 4A-D, in one implementation, the surface 124 of the first face 106 and/or the surface 130 of the second face 108 include the textured features 114. In one implementation, the textured features 114 are a plurality of protrusions 400 extending generally perpendicularly from the surfaces 124 and/or 130 along the length 140. In the implementation shown in FIGS. 4A-D, the protrusions 400 have a pyramidal shape, including four generally triangular faces and a rectangular base that is generally parallel to the respective surfaces 124 and/or 130. The rectangular base forms generally right angles that are coextensive with angles formed by the width 126 and the length 140 of the respective surfaces 124 and/or 130. Each face of the protrusions 400 is adjacent to two other faces of the same protrusion 400 that extend outwardly from the respective surfaces 124 and/or 130 where they adjoin to form a tip. The protrusions 400 shown in FIGS. 4A-D are relatively large pyramids.

In one implementation, the protrusions 400 are arranged in rows, such that the rectangular base of each of the protrusions 400 abut the bases of adjacent protrusions 400. There may be a gap between each of the rows to accommodate larger protrusions 400. A plurality of the protrusions 400 extend from the first side 110 to the second side 112 to form the rows, and the rows, in turn, extend from the distal leading end 102 to the proximal trailing end 104 to form a series of rows with the windows 136 and 138 defined therein. Further, it will be appreciated that the first and second faces 106 and 108 may include any number or configuration of the protrusions 400 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and the pair of cylindrical pegs 302 with rounded edges. Further, the interior wall 154 may have the hole 210 defined therein having a centerline that is coextensive with a centerline of the hole 210 defined in the proximal surface 118. In one implementation, the hole 210 is generally centered on the proximal surface 118 and the pegs 302 generally oppose each other on either side of the hole 210.

As can be understood from FIGS. 5A-D, the surface 124 of the first face 106 and/or the surface 130 of the second face 108 include the textured features 114 defined therein. In one implementation, the textured features 114 are a plurality of dimples 500 having a generally spherical imprint or indentation 502 having a radial depth generally perpendicularly into the respective surfaces 124 and/or 130. In one implementation, the dimples 500 are arranged in rows, such that the indentations 502 overlap with at least a portion of an adjacent indentation 502. A plurality of the dimples 500 extend from the first side 110 to the second side 112 to form the rows, and the rows, in turn, extend from the distal leading end 102 to the proximal trailing end 104 to form a series of rows with the windows 136 and 138 defined therein. The effect creates a grid-like pattern of the dimples 500 forming towers 504 between the indentations 502. In one implementation, the towers 504 are generally planar surfaces. The degree of overlap of the indentations 502 and the depth of the indentations 502 can vary accordingly so as to provide an appropriate amount of friction and grip between the implant 100 and the bone surface. Further, it will be appreciated that the first and second faces 106 and 108 may include any number or configuration of the dimples 500 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and the pair of cylindrical pegs 302 with rounded edges. Further, the interior wall 154 may have the hole 210 defined therein having a centerline that is coextensive with a centerline of the hole 210 defined in the proximal surface 118. In one implementation, the hole 210 is generally centered on the proximal surface 118 and the pegs 302 generally oppose each other on either side of the hole 210.

Referring to FIGS. 6A-D, in one implementation, the surface 124 of the first face 106 and/or the surface 130 of the second face 108 include the textured features 114. Further, the side surfaces 124, the distal surface 116, and/or the proximal surface 118 may include the textured features 114. In one implementation, the textured features 114 are a plurality of grit particles 600 extending generally perpendicularly from the surfaces 124 and/or 130 along the length 140 with the windows 136 and 138 defined therein. The grit particles 600 may be a variety of shapes adapted to fuse the implant 100 to the bone surface. In the implementation shown in FIGS. 6A-D, the grit particles 700 have a semi-circular, bubble-like shape.

In one implementation, the grit particles 600 are randomly adhered to the respective surfaces 124 and 130, such that the surfaces 124 and 130 may contain differences in the layout of the textured features 114. The grit particles 600 may be applied by a variety of suitable means to adhere the grit particles 600 to the material of the surfaces 124 and 130. In another implementation, the grit particles 600 are arranged relatively uniformly (i.e., in rows or strips) on the respective surfaces 124 and 130. Further, it will be appreciated that the first and second faces 106 and 108 may include any number or configuration of the grit particles 600 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and the pair of cylindrical pegs 302 with rounded edges. Further, the interior wall 154 may have the hole 210 defined therein having a centerline that is coextensive with a centerline of the hole 210 defined in the proximal surface 118. In one implementation, the hole 210 is generally centered on the proximal surface 118 and the pegs 302 generally oppose each other on either side of the hole 210.

Turning to FIGS. 7A-D, in one implementation, the surface 124 of the first face 106 and/or the surface 130 of the second face 108 include the textured features 114. Further, the side surfaces 124, the distal surface 116, and/or the proximal surface 118 may include the textured features 114. In one implementation, the textured features 114 are a plurality of pits 700 extending generally perpendicularly into the surfaces 124 and/or 130 along the length 140 with the windows 136 and 138 defined therein. The pits 700 may be a variety of shapes adapted to fuse the implant to the bone surface. For example, the pits 700 may be shaped like a negative imprint of the grit particles 600, the dimples 500, the protrusions 400 or 300 or any similar feature. In the implementation shown in FIGS. 7A-D, for example, the pits 700 are negative imprints of a semi-circular, bubble-like shape. The depth of such an imprint and the imprint diameter will vary accordingly to achieve adequate friction between the implant and the bone.

The surfaces 124 and 130 may undergo a reductive surface treatment, including, without limitation, abrasive blasting, chemical treating, and the like, to achieve the pits 700. In addition to a reductive surface treatment, an additive treatment may be used to texture the surfaces 124 and 130 to add a pre-textured layer. In one implementation, the pits 800 cover the respective surfaces 124 and 130 in a random orientation, such that the surfaces 124 and 130 may contain differences in the layout of the textured features 114. In another implementation, the pits 700 are arranged relatively uniformly (i.e., in rows or strips) on the respective surfaces 124 and 130. Further, it will be appreciated that the first and second faces 106 and 108 may include any number or configuration of the pits 700 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and the pair of cylindrical pegs 302 with rounded edges. Further, the interior wall 154 may have the hole 210 defined therein having a centerline that is coextensive with a centerline of the hole 210 defined in the proximal surface 118. In one implementation, the hole 210 is generally centered on the proximal surface 118 and the pegs 302 generally oppose each other on either side of the hole 210.

Turning to FIGS. 8A-D, in one implementation, the surface 124 of the first face 106 and/or the surface 130 of the second face 108 include the textured features 114. In one implementation, the textured features 114 are a plurality of protrusions 800 extending generally perpendicularly from the surfaces 124 and/or 130 along the length 140. In the implementation shown in FIGS. 8A-D, the protrusions 800 have a pyramidal shape, including four generally triangular faces and a rectangular base that is generally parallel to the respective surfaces 124 and/or 130. The rectangular base forms generally right angles that are coextensive with angles formed by the width 126 and the length 140 of the respective surfaces 124 and/or 130. Each face of the protrusions 800 is adjacent to two other faces of the same protrusion 800 that extend outwardly from the respective surfaces 124 and/or 130 where they adjoin to form a tip. The protrusions 800 shown in FIGS. 8A-D are relatively small pyramids.

In one implementation, the protrusions 800 are arranged in rows, such that the rectangular base of each of the protrusions 800 abut the bases of adjacent protrusions 800. There may be a gap between each of the rows to accommodate larger protrusions 800. A plurality of the protrusions 800 extend from the first side 110 to the second side 112 to form the rows, and the rows, in turn, extend from the distal leading end 102 to the proximal trailing end 104 to form a series of rows covering the surfaces 124 and 130. Further, it will be appreciated that the first and second faces 106 and 108 may include any number or configuration of the protrusions 800 and that the textured features 114 may cover all or a portion of the surface 124 of the first face 106 and/or the surface 130 of the second face 108.

In one implementation, the proximal surface 118 includes a hole 210 defined therein for coupling to a delivery tool (e.g., the tool shown in FIGS. 9-16) and the pair of cylindrical pegs 302 with rounded edges. The hole 210 may be generally centered on the proximal surface 118 and the pegs 302 generally oppose each other on either side of the hole 210. In one implementation, the implant 100 does not includes the windows 122, 126, 136, and/or 138.

As can be understood from FIGS. 9-16, a distraction system 900 is configured to minimally invasively or percutaneously deliver implementations of the implant 100 into a patient spinal facet joint space via, for example, a posterior approach. In one implementation, the system 900 includes a delivery tool 902 and a guide tube 904, both of which extend from a respective leading distal end 906, 907 to a respective trailing proximal end 908, 909. As can be understood from FIG. 9, the delivery tool 902 can be received in the lumen of the guide tube 904 to bring about the delivery of the implant 100 into the target spinal facet joint. The system 900 may further include a decorticator 936, an injector 948, a chisel 960, a place holding chisel 974, and a malleting tool 980.

Figure 9:
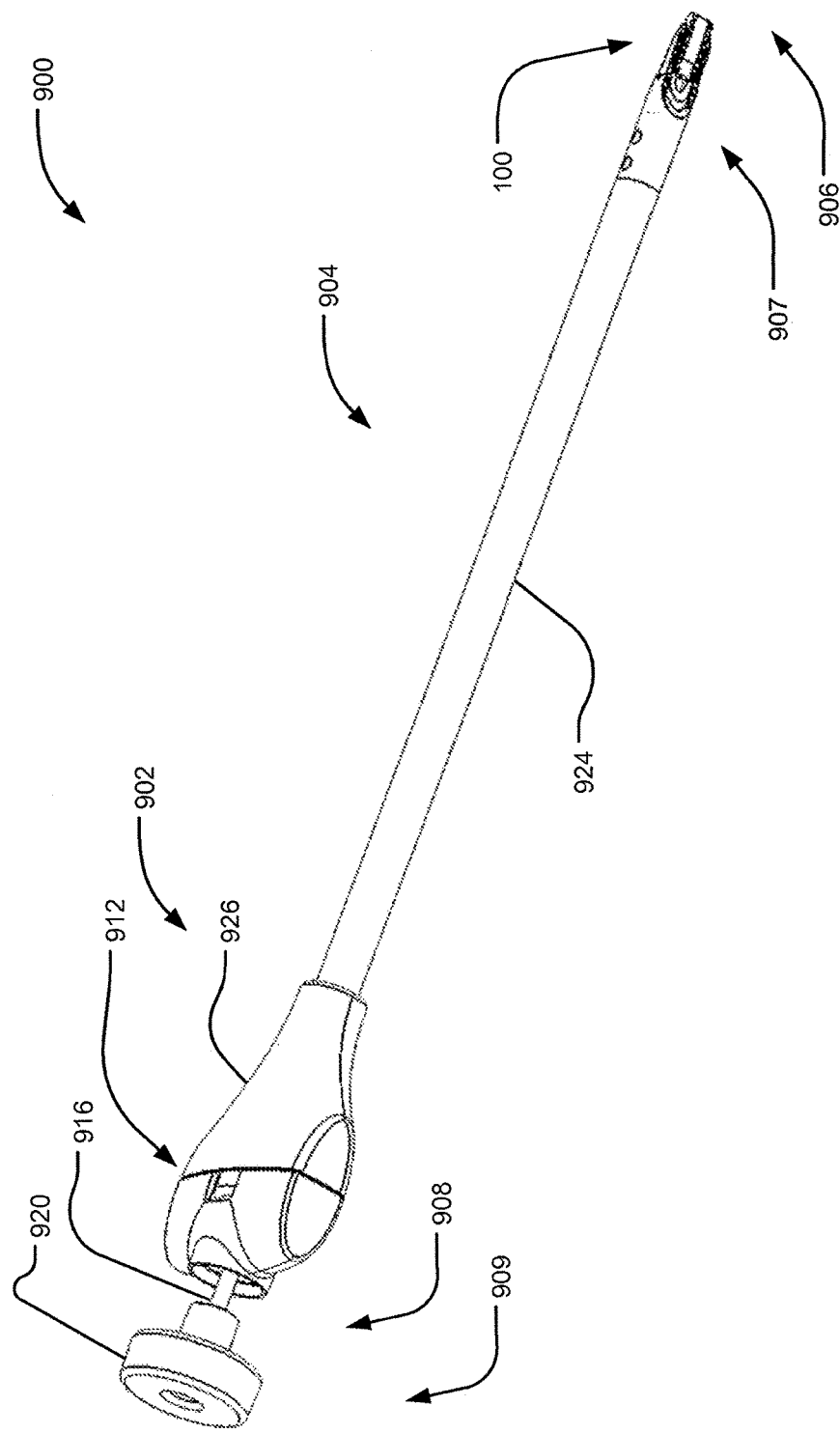
FIG. 9 shows an example delivery device and guide tube configured to minimally invasively deliver a spinal facet cage implant.
Figure 10:
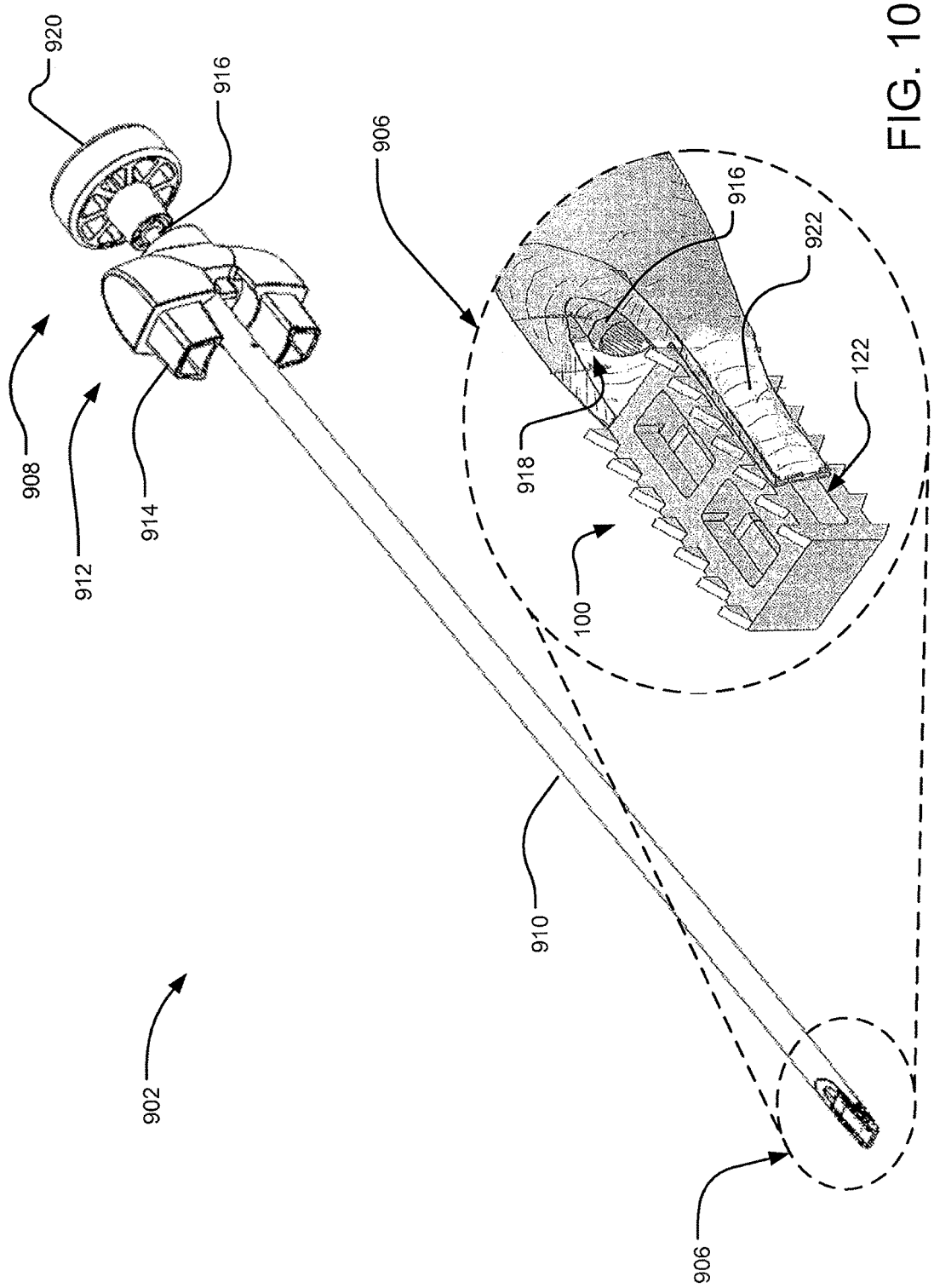
FIG. 10 shows a perspective view the delivery device of FIG. 9 and a detailed view of a distal end of the delivery device.

For a detailed description of the delivery tool 902, reference is made to FIG. 10. In one implementation, the delivery tool 902 includes a tubular body 910 with a handle arrangement 912 at the trailing proximal end 908. The handle arrangement 912 may further include one or more members 914 for engaging the guide tube 904 as depicted in FIG. 9. In one implementation, a plunger or threaded member 916 extends through a lumen 918 of the tubular body 910 and includes a handle 920 at the trailing proximal end 906. In the case of the plunger embodiment, the plunger may be used to distally push the implant from an interference fit engagement with the arms 922 of the delivery tool distal end 906. In the case of the threaded member embodiment, the threaded member 916 threadably engages the implant 100 to retain the implant 100 in an attached manner to the delivery tool distal end 906 until time to release the implant 100 into the target facet joint space.

In one implementation, the tubular body 910 at the leading distal end 906 includes opposed prongs 922 between which the implant 100 may be supported until the plunger 916 can be used to eject the implant 100, or, in the case of a threaded member, until the threaded member 916 can be threadably uncoupled from the implant 100. The prongs 922 include longitudinally extending ridges that are adapted to interact with the sides 110 and 112 of the implant 100 or structural features of the implant 100 (e.g., the windows 122 and/or 126). In one implementation, the plunger 916 is spring biased to keep the plunger 916 proximally displaced in the lumen 918 of the tubular body 910, such that distal force exerted against the handle 920 causes the plunger 216 to distally displace to eject the implant from the tubular body 910 at the leading distal end 906. In one embodiment where there is the threaded engagement, the threaded member 916 is rotationally displaceable within and relative to the delivery tool shaft 910.

As discussed herein, in some implementations, the proximal trailing end 104 of the implant 100 includes a structural feature (e.g., the threaded hole 210) that may be engaged by a retainer member (e.g., a threaded rod 916) extending through the lumen 918 of the tubular body 910 to retain the implant 100 at the distal end 906 of the tubular body 910 until the retainer member can be disengaged to allow the implant 100 to be left behind in the facet joint upon the tubular body 910 being withdrawn from the percutaneous access site.

Turning to FIG. 11A, a detailed description of the guide tube or tool 904 is provided. In one implementation, the guide tube 904 includes a receiving assembly 926 at a proximal end 909 and a pair of anchoring forks 934 at a distal end 907 with a generally tubular shaft 924 extending there between. The anchoring forks 934 may be textured distal parallel prongs for accessing a spinal facet joint and through which the delivery tool 902 can be routed to deliver the implant 100 in the facet joint. As illustrated in FIG. 11A, in one embodiment, the two parallel prongs 934 may have the same height and configuration, differing only in that they are mirror images of each other. In another embodiment, the two parallel prongs 934 may differ in height relative to each other, thereby distracting the facet joint at different heights at each prong interface with the facet joint. For example, as illustrated in FIG. 11B, which is an enlarged longitudinal side view of an alternative embodiment of the distal end of the guide tube having dual-sized parallel prongs, the two parallel prongs may have heights HP1 and HP2 of 0.106 inches and 0.164 inches. However, other dimensions of the guide tube 904 are contemplated.

The guide tube 904 can also include a malleting anvil 930 having a raised surface 932 positioned on the proximal face of the receiving assembly 926 adapted for contact with a distal end of a malleting head 966 on the chisel 960 or on the delivery tool 902. Malleting on the proximal end of the chisel 960 or the delivery tool 902 can cause longitudinal forces along the length of the respective tool piece. These longitudinal forces can be transferred, at least partially, through the contact between the malleting head and the malleting anvil 930. Accordingly, relative motion between the respective tool piece and the guide tube 904 can be prevented. As such, for example, at the distal end 907 of the guide tube 904, the relative position of the distal end 972 of the chisel 960 or the delivery tool 902 relative to the distal end 907 of the guide tube 904 can be maintained. Further, in one implementation, the receiving assembly 926 includes a receiving portion 928 for receiving and engaging the members 914 or 970 of the delivery tool 902 and the chisel 960, respectively, as depicted in FIG. 9.

Figure 12:
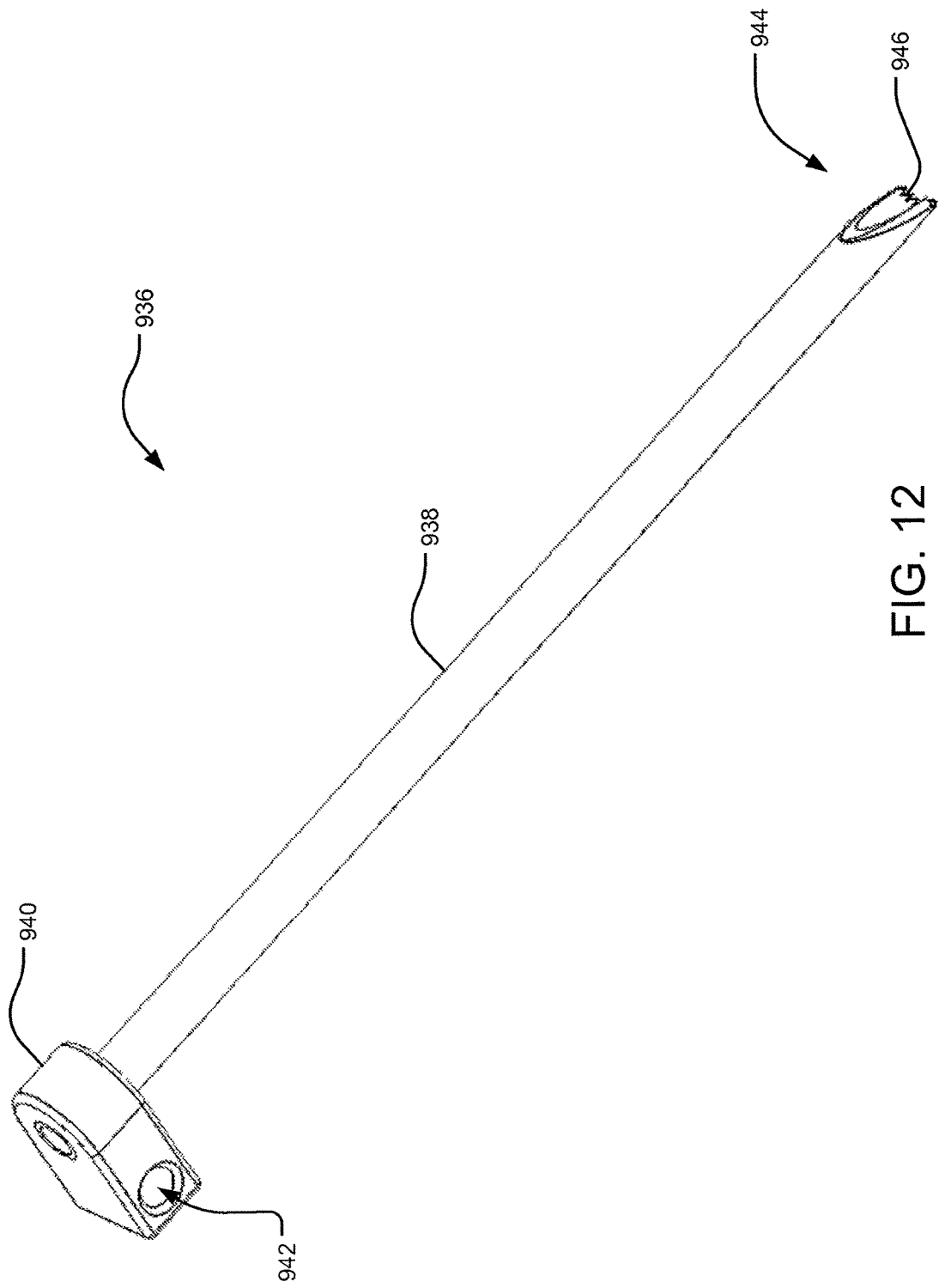
FIG. 12 depicts a perspective view of an example decorticator.

As can be understood from FIG. 12, in one implementation, the decorticator 936 includes a tubular shaft portion 938, an abrasive distal end 944, and a handle 940 at a proximal end. The tubular shaft 938 may have an inner radius substantially equal to an outer radius of the shaft 976 of the place holding or guide chisel 974 of FIG. 15 and may allow for sliding movement of the decorticator 936 along the length of the chisel shaft 976 and rotationally around the chisel shaft 976. In some implementations, the inner radius of the tubular shaft 938 may be slightly or substantially larger than the outer radius of the shaft 976 of the chisel 974 allowing for more freedom of movement of the decorticator 936.

The abrasive distal end 944 of the decorticator 936 may include serrated teeth 946 as shown, or may include a more flat annular surface with a gritty surface. In the implementation shown in FIG. 12, the distal end of the tubular shaft portion 938 is chamfered and the serrated teeth 946 are located on the distal most end of the chamfered end allowing for a more directed and controllable decorticating process. As such, the decorticator 936 shown is well suited for the intra facet process reflected by many of the implementations described herein. That is, the human anatomy of the cervical spine may be such that the lateral mass of the facet joints are not perpendicular to the surface of the facet joint.

Additionally, to properly place the prongs 934 of the place holding or guide chisel 974 within the joint, the guide chisel 974 may be positioned substantially parallel to articular surfaces of the facet joint. As such, the place holding or guide chisel 974 may not be positioned perpendicular to the lateral masses of the facet joints and may actually be directed with a downward slope as it extends in the distal direction. Where the decorticator 936 has a non-chamfered annular end, depending on anatomy, the decorticator 936 may be able to be placed in contact with the superior lateral mass, but may be unable to reach or contact the inferior lateral mass. In the present implementation, the chamfered end of the tubular shaft portion 938 will allow the distal tip of the chamfered end to reach and decorticate the inferior lateral mass. This chamfered distal end may define an angle to the longitudinal axis. Additionally, the teeth 946 may be relatively large or they may relatively small and may extend along the full perimeter surface of the chamfered end rather being positioned solely at the tip of the chamfered end. Additionally, a beveled edge may run along the periphery of the chamfered end. That is, along the ovular shape created by the chamfered tubular shaft portion 938, the edge is beveled. As such, when the guide chisel 974 is inserted into the patient and/or when the decorticator 936 is advanced along the chisel 974, the beveled edge may assist in avoiding tissue snags, and the decorticator 936 may be placed in contact with the lateral mass of the facet joints in a much smoother process and may avoid damage to neighboring tissues.

The handle 940 of the decorticator 936 may include a gripping surface along its peripheral edge and may sleevably receive the tubular shaft portion 938. The handle 940 may also include radially extending bores 942 adapted to receive a gripping tool to provide for better control and a higher amount of torsional leverage when decorticating the lateral masses of the facet joint or to allow for malleting in the longitudinal direction of the decorticator 936 to cause forceful decortication of the lateral mass. The decorticator 936 may then be retracted, rotated to a new radial position, advanced, and struck again for additional decortication.

Figure 13:
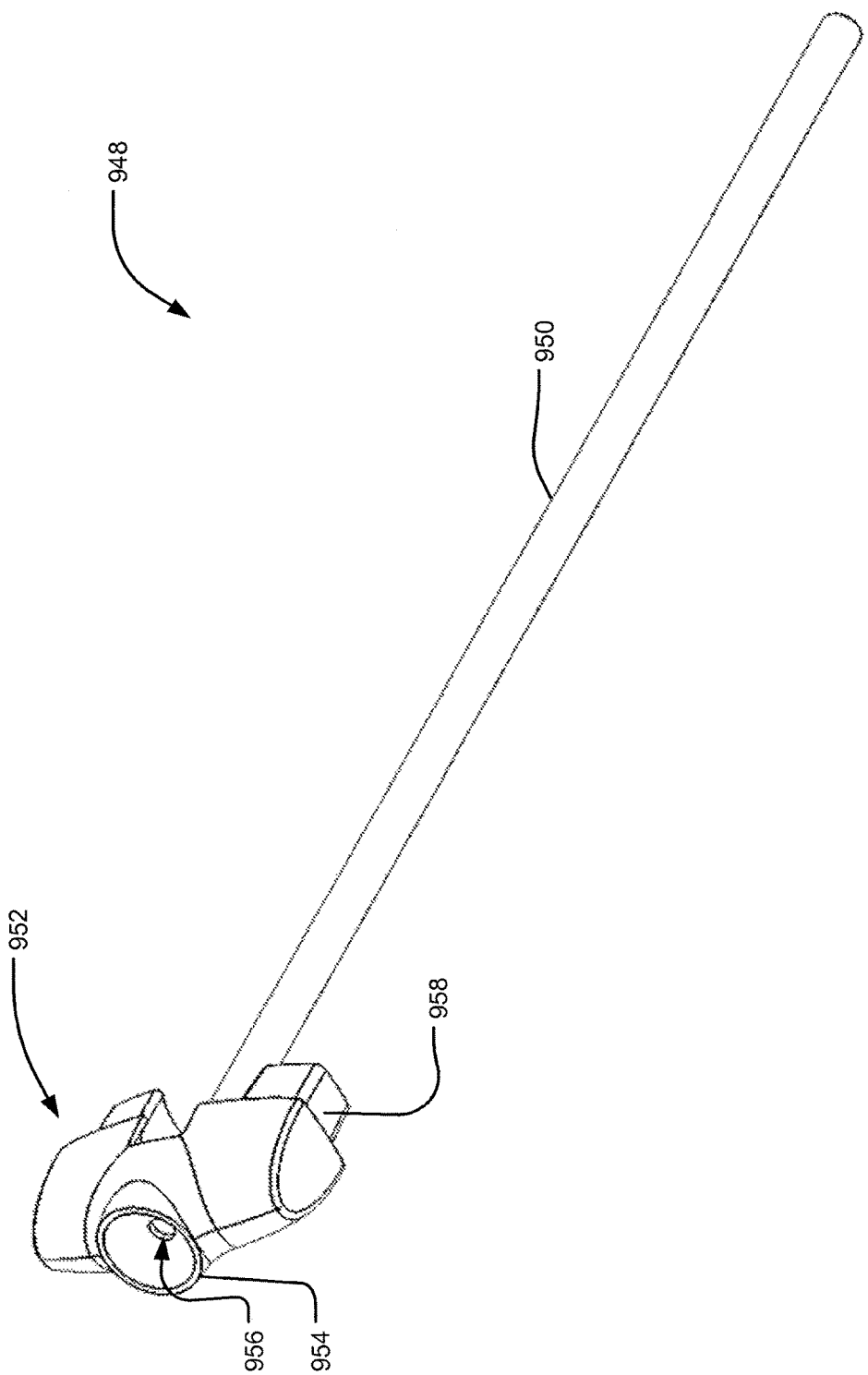
FIG. 13 shows a perspective view of an example injector.

Referring to FIG. 13, in one implementation, the injector 948 includes a longitudinal delivery shaft 950 and a seating feature 952. The longitudinal delivery shaft 950 may have any cross-section and may have a cross-sectional size adapted to fit within the guide tube 904. The longitudinal shaft 950 may have an opening 956 on its distal end 954 for directing bone paste out the distal end of the shaft 950 allowing the paste to flow into and/or over the facet joint and/or outward toward the lateral mass of a facet joint. The seating feature 952 may include a member 958 positioned around the shaft 950, which may be sized and shaped to abut the receiving portion 928 of the guide tube 904. The injector 948 may be sleevably inserted into the guide tube 904 and advanced such that the distal end of the shaft 950 is positioned between the prongs 934.

Figure 14:
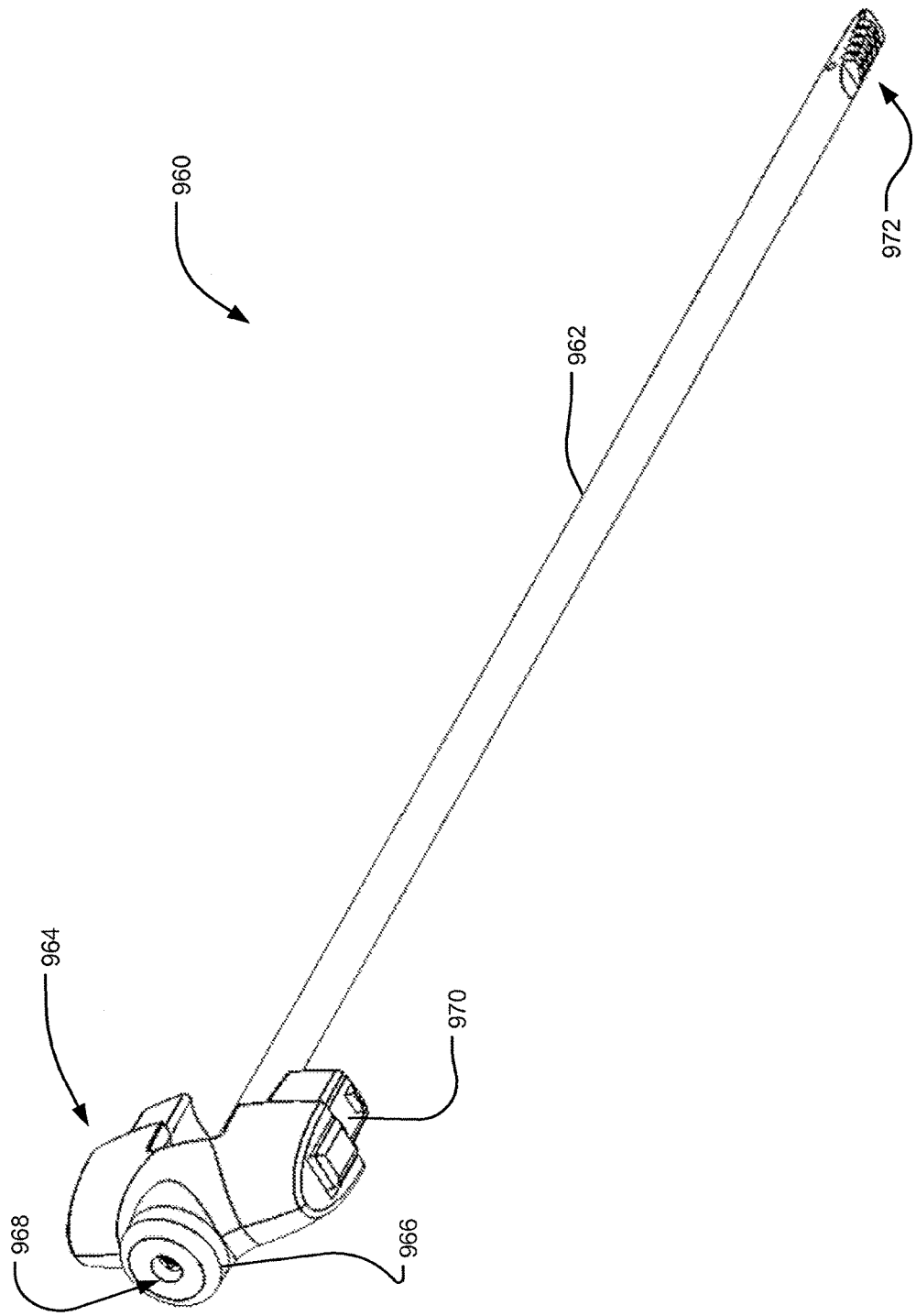
FIG. 14 is a perspective view of an example chisel.

As can be understood from FIG. 14, in one implementation, the chisel 960 includes a generally cylindrical cross-section forming a shaft 962, which may have a radius substantially equal to the inner radius of the tubular shaft portion 924 of the guide tube 904 allowing for slidable insertion of the chisel 960 within the guide tube 904. Alternatively, the radius of the shaft 963 may be smaller than the inner radius of the tubular shaft 924 providing for more play and adjustability of the chisel 960 and the guide tube 904 relative to one another. The chisel 960 may include a single or doubly chamfered tip 972 at a distal end or may have a coped distal end or a combination of coping and chamfering. The tip 972 may include a roughened surface on one or more sides to aid in anchoring or docking the chisel in the facet joint. Additionally, this roughened surface may allow for roughening or decorticating the inner surfaces of the facet joint. The tip 972 may have a length adapted to extend substantially across the facet joint.

The chisel 960 may further include a handle assembly 964 may include a member 970 positioned around the shaft 962, which may be sized and shaped to abut the receiving portion 928 of the guide tube 904. The chisel 1008 may also include a longitudinally extending lumen 968 and a malleting head 966.

Figure 15:
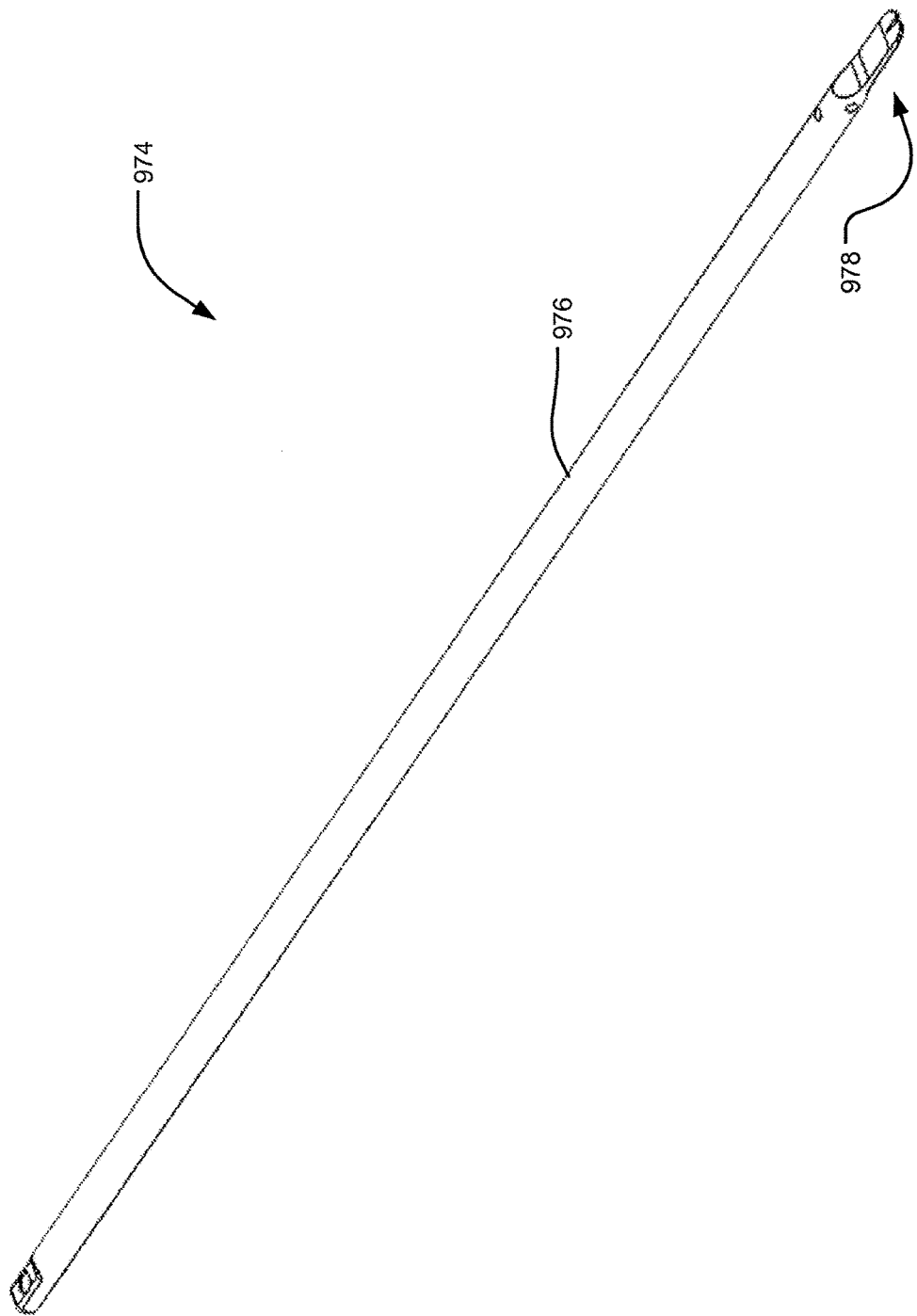
FIG. 15 illustrates an example place holding chisel.

Turning to FIG. 15, in one implementation, the placing holding or guide chisel 974 includes a shaft 976 and a distal tip 978, which may include a tip the same or similar to the chisel 960. For example, the chisel 974 can include a coped and/or chamfered tip. Additionally, the chisel 974 can include ridges. Additionally, the chisel 974 can include a radiopaque portion on the shaft 976 adapted to allow recognition of the location of the chisel 974 while avoiding occlusion of the lateral view. The radiopaque portion can include a straight, round, square, or other shaped piece of material positioned near the distal end of the chisel 974 for locating the distal end. As also shown, the proximal end of the chisel 974 can include a hole extending transversely there through. The hole can adapted to receive a transverse rod or shaft extending into the hole and/or through the hole. The rod or shaft and the chisel 974 can form a T-grip or L-shaped grip for use in pulling on the chisel 974 for removal.

In one implementation, the place holding chisel 974 can be used as a place holder without occluding the lateral view of a chisel and delivery tool positioned in a contralateral facet joint. That is, upon placement of the chisel 960 and the guide tool 904 in a first facet joint, the chisel 960 may be removed and replaced with the place holding chisel 974 where the prongs 934 of the guide tube 904 maintain the position of the system 900. The guide tube 904 may also be removed and reassembled with the chisel 960 once the place holding chisel 974 is properly positioned. The guide tube 904 and chisel 960 may then be inserted into the contralateral facet joint or second joint. By replacing the chisel 960 in the first joint with the place holding chisel 974, the location of the chisel 960 and guide tube 904 in the second joint may be more readily ascertainable using lateral fluoroscopy. That is, if a radiopaque chisel or delivery device was left in place in the first joint, the fluoroscopic view of the contralateral facet joint would be relatively occluded. Upon placing the guide tube 904 properly in the second facet joint, the procedure above may continue. Upon completing treatment of the second facet joint, the guide tube 904 may be sleeved over the place holding chisel 974 still positioned in and holding the place in the first facet joint and the first facet joint may then be treated with the above procedure. It is noted that initial placement of the guide tube 904 can be conducted with the place holding chisel 974 rather than the chisel 960 to avoid having to replace the chisel 960.

Figure 16:
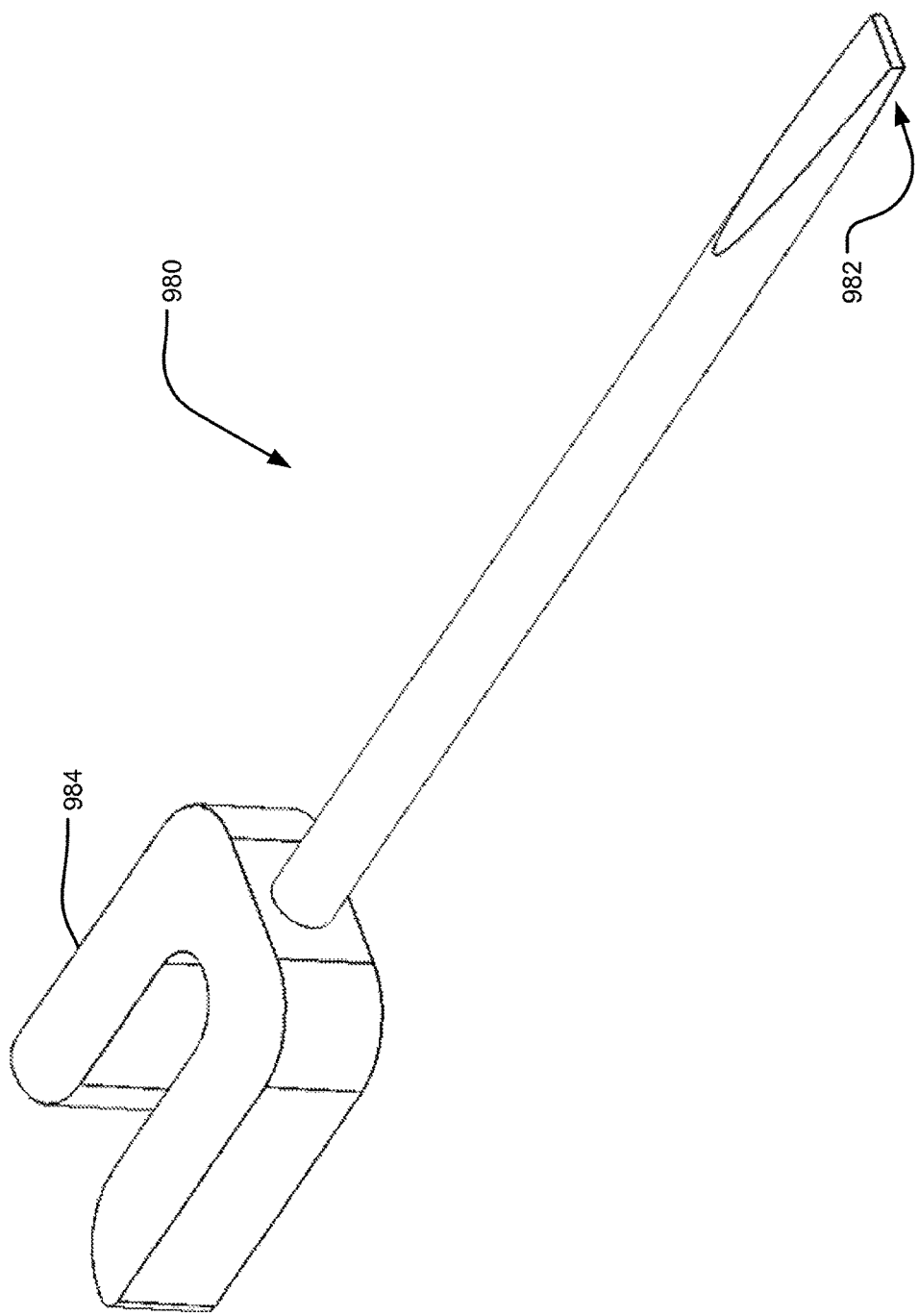
FIG. 16 depicts a perspective view of an example malleting tool.

Referring to FIG. 16, in one implementation, the malleting tool 980 can include a longitudinally shaped shaft with a U-shaped decorticator interface 984 at one end and a chamfered tip 982 at the other end. The decorticator interface 984 can be adapted for positioning around the guide tube 904 in a position just proximal to a malleting element of the decorticator 936. The u-shape of the decorticator interface 984 may allow the malleting tool 980 to be placed in position from the side of the guide tube 904 and selectively used as required to forcibly advance the decorticator 936.

The chamfered end of the tool 982 can be held in position while the user mallets near the decorticator interface end causing the interface 984 to contact the malleting element on the decorticator 936. The decorticator 936 may then be retracted, rotated to a new radial position, advanced, and struck again for additional decortication. The malleting tool 980 may rotate with the decorticator 936 or it may remain in a position convenient for malleting. In addition to malleting, the malleting tool 980 can be used to assist in separating several tools. That is, in some cases, the handles of a given tool piece can be difficult to separate from receiving portion.

The chamfered tip 982 can be used to wedge between a given handle and the receiving portion to assist in separating the devices.

Other implementations of a distraction system 900 can be configured with alternative retaining and deployment (release or eject) methods, such as screw drives, latches, snaps, cams, adhesives, magnets, or the like.

The delivery system components depicted in FIGS. 9-16 can be used to minimally invasively implant any of the implants 100 depicted in FIGS. 1A-8D in a spinal facet joint that is the target of treatment. For example, in one embodiment, a percutaneous or minimally invasive incision is made in the posterior region of the neck to lead to the target facet joint. The access chisel 974 depicted in FIG. 15 is routed through incision under fluoroscopic guidance until the tapered distal tip 978 resides in the target facet joint and the chisel shaft 976 extends out of the patient via the incision. With the access chisel 974 so positioned, the outer decorticator 936 of FIG. 12 can be grasped and distally routed over the access chisel 974 such that the chisel shaft 976 is received in the lumen that extends longitudinally through the outer decorticator 936. With the distal decorticating end 946 of the outer decorticator 936 abutting against one or more lateral masses adjacent the target facet joint, the outer decorticator 936 can be rotated about the chisel shaft 976 to decorticate the bone surfaces of the lateral masses adjacent the target facet joint. Once decortication of the lateral masses has been sufficiently achieved, the decorticator 936 can be removed from about the chisel shaft 976 and from the patient.

Figure 11:
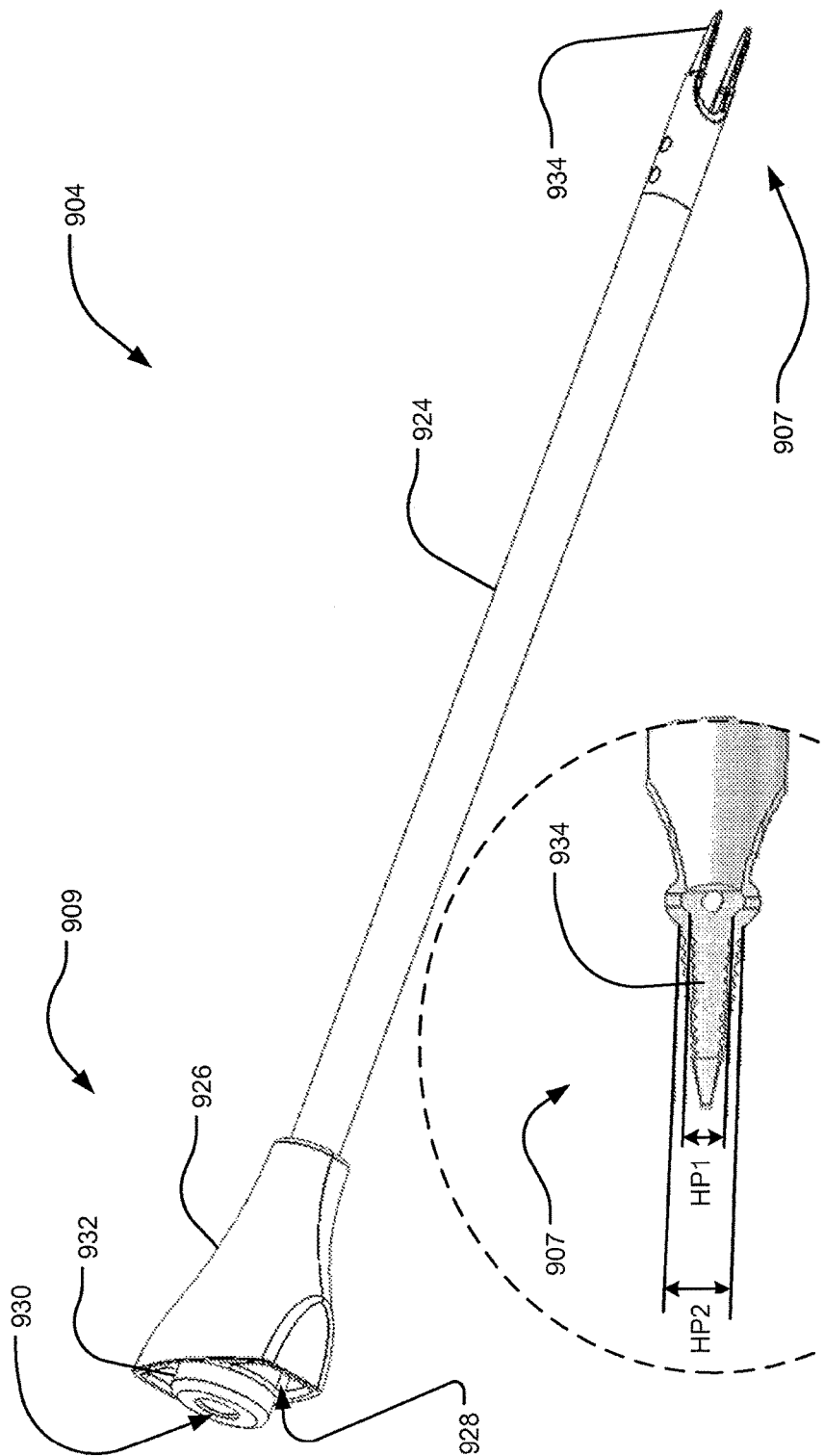
FIG. 11A illustrates a perspective view of the guide tube of FIG. 9, wherein the distal end of the guide tube has same-sized parallel prongs.
FIG. 11B is an enlarged longitudinal side view of an alternative embodiment of the distal end of the guide tube having dual-sized parallel prongs.

With the place holding or access chisel 974 so positioned, the guide tool 904 of FIG. 11 is grasped and distally routed over the chisel 974 such that the chisel shaft 976 is received in the guide tool lumen that extends longitudinally through the guide tool shaft 924. The tapered forked distal end 907 of the guide tool 904 is distally advanced through the incision and along the chisel shaft 976 until the tapered forks 934 of the guide tool 904 are positioned inside the target facet joint, the chisel tapered distal tip 978 being located between the pair of forks 934 of the guide tool distal end 907, the guide tool shaft 924 extending out of the patient via the incision.

With the guide tool 904 so positioned, the place holding or access chisel 974 can be withdrawn out of the guide tool lumen and out of the patient, leaving the guide tool tapered forked distal end 907 residing in the target facet joint and the guide tool shaft extending out of the patient. The decorticating chisel 960 of FIG. 14 can then be distally routed through the lumen of the guide tool 904 to place the tapered decorticating distal end 972 of the chisel 960 between the guide tool forks 934 located in the target facet joint space. The decorticating chisel 960 can then be displaced distal-proximal to cause the tapered decorticating distal end 972 of the chisel 960 to remove the cartilage of the target facet joint space located between the guide tool forks 934 and further decorticate any associated bone surfaces of the target facet joint space. Once the target facet joint space surfaces have been prepped with the decorticating chisel 960, the chisel 960 can be removed from the lumen of the guide tool 904 and the patient.

The implant 100 is coupled to, and supported off of, the distal end 906 of the implant delivery tool 902 of FIG. 10. As discussed above, the coupling of the implant delivery tool distal end 906 with the implant 100 may be achieved via interference fit and/or threaded engagement. With the implant supported off of the distal end 906 of the implant delivery tool 902 in a manner similar to that depicted in FIG. 10, the implant 100, and the delivery tool shaft 910 on which the implant 100 is supported, are distally routed through the lumen of the guide tool 904 until the implant 100 and the delivery tool distal end 906 are located in the target facet joint space between the pair of forks 934 of the guide tool distal end 907, the delivery tool 902, the guide tool 904 and the implant 100 being coupled together as depicted in FIG. 9. With the implant 100 so positioned in the target spinal facet join space, the member 916 may be used to deposit the implant 100 into the target spinal facet joint space by either plunging and/or threadably decoupling the implant 100 from the delivery tool distal end 906 via corresponding manipulation of the member 916 via its handle 920. Once the implant 100 is decoupled from the delivery tool 902 and deposited into the facet joint space, the delivery tool 902 can be withdrawn from the guide tool 904, which is left in place with its forked distal end 907 occupying the facet joint space and the implant 100 being located between the forks 934 of the guide tool 904.

With the implant 100 and forks 934 so positioned in the facet joint space and the guide tool shaft 924 extending from the patient, bone growth promoting paste may be plunged down the lumen of the guide tool 904 via the shaft 950 of the injector 948 being distally displaced down the lumen to cause the bone paste to exit the distal end 907 of the delivery tool 904 and extend about the implant 100 occupying the spinal facet joint space. The injector 948 and guide tool 904 can then be withdrawn from the patient, the implantation of the implant 100 in the facet joint having been completed. The process can then be repeated for another facet joint if needed.

Figure 17:
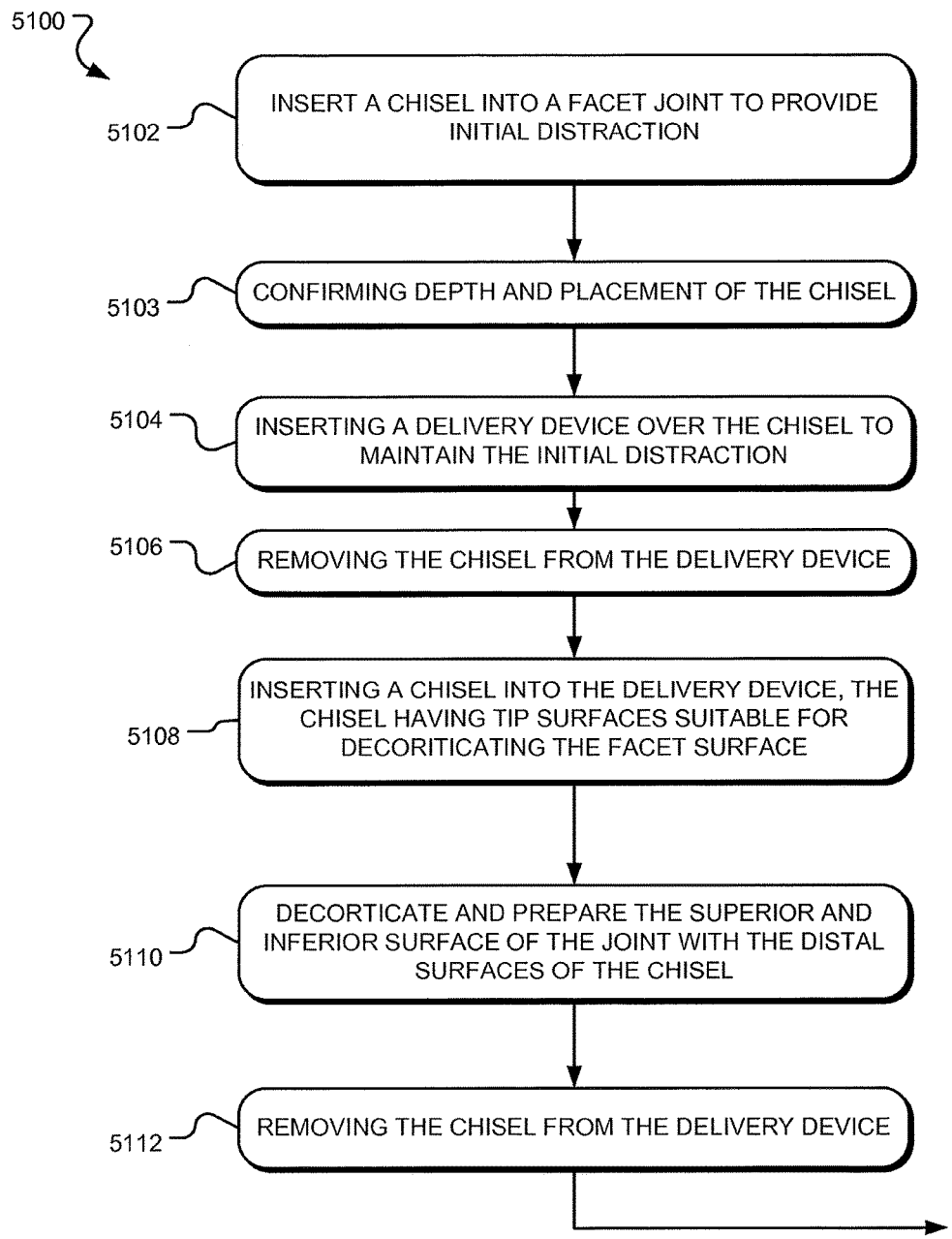
FIGS. 17-18 outline a method of implanting the implant in a spinal facet joint space.
Figure 18:
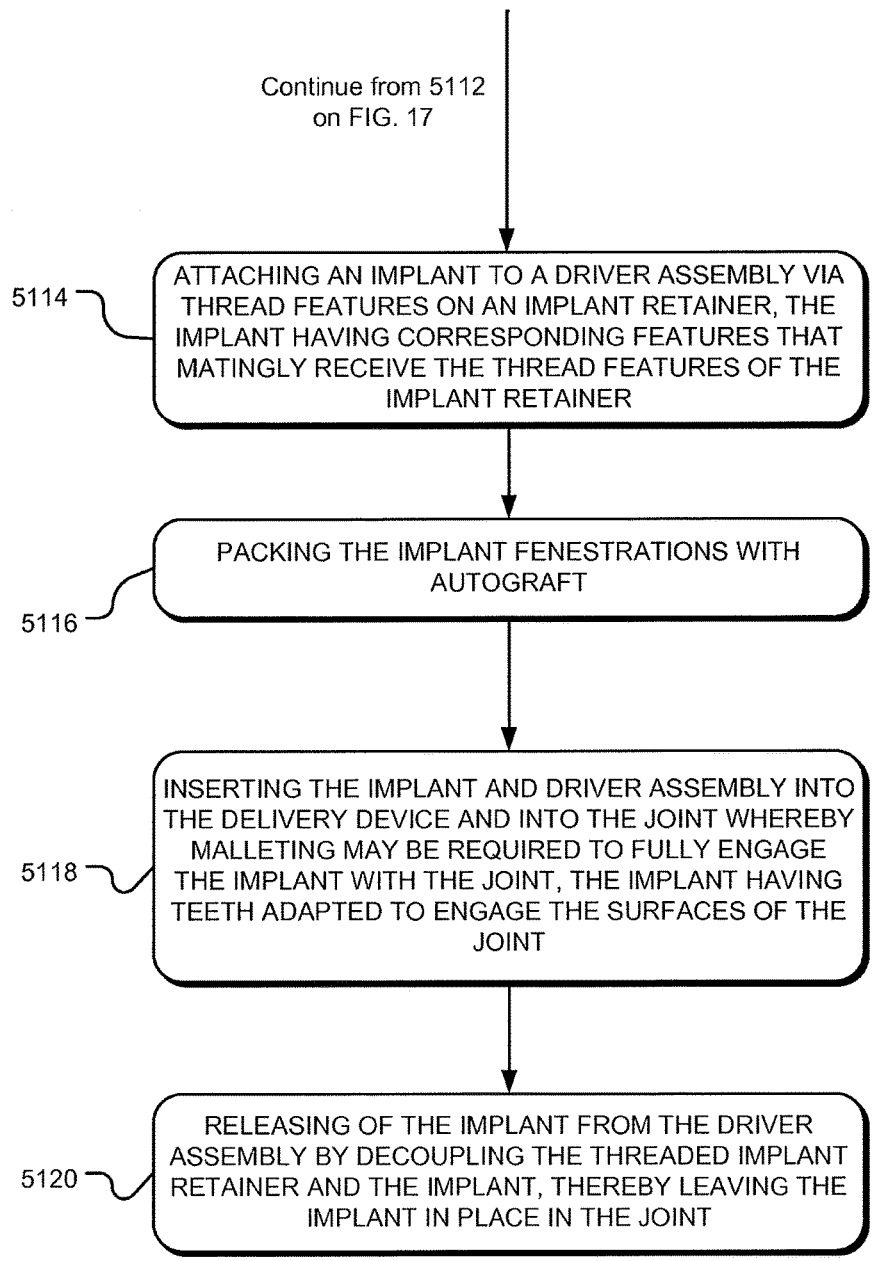

FIGS. 17-18 outline an embodiment of a method of implanting an embodiment of an implant in a spinal facet joint space. This method, and tools employed with this method embodiment, will now be discussed in reference to the flow chart depicted in FIGS. 17-18.

FIG. 19A is a side view of a place holding or access chisel similar to that already described above, and FIG. 19B is an enlarged perspective view of a distal portion of the chisel of FIG. 19A. As illustrated in FIGS. 19A-19B, the place holding or access chisel 5200 may have a generally cylindrical cross-section forming a shaft 5202. The shaft 5202 may have a radius substantially equal to the inner radius of a tubular shaft portion 5302 of a guide tube or tool 5300 similar to that already described above and again shown in FIG. 21. Because of this relationship, the access chisel 5200 can by slidably inserted within the guide tool 5300. The access chisel can include a single or doubly chamfered tip 5204 at a distal end of the shaft 5202. The access chisel may include radiolucent markers or holes 5208 extending through the shaft perpendicular to a longitudinal axis that extends along the length of the shaft. The radiolucent markers 5208 assist with confirming the appropriate depth of placement of the access chisel relative to the facet joint when used in conjunction with lateral fluoroscopy. As depicted in FIG. 19B, the tip 5204 of the access chisel 5200 can include a notch 5210 in the chamfered tip 5204 wherein a bore can extend through the chisel shaft 5202 to allow the insertion of a needle, guidewire or other medical device.

In some embodiments, the faces of the tip 5204 contain ridges, and, in other embodiments, the faces are ridgeless. The faces 5212 of the tip 5204 of the access chisel 5200 in the embodiment of FIG. 19A-B are ridgeless. In such an embodiment, resistance experienced by a user attempting to access a facet joint with the tip of the chisel 5200 may be minimized.

It is noted that the place holding or access chisel 5200 can be inserted into the facet joint prior to the insertion of a guide tool 5300. The access chisel 5200 may distract the facet joint by inserting the access chisel 5200 in the joint and tapping, hammering, or otherwise advancing the access chisel 5200 into the joint. After the access chisel 5200 distracts the facet joint, the guide tube 5300 may be sleeved over the access chisel with the forks 5304 of the guide tube 5300 inserting into the facet joint, whereby the access chisel 5200 may be removed.

Figure 20:
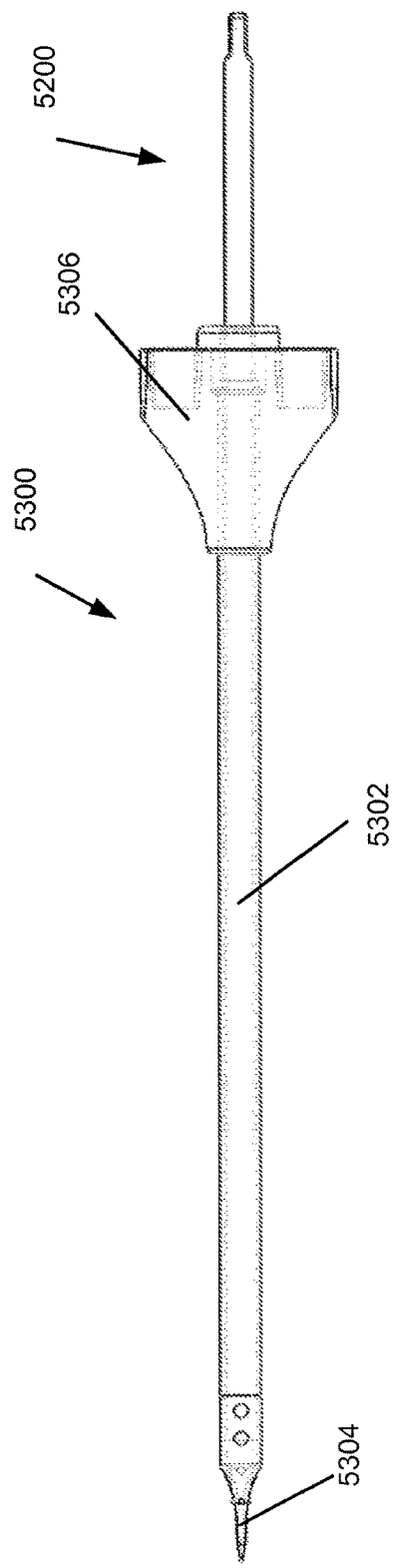
FIG. 20 is a side view of the chisel of FIG. 19A extending through a guide tube or tool.
Figure 21:
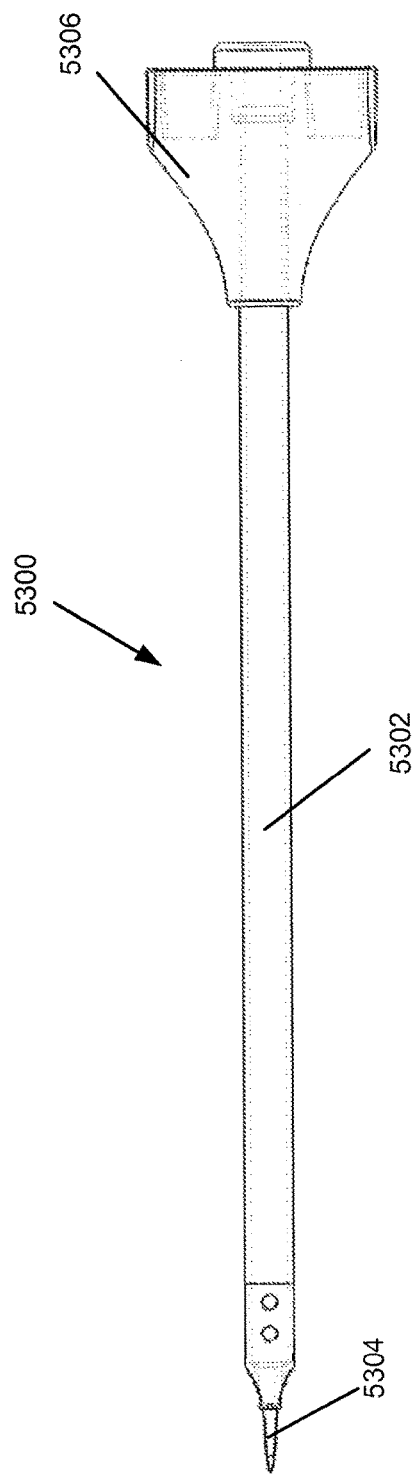
FIG. 21 is a side view of the guide tool of FIG. 20.

FIG. 20 is a side view of the access chisel of FIG. 19A extending through and a guide tube or tool, and FIG. 21 is a side view of the guide tool or tube of FIG. 20. As illustrated in FIGS. 20-21 and as similarly described above, the guide tube 5300 may include a receiving assembly 5306 at a proximal end, anchoring forks 5304 at a distal end, and a generally tubular shaft 5302 defining a longitudinal axis and extending between the receiving assembly 5306 and the anchoring forks 5304. As discussed previously, after the access chisel 5200 is inserted into the facet joint, the guide tube 5300 may be sleeved over the access chisel 5200. The guide tool forks 5304 support the loading force formerly on the access chisel 5200 such that the access chisel 5200 may be slidably removed from the guide tube 5300. Such variations of the guide tool 5300 are discussed above.

Figure 22:
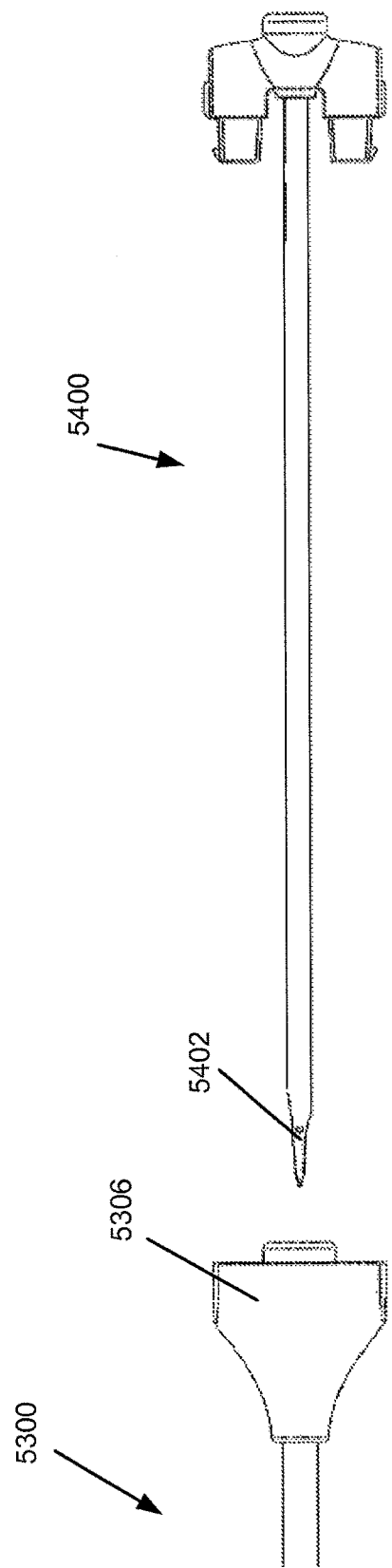
FIG. 22 is a side view of a decorticating chisel with a rasp end being introduced into a proximal end of the guide tool of FIG. 21.
Figure 23:
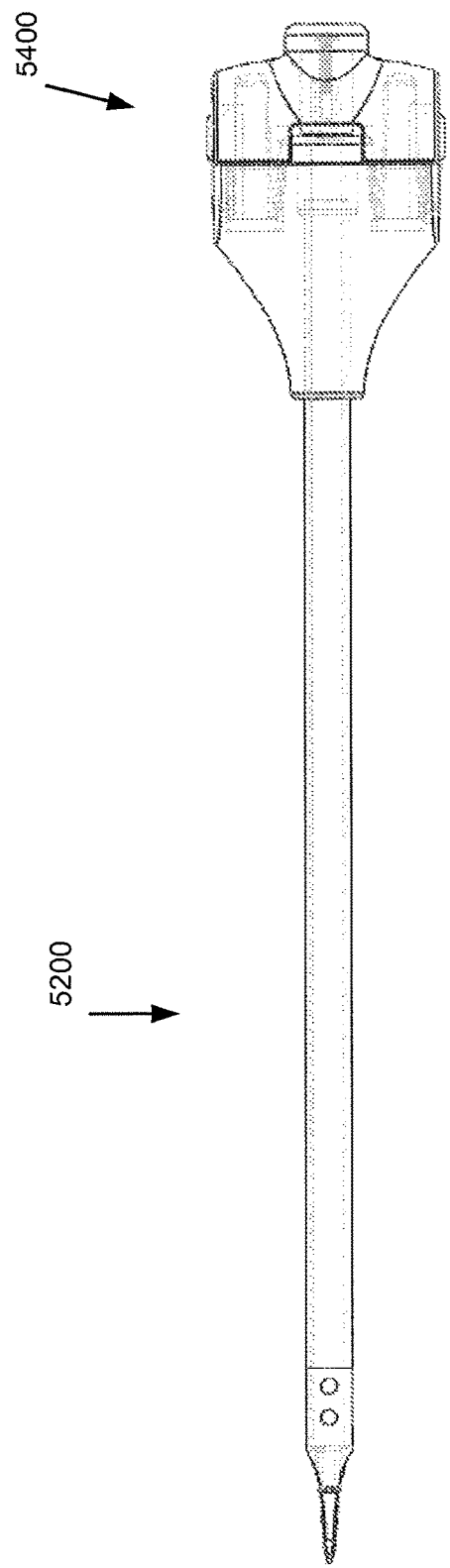
FIG. 23 is a side view of the decorticating chisel of FIG. 22 fully inserted in the guide tool, wherein the devices so coupled together can be considered to form a driver assembly.

FIG. 22 is a side view of a decorticating chisel with a rasp end being introduced into a proximal end of the guide tool 5300 of FIG. 21. FIG. 23 is a side view of the decorticating chisel of FIG. 22 fully inserted in the guide tool 5300, wherein the devices so coupled together can be considered to form a driver assembly. As indicated in FIGS. 22-23, after removal of the place holding or access chisel 5200 from the guide tube or tool 5300, a decorticating chisel 5400 or other suitable chisel may be inserted into the delivery device to decorticate the articular surfaces of the facet joint by manipulating the decorticating chisel 5400 within the joint. This may include tapping the decorticating chisel 5400 with a device such as a hammer, mallet, or other instrument to advance the distal tip 5402 of the decorticating chisel 5400 and may also include moving the proximal end of the decorticating chisel laterally from side to side, up and down, or rotationally, to decorticate the joint surface. The decorticating chisel 5400 may then be tapped into place anteriorly such that it extends substantially through the joint. Fluoroscopy from one or more directions may be used to verify the location of the decorticating chisel 5400. The decorticating chisel 5400 may then be removed from the facet joint.

FIGS. 24 and 25 are perspective views of various distal tip portions of the decorticating chisel 5400 positioned between distal laterally or transversely spaced-apart forks of the distal end of the guide tool 5300. As shown in FIGS. 24-25, the surfaces of the tip 5402 of the decorticating chisel 5400 include a series of ridges 5406. The ridges 5406 can be relatively sharp and can aid the user in roughening or decorticating the facet surfaces as the decorticating chisel 5400 is inserted and removed from a facet joint. The ridges 5406 can include a pattern adapted to maintain the chisel's position in a facet joint. In some embodiments, the ridges 5406 can include a sloping distal face and a relatively vertical (e.g., perpendicular to axis of chisel 5400) proximal face. As the decorticating chisel 5400 is advanced, the surfaces in contact with the decorticating chisel 5400 may ride up along the sloping distal face until the decorticating chisel 5400 is positioned. The relatively sharp apex of the ridges 5406 formed by the sloping distal face and relatively vertical proximal face can function to hold the decorticating chisel in place. Moreover, the ridges 5406 can be arranged in a surface pattern suitable for holding the decorticating chisel 5400 in place. In one embodiment, referring to FIG. 25, the ridges 5406 can include a chevron pattern. Referring to FIG. 24 the ridges 5406 can include a pattern of rows of steps that extend along the incline of the face wherein a recessed groove is positioned between the rows. Other patterns such as straight rows, diagonal rows, wavy rows, or other alternative patterns can be included.

Figure 26:
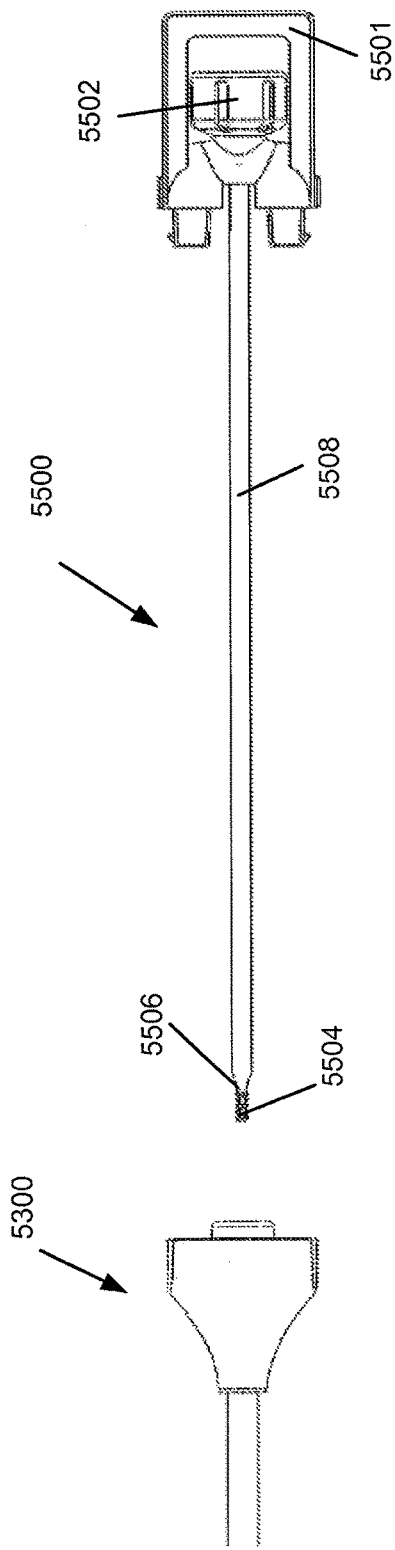
FIG. 26 is a side view of a driver device or delivery tool supporting the implant from a distal end of the delivery tool, the delivery tool being positioned to be inserted in a proximal portion of the guide tool.
Figure 27:
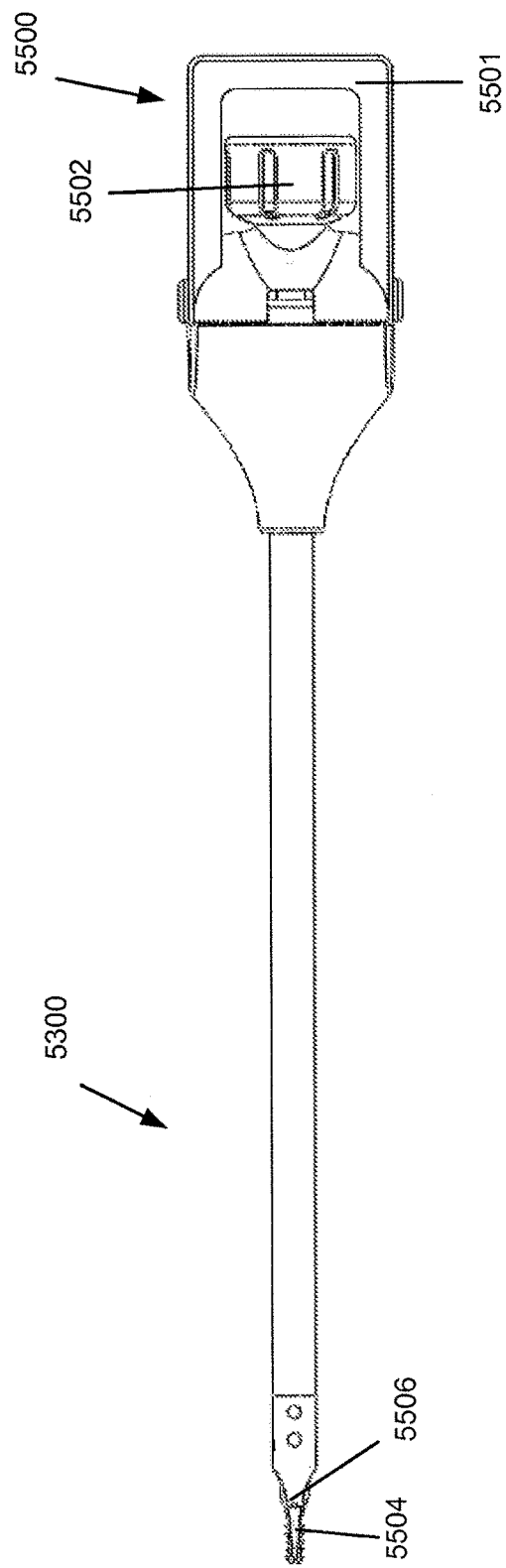
FIG. 27 is a side view of the driver device fully received in the guide tool.
Figure 28:
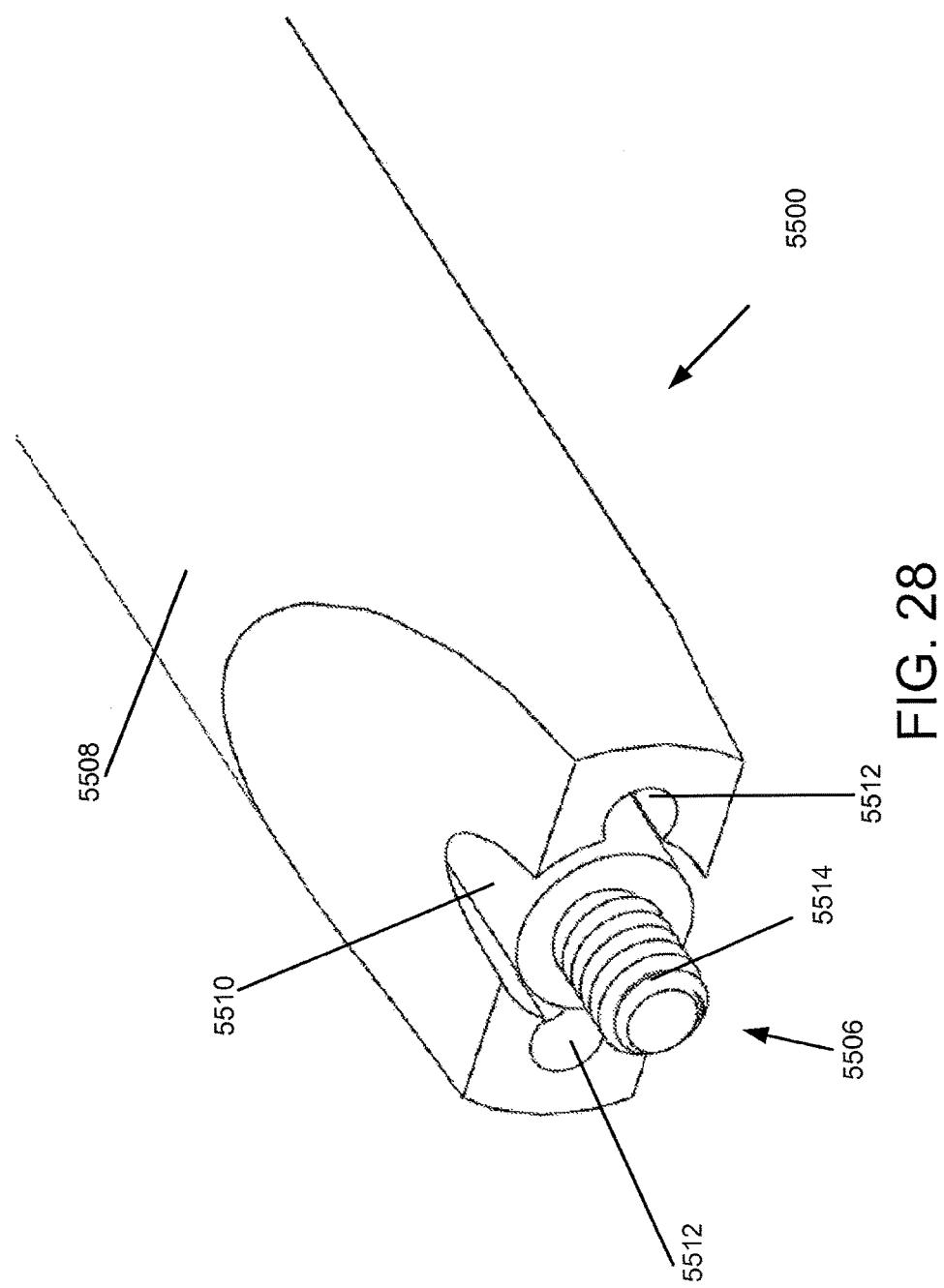
FIG. 28 is an enlarged perspective view of a distal end of the driver device, wherein a threaded male member is visible for threadably coupling with the implant.
Figure 29:
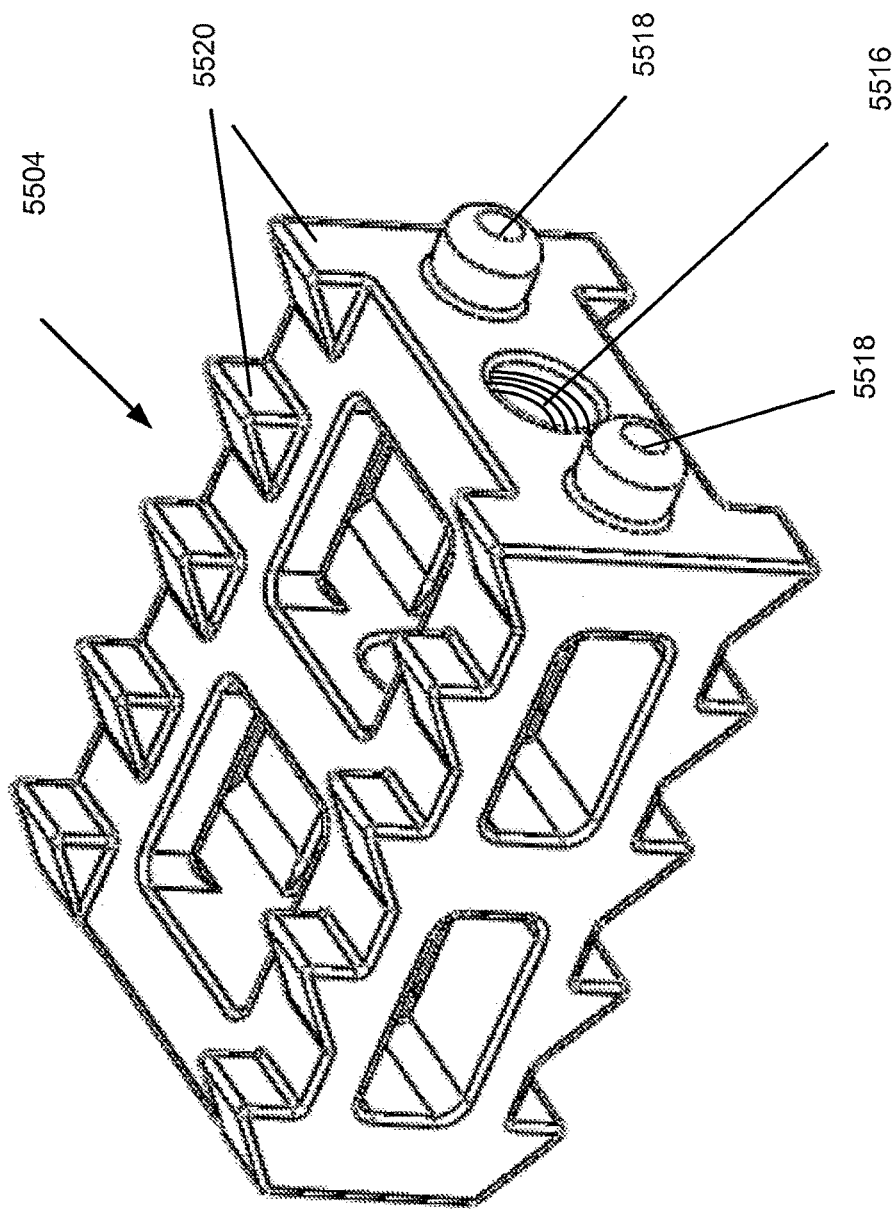
FIG. 29 is a perspective view of the implant wherein a threaded female opening is depicted in a proximal face of the implant.

FIG. 26 is a side view of a driver device or delivery tool supporting the implant from a distal end of the delivery tool, the delivery tool being positioned to be inserted in a proximal portion of the guide tool. FIG. 27 is a side view of the driver device fully received in the guide tool. FIG. 28 is an enlarged perspective view of a distal end of the driver device, wherein a threaded male member is visible for threadably coupling with the implant. FIG. 29 is a perspective view of the implant wherein a threaded female opening is depicted in a proximal face of the implant.

As shown in FIG. 26 and as similarly described above, the driver assembly or delivery tool 5500 includes a handle 5501, an implant shaft 5508, an implant retainer 5506, and an internal actuator 5502. An internal rod 5510, which is coupled to the internal actuator 5508 and the implant retainer 5506 and illustrated in FIG. 28, transfers the force from the internal actuator 5502 to the implant retainer 5506. As depicted in FIGS. 26-27, the driver assembly or delivery tool 5500 is slidably received in the guide tool 5300 for inserting the implant 5504 into the patient's facet joint.

As can be understood from FIG. 28, the distal end of the driver assembly 5500 includes an internal rod 5510 and an implant retainer 5506 at the distal end of the internal rod 5510 adapted to secure an implant during insertion and distraction of the implant into the joint. Further, in some embodiments, the distal end or face of the driver assembly 5500 includes implant receiving notches 5512 for rotationally orienting and securing the implant relative to the driver assembly.

The internal rod 5510, shown in FIG. 28, may be positioned within the shaft 5508 and may extend from the handle 5501 to the distal end of the longitudinal shaft 5508. The implant retainer 5506 includes an engagement feature 5514 at its distal end for engaging and holding the implant 5504. This engagement feature 5514 may be a thread feature such as, for example a male-end of a screw. In the embodiment where the engagement feature 5514 is a thread feature, the exact type and characteristics of the thread feature can vary accordingly so as to adequately retain an implant during insertion and distraction of a facet joint. The engagement feature 5514 may be any shape and provide for any engagement known in the art capable of transmitting longitudinal and/or rotational forces from the internal rod 5510 to engage corresponding features on an implant 5504. For example the engagement feature can include a keyed shaft and coupler, splined shaft and coupler, etc.

Those skilled in the art would appreciate that although the various embodiments depict the engagement feature 5514 as a male-end thread feature at the distal end of the internal rod 5510 and a corresponding internal female-end receiving thread featured implant, the tool 5000 can function similarly by including a male-end thread feature on the proximal end of an implant and a corresponding internally threaded female receiving feature on a distal end of the internal rod 5510.

As depicted in FIGS. 28-29, the distal end of the driver assembly 5500 includes implant receiving notches 5512 for rotationally orienting and securing the implant relative to the driver assembly 5500. The implant 5504 includes corresponding implant knobs 5518 that friction fit into the implant receiving notches 5512 of the driver assembly 5500. Additionally, the implant 5504 is generally rectangular and cage-shaped, with opposing upper and lower faces that include teeth 5504 that extend outward from the upper and lower planar faces in a general spaced-out saw tooth orientation.

In one particular embodiment, as depicted in FIG. 29, the implant 5504 includes an internally threaded female receiving feature 5516 that is adapted to matingly receive the engagement feature 5514, which in this embodiment is a thread feature. The implant knobs 5518 aid in resisting rotational movement of the implant relative to the driver assembly 5500 when the knobs 5518 are matingly received in the implant receiving notches 5512. A surgeon or surgical assistant may place the implant knobs 5518 in the receiving notch 5512, prior to insertion into the guide tube 5300, so that the as the engagement features 5514 of the implant retainer 5506 engage the implant, the implant 5504 remains a constant orientation relative to the driver assembly 5500.

Figure 36:
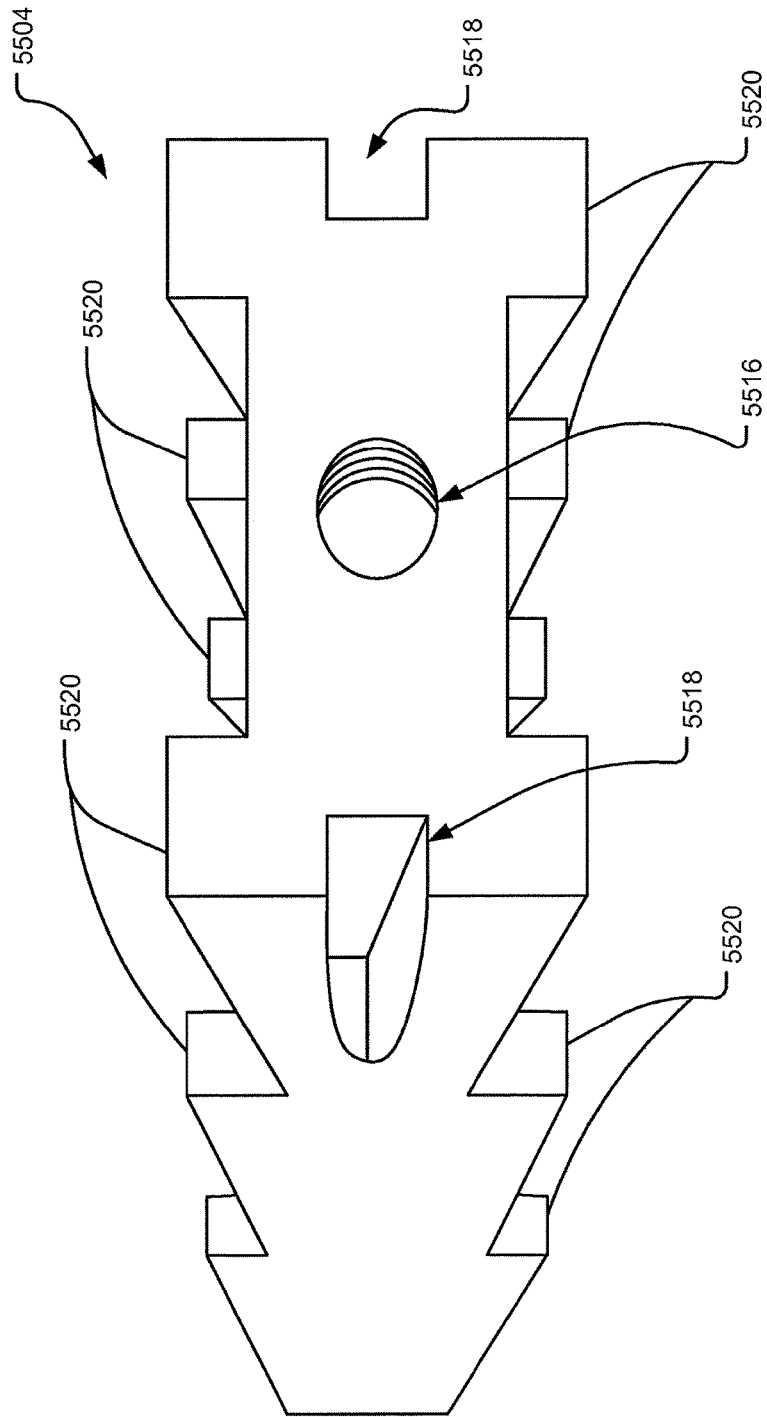
FIG. 36 shows a perspective view of a proximal or trailing end of an implant.

As indicated in FIG. 36, which is a perspective view of a proximal or trailing end of an implant 5504, in one embodiment, the implant 5504 may have other features for preventing rotational displacement between the implant and the driver assembly 5500. For example, instead of having the male/female pin/recess 5518/5512 arrangement between the implant and distal end of the driver assembly depicted in FIGS. 197-198, the implant 5504 could include slots 5518 extending along at least part of each lateral side surface from the proximal trailing face of the implant 5504, as depicted in FIG. 36. Corresponding arms or pins (not shown, but easily visualized and understood by someone of ordinary skill in the art) could distally extend from the distal leading face of the distal leading end of the driver assembly 5500 to be matingly received in the slots 5518 depicted in FIG. 36. The arms or pins being received in the slots 5518 of FIG. 36 would prevent rotation of the implant relative to the driver assembly.

Figure 30:
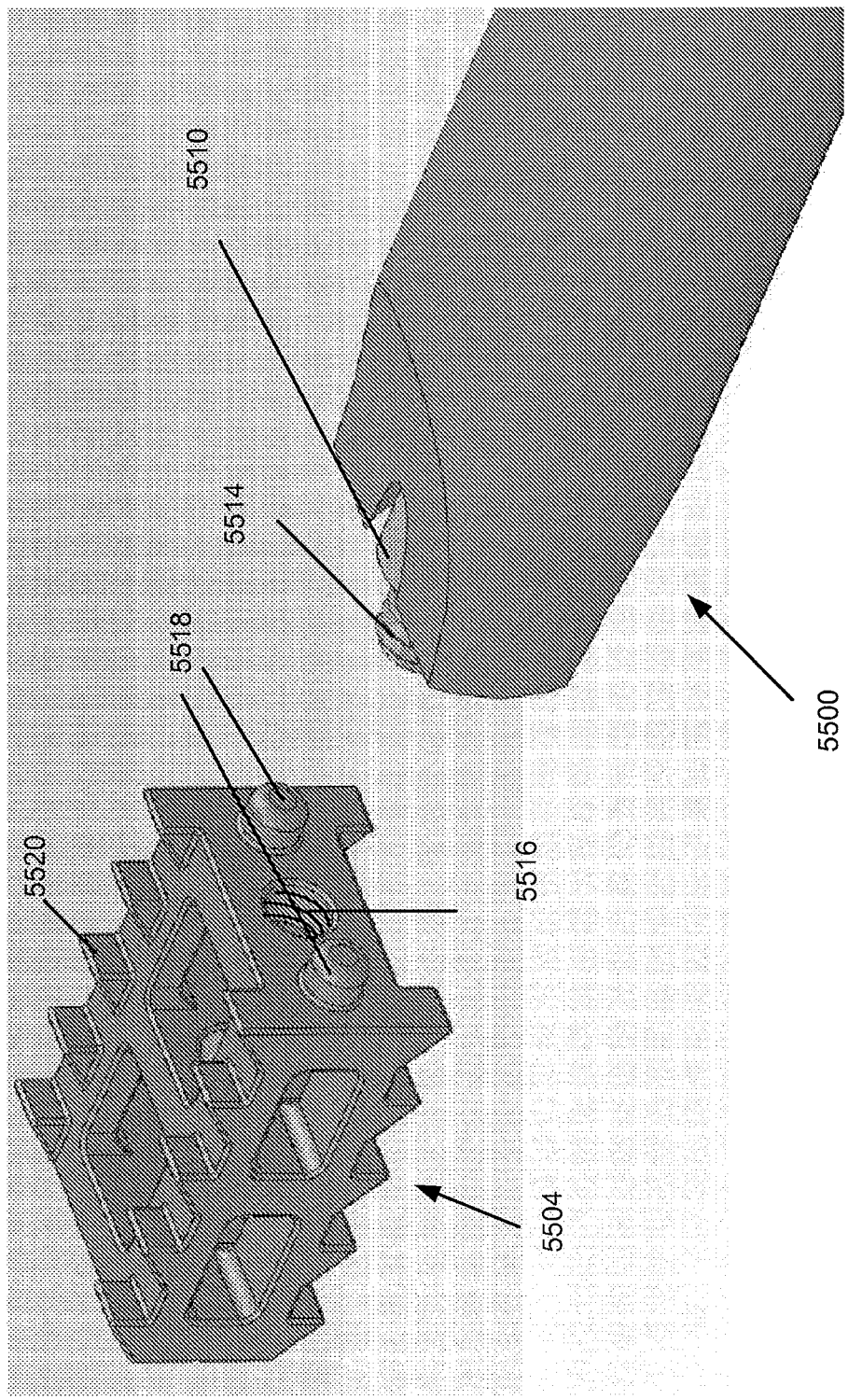
FIG. 30 is a perspective view of the distal end of the driver assembly approaching the proximal end of the implant to achieve coupling between the two.
Figure 31:
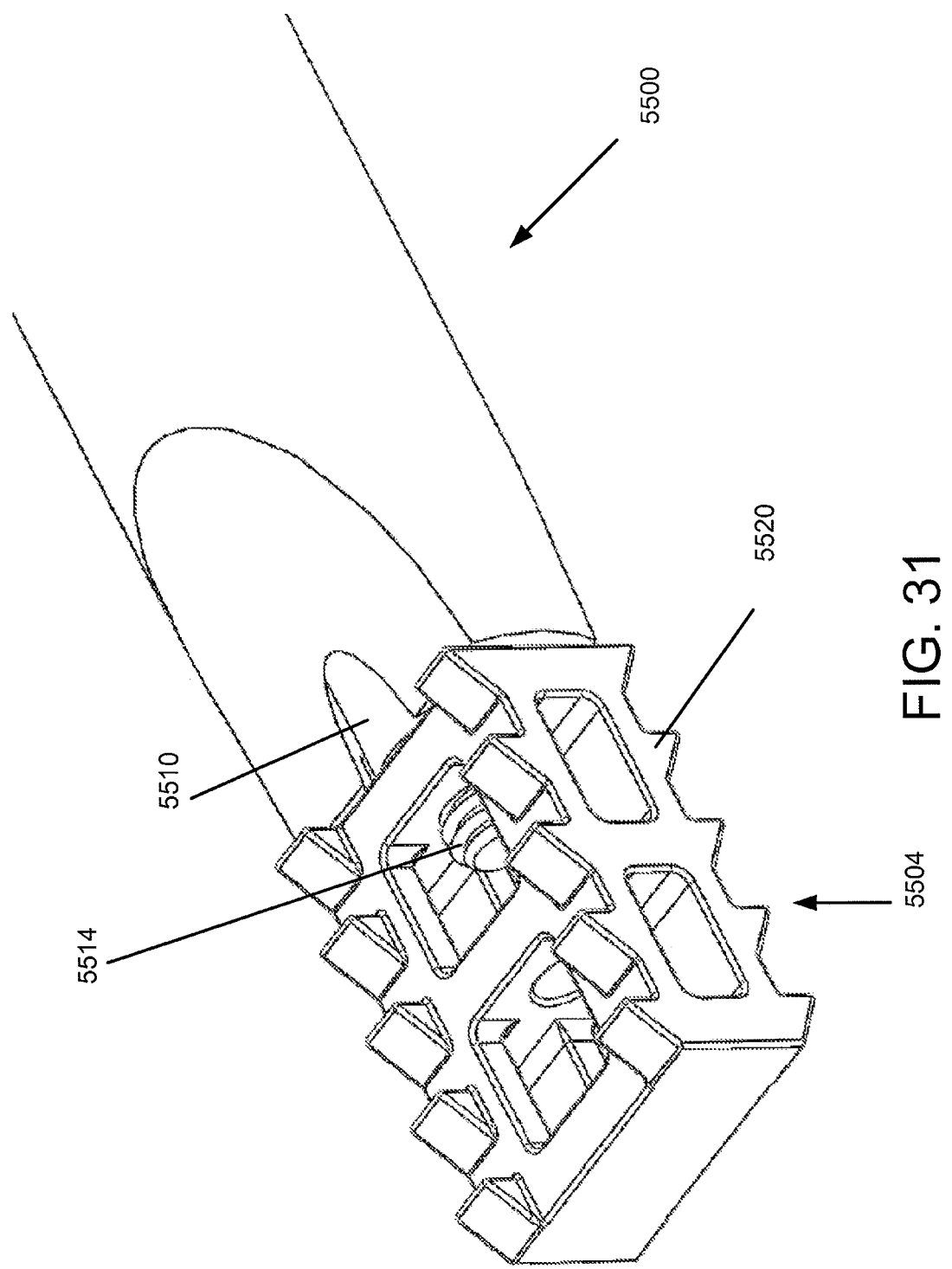
FIG. 31 is a perspective view of the distal end of the driver assembly coupled to the proximal end of the implant.
Figure 32:
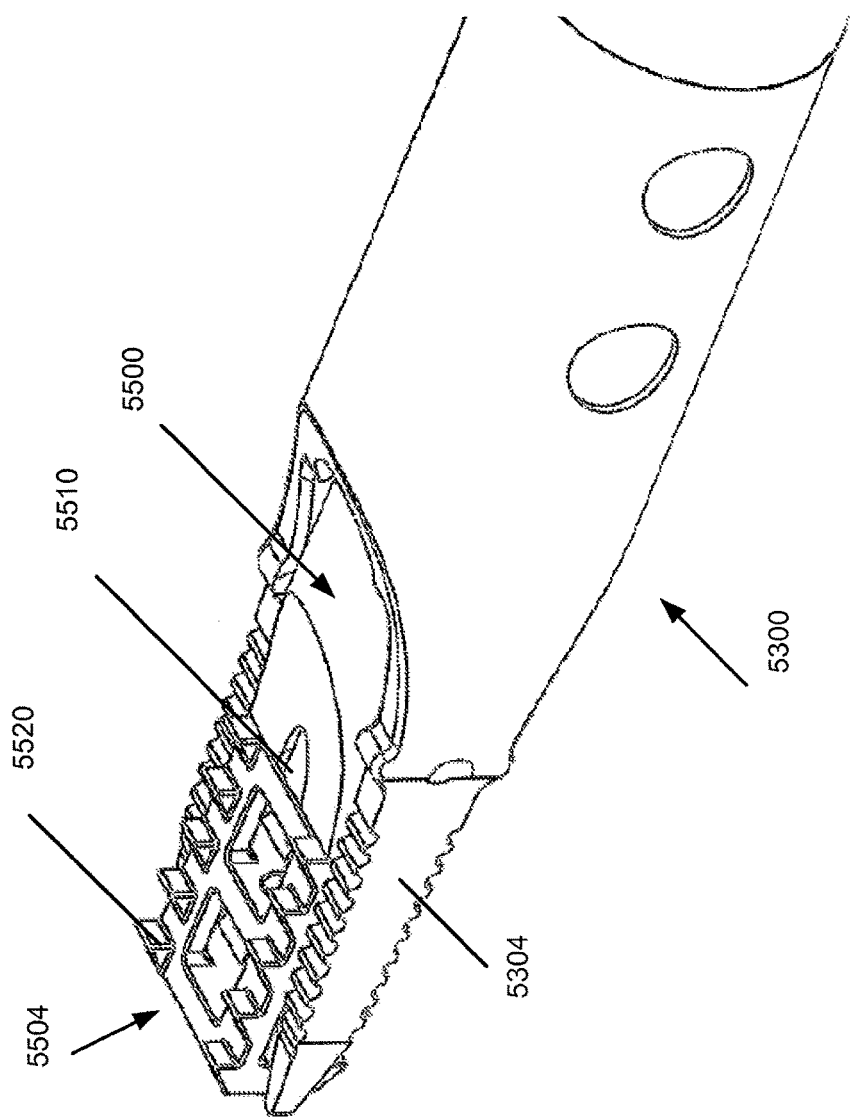
FIG. 32 is a perspective view of the guide tool, driver assembly, and implant wherein the implant is coupled to the distal end of the driver assembly and nestled between the forks of the guide tool.
Figure 33:
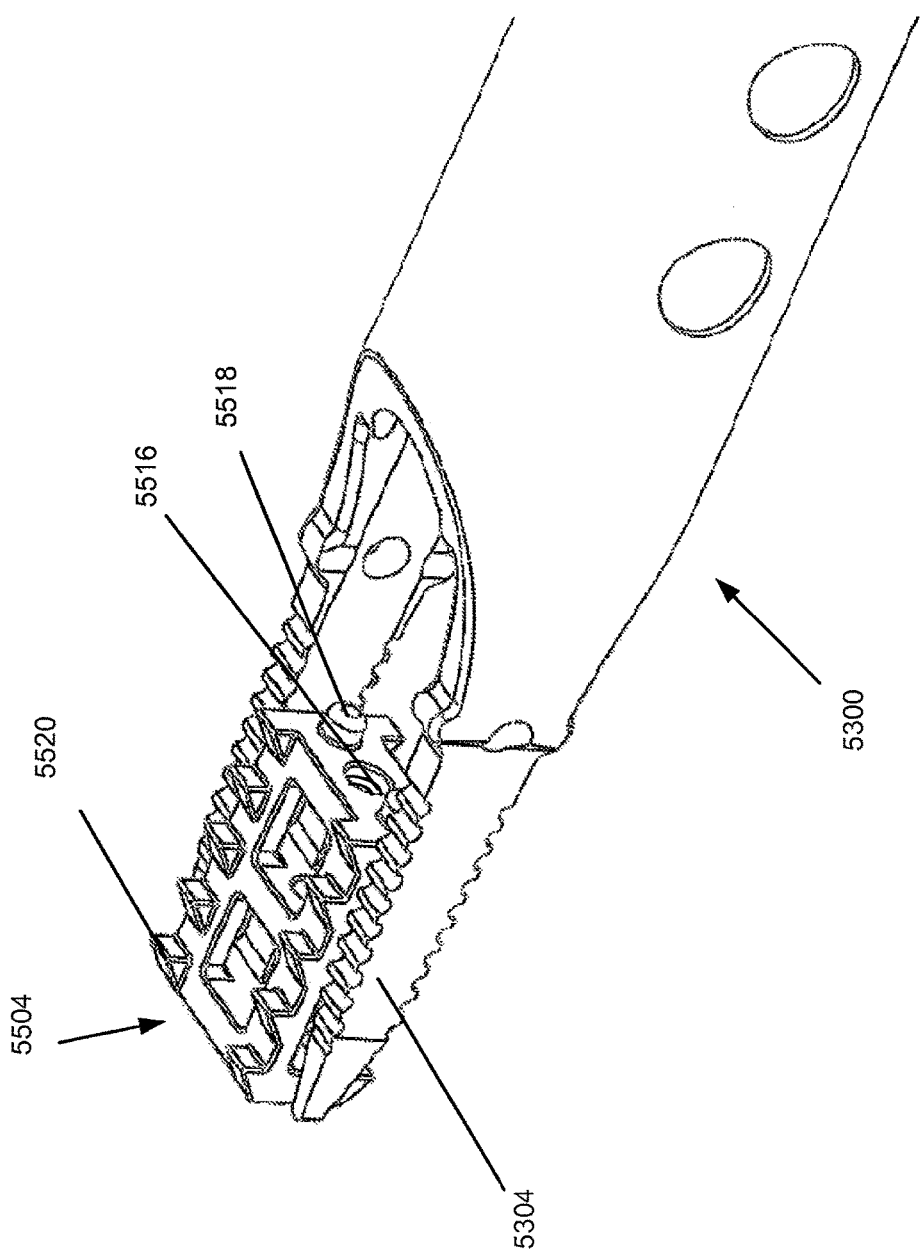
FIG. 33 is the same view as FIG. 32, except the driver assembly has been decoupled from the implant and withdrawn from within the guide tube.
Figure 34:
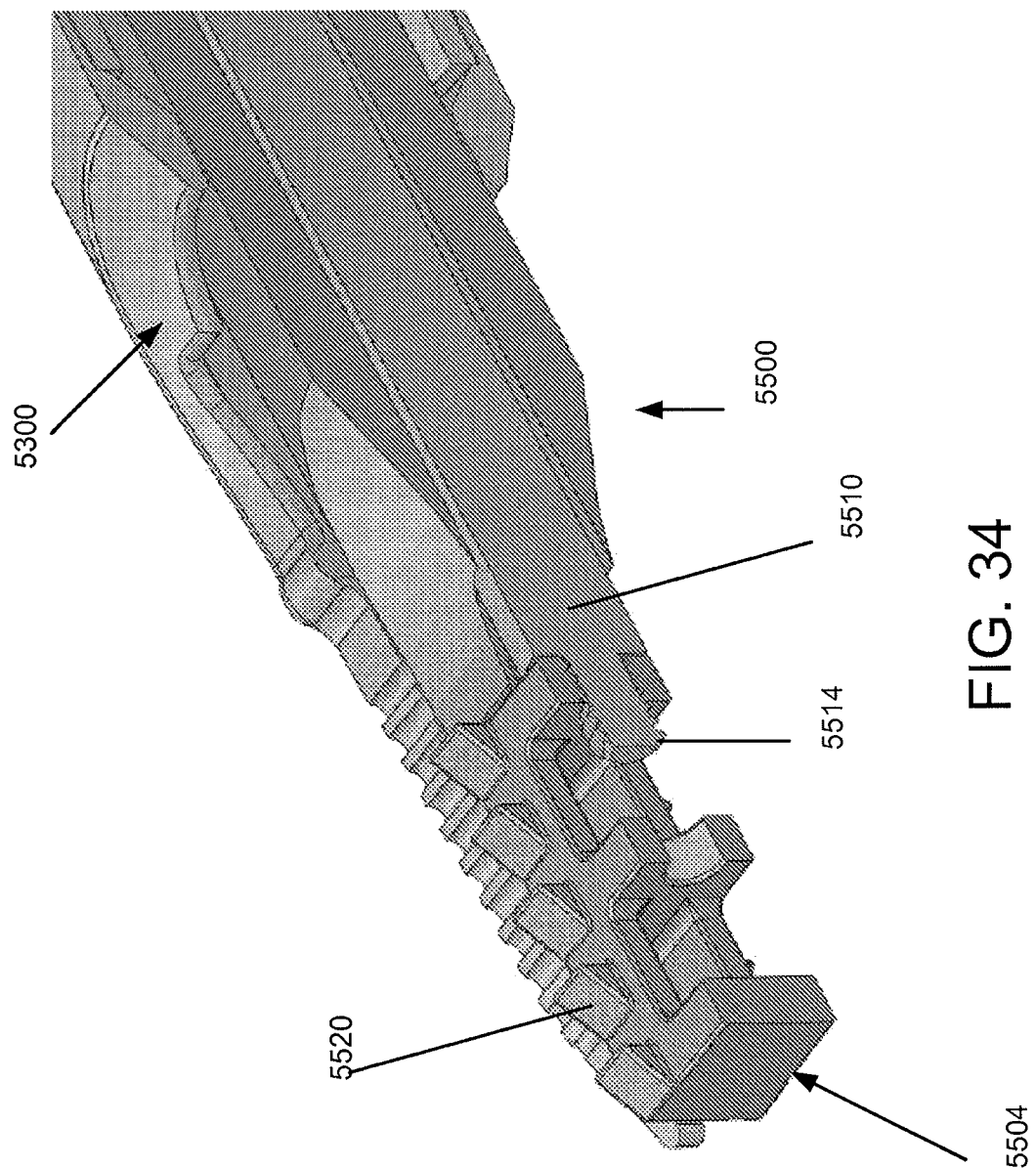
FIGS. 34 and 35 are longitudinal cross sections of the arrangement depicted in FIG. 32.
Figure 35:
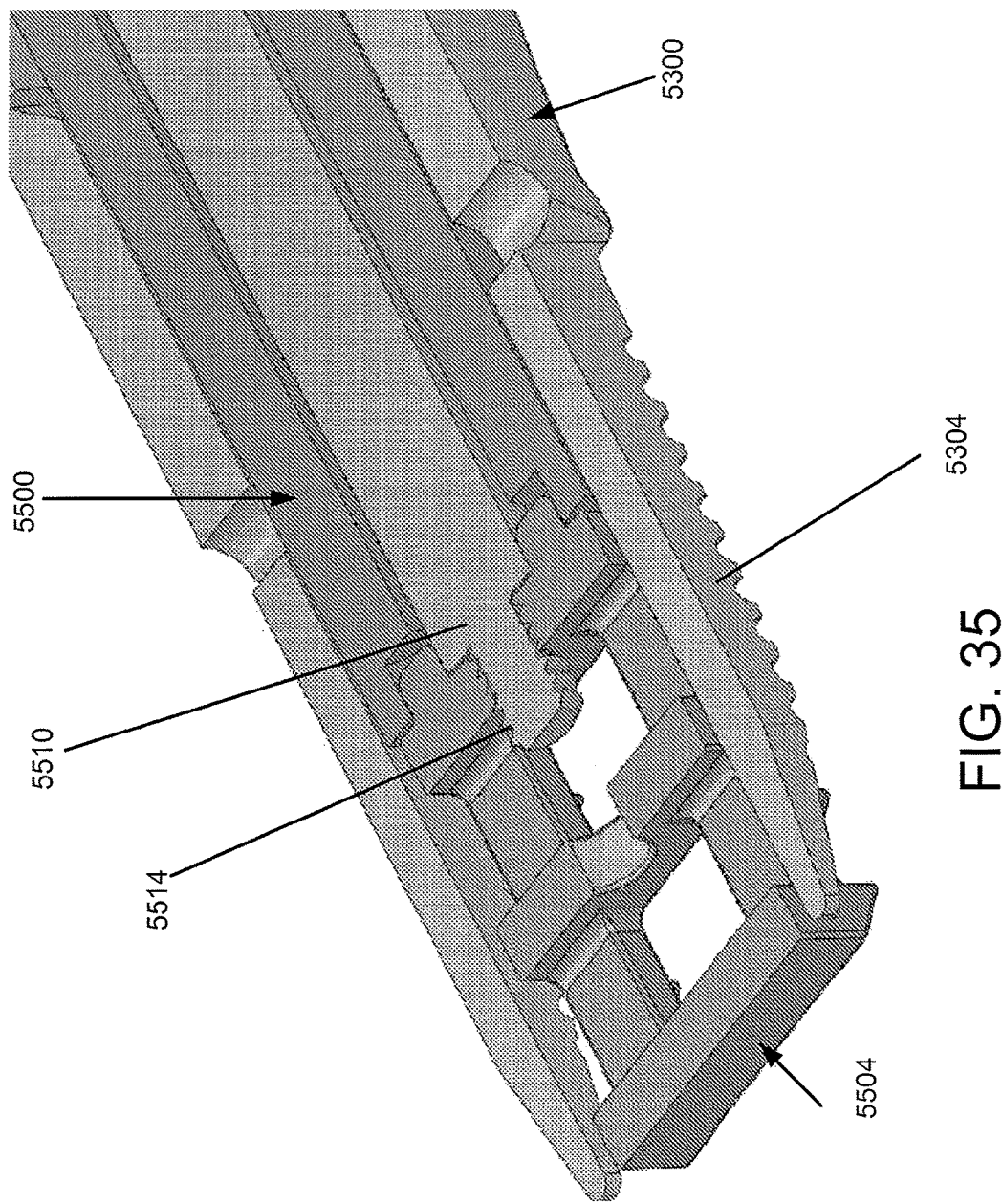

FIG. 30 is a perspective view of the distal end of the driver assembly 5500 approaching the proximal end of the implant to achieve coupling between the two. FIG. 31 is a perspective view of the distal end of the driver assembly coupled to the proximal end of the implant. FIG. 32 is a perspective view of the guide tool, driver assembly, and implant wherein the implant is coupled to the distal end of the driver assembly and nestled between the forks of the guide tool. FIG. 33 is the same view as FIG. 32, except the driver assembly has been decoupled from the implant and withdrawn from within the guide tube. FIGS. 34 and 35 are longitudinal cross sections of the arrangement depicted in FIG. 32.

In certain embodiments, in reference to FIGS. 30-35, the implant retainer 5506 is such that rotation of the internal actuator 5502 causes the implant retainer 5506 and the corresponding engagement feature 5514 to rotate and translate proximally and/or distally, depending on the direction of rotation of the internal actuator 5502. As such, to engage the implant 5504 with the driver assembly 5500, the implant knobs 5518 are engaged with the implant receiving notches 5512 and the internal actuator is rotated such that the engagement feature 5514 that was recessed to a point to allow the implant knobs 5518 to be engaged with the notches 5512 is now rotating and translating out of its recessed state and into engagement with the female receiving portion 5516 of the implant 5504. Correspondingly, after the implant is inserted into the patient's facet joint, the internal actuator is rotated in an opposing direction and the engagement feature 5514 of the implant retainer 5506 therefore rotates and translates distally back into a recessed state within the shaft 5508 of the driver assembly 5500. In this way, the engagement feature 5514 of the implant retainer 5506 "backs out" and releases the implant 5504 in the facet joint.

In another embodiment, also with reference to FIGS. 30-35, the implant retainer 5506 is such that rotation of the internal actuator 5502 only causes rotational motion of the implant retainer 5506 and thus the engagement feature 5514 (i.e., the implant retainer 5506 does not translate proximally and distally to a recessed and non-recessed state). As such, to engage the implant 5504 with the driver assembly 5500, the implant 5504 is positioned adjacent the engagement features 5514 and the internal actuator is rotated such that the engagement feature rotatably engages with corresponding internally threaded feature 5516 of the implant 5504 and the implant retainer 5504 thereby "pulls" the implant 5504 into engagement with the implant retainer 5504. Note that in this embodiment, the implant knobs 5518 are engaged with the implant receiving notches 5512 by the "pulling" together of the implant 5504 by the implant retainer 5506. Once the implant is inserted into the patient's facet joint, the internal actuator 5502 is rotated in an opposing direction and the engagement feature 5514 of the implant retainer 5506 therefore rotates and "pushes" the implant 5504 out of engagement with the implant retainer 5506.

Referring to FIGS. 31-33, once the implant 5504 is coupled to the driver assembly 5500, the implant 5504 can optionally be packed with autograft (i.e., autologous bone) before implantation into the patient's facet joint. The implant 5504 and driver assembly 5500 is slidably inserted into the guide tube 5300. In order to fully "seat" the implant into the delivery device 5300 and in the facet joint, malleting may be required since the upper and lower faces of the cage-shaped implant 5504 can protrude above the forks 5304, which were providing the holding force for the distraction.

FIGS. 34-35 depict cross-sectional views of the tool 5000 and implant 5504. Engagement of the implant 5504 with the engagement features 5514 is clearly visible, as is the nesting relation between the forks of the guide tube 5300 and the driver assembly 5500 and between the internal rod 5510 and the driver assembly 5500.

Referring to FIGS. 17-18, a method of performing an interbody fusion can include inserting an access chisel into a joint between vertebral bodies of the spine to provide for initial distraction of the facet joint (5102), confirming the depth and placement of the access chisel using radiolucent markers or holes in the shaft of the access chisel (5103), inserting a guide tool over the access chisel to maintain the initial distraction (5104), removing the access chisel from the guide tool (5106), inserting a decorticating chisel into the guide tool for decorticating the facet surface (5108), decorticate and prepare the superior and inferior surface of the joint with the distal surfaces of the decorticating chisel (5110), removing the decorticating chisel from the guide tool (5112), attaching an implant to a driver assembly via thread feature on an implant retainer, the implant having corresponding features that matingly receive the thread feature of the implant retainer (5114), packing the implant fenestrations with autograft (5116), inserting the implant and driver assembly into the guide tool and into the joint, whereby malleting may be required to fully engage the implant with the joint, the implant having teeth adapted to engage the surfaces of the joint (5118), and releasing of the implant from the driver assembly by decoupling the threaded implant retainer and the implant, thereby leaving the implant in place in the joint (5120).

For a further discussion regarding delivery systems and methodology, see U.S. patent application Ser. No. 12/653,283, which was filed on Dec. 10, 2009 and entitled "Verbal Joint Implants and Delivery Tools."

The description above includes example systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. An implant for implantation in a spinal facet joint, the implant comprising:
   a distal leading portion having a distal end surface generally opposite a proximal end surface of a proximal trailing end;
   a first side having a first side surface generally opposite a second side having a second side surface;
   a first face having a first surface that is generally opposite a second surface of a second face, the first and second faces extending between a portion of the distal leading portion and the proximal trailing end, the first and second surfaces having one or more discrete textured features, wherein at least one of the one or more of the textured features is a tooth comprising an inner side surface generally opposite an outer side surface, the outer side surface is adjacent to a respective side surface of the first or second side and at least a portion of the inner side surface is generally perpendicular to the first surface of the first face or the second surface of the second face;
   one or more windows defined in the first surface generally opposing one or more windows defined in the second surface; and
   one or more side windows defined in the first side surface generally opposing one or more windows defined in the second side surface, the windows and side windows providing access to a hollow interior of the implant.

2. The implant of claim 1, wherein the textured features include a ridge extending perpendicularly from each of the first and second surfaces along at least a portion of the length of the first and second surfaces, the ridge defined by the one or more teeth wherein the distal surface is a leading distal face, the proximal surface is a trailing proximal face, and a tip is formed at an intersection between the leading distal face and the trailing proximal face.

3. The implant of claim 2, wherein the trailing proximal face has a slope that is greater than a slope of the leading distal face.

4. The implant of claim 2, wherein the ridges extend across the first and second surfaces of the first and second faces from the first side to the second side.

5. The implant of claim 1, wherein the textured features include a plurality of protrusions extending perpendicularly from each of the first and second surfaces.

6. The implant of claim 5, wherein the protrusions each have a pyramidal shape with a rectangular base that is generally parallel to a respective surface of the first face and the second face.

7. The implant of claim 5, wherein the protrusions form one of small pyramids or large pyramids.

8. The implant of claim 5, wherein the protrusions are arranged in rows, a first row of the protrusions abutting a second row of the protrusions.

9. The implant of claim 1, wherein the textured features include a plurality of grit particles extending generally perpendicularly from a respective surface of the first face and the second face and the grit particles are randomly adhered to the surfaces of the first face and the second face.

10. The implant of claim 1, wherein the textured features include a plurality of pits extending generally perpendicularly into a respective surface of the first face and the second face.

11. The implant of claim 10, wherein the plurality of pits cover a respective surface of the first face and the second face in a random orientation.

12. The implant of claim 10, wherein the plurality of pits are achieved as a result of surface treating the surfaces of the first face and the second face.

13. The implant of claim 1, wherein the windows and the side windows are rectangular in shape.

14. The implant of claim 1, wherein the windows are circular in shape.

15. A spinal facet cage implant for implantation in a spinal facet joint, the implant comprising:
   a distal leading portion having a distal end surface generally opposite a proximal end surface of a proximal trailing end;
   a first side having a first side surface generally opposite a second side having a second side surface;
   a first face having a first surface that is generally opposite a second surface of a second face, the first and second faces extending between at least a portion of the distal leading portion and the proximal trailing end, the first and second surfaces having one or more discrete textured features, wherein at least one of the one or more of the textured features is a tooth comprising an inner side surface generally opposite an outer side surface, the outer side surface is adjacent to a respective side surface of the first or second side and at least a portion of the inner side surface is generally perpendicular to the first surface of the first face or the second surface of the second face;
   a set of distal windows positioned near the distal leading portion and including a distal window defined in the first surface of the first face and a distal side window defined in the side surface of the first side, the set of distal windows providing an opening to a distal chamber in an interior of the implant; and
   a set of proximal windows positioned near the proximal trailing end and including a proximal window defined in the first surface of the first face and a proximal side window defined in the side surface of the first side the set of proximal windows providing an opening to a proximal chamber in an interior of the implant.

16. The implant of claim 2, wherein the trailing proximal face has a slope that is less than a slope of the leading distal face.

17. The implant of claim 2, wherein the trailing proximal face has a slope that is approximately the same as a slope of the leading distal face.

18. The implant of claim 1, wherein the spinal facet joint is a cervical facet joint.

19. The implant of claim 15, wherein the spinal facet joint is a cervical facet joint.

20. The implant of claim 1, wherein the at least one of the one or more of the textured features further comprises a proximal surface and a distal surface and the proximal surface is adjacent to and in a same plane as at least a portion of the proximal end surface of the proximal trailing end.

* * * * *